(12) United States Patent
Goto et al.

(10) Patent No.: US 6,319,916 B1
(45) Date of Patent: Nov. 20, 2001

(54) HETEROCYCLIC COMPOUNDS, THEIR PRODUCTION AND USE

(75) Inventors: Giichi Goto, Toyono-cho; Masaomi Miyamoto, Takarazuka; Yuji Ishihara, Itami, all of (JP)

(73) Assignee: Takeda Chemical Industries, Ltd., Osaka (JP)

(*) Notice: Subject to any disclaimer, the term of this patent is extended or adjusted under 35 U.S.C. 154(b) by 0 days.

(21) Appl. No.: 08/051,831

(22) Filed: Apr. 23, 1993

(30) Foreign Application Priority Data

| Apr. 24, 1992 | (JP) | ................................ 4-106789 |
| Jul. 31, 1992 | (JP) | ................................ 4-205650 |
| Nov. 19, 1992 | (JP) | ................................ 4-309872 |

(51) Int. Cl.[7] ............... C07D 267/02; C07D 267/14; C07D 413/06; C07D 31/553
(52) U.S. Cl. ...................... 514/211.09; 540/552
(58) Field of Search .................. 540/552; 514/211.09

(56) References Cited

U.S. PATENT DOCUMENTS

| 4,613,598 | * | 9/1986 | Fukami et al. ................. 514/211 |
| 4,849,431 | | 7/1989 | Sugimoto et al. ............... 514/331 |
| 4,895,841 | | 1/1990 | Sugimoto et al. ............... 514/212 |

FOREIGN PATENT DOCUMENTS

| 24 29 253 | 1/1976 | (DE) | ................. 544/318 |
| 2 005 134 | 10/1970 | (DE) | ................. 544/352 |
| 0468187 | 1/1992 | (EP) | ................. 514/331 |
| 0487071 | 5/1992 | (EP) | ................. 514/331 |
| 0 154 969 | 9/1985 | (EP) | ................. 544/158 |
| 0 366 511 | 5/1990 | (EP) | ................. 544/351 |
| 0 049 203 | 4/1982 | (EP) | ................. 548/415 |
| 5297952 | 8/1977 | (JP) | ................. 514/331 |
| 597185 | 1/1984 | (JP) | ................. 514/331 |

OTHER PUBLICATIONS

Chemical Abstracts, vol. 93, No. 21, 1980, Columbus, Ohio, US.
Chemical Abstracts, vol. 94, No. 9, 1981, Columbus, Ohio, US.
Chemical Abstracts, vol. 112, No. 7, 1990, Columbus, Ohio US.
Eur. J. Med. Chem.—Chimia Therapeutica. vol. 11, No. 1, 1976, pp. 33–42.
Eur. J. Med. Chem.—Chimia Therapeutica. vol. 13, No. 3, 1978, pp. 223–227.
Eur. J. Med. Chem. vol. 25, 1990, pp. 361–368.
V. Dauksas et al., "Synthesis and antiinflammatory activity of acyl–substituted benzoxa– and benzodioxaheterocycles and their acyclic analogs", Chem. Abstr., 107, 190332h (1987).
S. A. Siphar, "1,4–Benzodioxans", Chem. Abstr., 70, 106531j, (1969).
V. Dauksas et al., "1,4–Benzodioxan ketones. V. 6–Ethyl–7–(ω–dialkyl–aminoacyl)–1,4–benzodioxans and their cyclic analogs", Chem. Abstr., 67, 54087k, (1967).
Thompson et al. "New England Journal of Medicine" vol. 323 pp. 445–448 and 691 (1960).*
Han et al. "Eur. J. Med. Chem." vol. 27, pp. 673–687 (1992).*
Davis et al. "New England Journal of Medicine" vol. 327, pp. 1253–1259 (1992).*
Brufani et al. "Pharmacology Biochemistry and Behavior" vol. 26 pp. 625–629 (1987).*
Summers "New England Journal of Medicine" vol. 315, (1986) pp. 1241–1245.*
Shutske et al. "J. Med Chem." vol. 32, 1989 pp. 1805–1813.*

* cited by examiner

*Primary Examiner*—Bruck Kifle
(74) *Attorney, Agent, or Firm*—Foley & Lardner

(57) ABSTRACT

A compound of the formula:

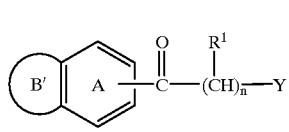

[I']

wherein ring A is an optionally substituted benzene ring; ring B' is an optionally substituted non-aromatic heterocyclic ring having, the same or different, two or more hetero atoms; $R^1$ is a hydrogen atom or an optionally substituted hydrocarbon group, which may be different from one another in the repetition of n; Y is an optionally substituted amino group or an optionally substituted N-containing saturated heterocyclic group; n denotes an integer of 1 to 10, provided that when the ring B' is a 5- to 7-membered ring, the ring B' contains at least one nitrogen atom as hetero atom and n denotes an integer of 2 to 10, or a salt thereof. The compounds and salts thereof have an excellent cholinesterase inhibitory activity and antidepressant activity, and are useful as therapeutic and/or prophylactic medicaments of senile dementia.

21 Claims, No Drawings

HETEROCYCLIC COMPOUNDS, THEIR PRODUCTION AND USE

FIELD OF THE INVENTION

This invention relates to novel heterocyclic compounds and salts thereof, and to pharmaceutical preparations. More particularly, the present invention relates to a cholinesterase inhibitor, especially to a therapeutic and/or prophylactic agent for senile dementia, Alzheimer and so on, novel heterocyclic compounds as active ingredients and salts thereof, to methods for preparing the same and to intermediate products thereof.

BACKGROUND OF THE INVENTION

With an increasing number of elderly people, there have been proposed various compounds having therapeutic and/or prophylactic actions on senile dementia. Among these compounds, there has been found a therapeutic/prophylactic action in physostigmine, a naturally-occurring cholinesterase inhibitor (International Journal of Clinical Pharmacology, Therapy and Toxicology, Vol. 29, No.1, p.23–37(1991) etc.). Physostigmine has, however, such defects as a relatively short duration of the action and high toxicity.

On the other hand, various heterocyclic compounds have been suggested as synthetic medicines. For example, EP-A-0,378,207, U.S. Pat. No. 4,849,431 corresponding to JPA-62(1987)-234065, U.S. Pat. No. 4,895,841 corresponding to JPA-64(1989)-79151, JPA-2(1990)-169569 and EP-A-0,468,187 disclose cholinesterase inhibitors having nitrogen-containing heterocyclic ring (hereinafter referred to as N-containing heterocyclic ring). U.S. Pat. No. 4,064,255 corresponding to JPA-52(1977)-72829 and U.S. Pat. No. 4,208,417 corresponding to JPA-55(1980)-9070 respectively disclose heterocyclic compounds used as an antidepressant or antianxiety drugs.

More particularly, EP-A-0,378,207 discloses a cyclic amino compound of the following formula or salts thereof:

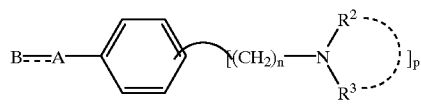

wherein B stands for an optionally substituted saturated or unsaturated 5- to 7-membered azaheterocyclic group; A represents a bond, an alkylene group or an alkenylene group which may be substituted with a hydrocarbon residue, an oxo group or hydroxyl group; ═══represents a single bond or double bond (provided that A represents a bond, ═══represents a single bond); $R_2$ and $R_3$ independently represent a hydrogen atom or an optionally substituted hydrocarbon residue (provided that they are not H at the same time) or may form a cyclic amino group taken together with the adjacent nitrogen atom; n denotes 0, 1 or 2; and p notes 1 or 2, or salts thereof.

Practically it discloses a compound of the following formula among others:

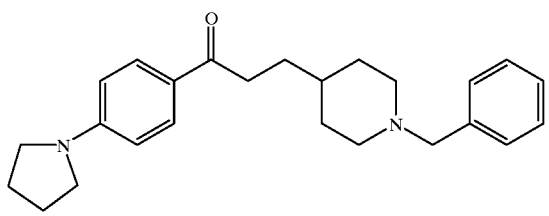

In U.S. Pat. No. 4,849,431 corresponding to JPA-62(1987)-234065, there are disclosed piperidine derivatives of the following formula or pharmaceutically acceptable salts thereof:

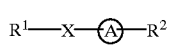

wherein $R^1$ represents a monovalent group derived from a member selected from optionally substituted benzene, pyridine, pyrazine, indole, anthraquinone, quinoline, optionally substituted phthalimide, homophtalimide, pyridine carboxylimide, pyridine-N-oxide, pyrazine carboxylimide, naphthalenedicarboxylimide, optionally substituted quinazolinedione, 1,8-naphthalimide, bicyclo[2.2.2]oct-5-ene-2,3-dicarboxylimide and pyromellylimide;

X represents a group of the formula —$(CH_2)_m$— (wherein m denotes an integer of 0 to 7); a group of the formula —$O(CH_2)_n$—; a group of the formula —$S(CH_2)_n$—; a group of the formula —$NH(CH_2)_n$—; a group of the formula —$SO_2NH(CH_2)_n$—; a group of the formula —NH—CO—$(CH_2)_n$—; a group of the formula —NH$(CH_2)_n$—CO—; a group of the formula —COO$(CH_2)_n$—; a group of the formula —$CH_2NH(CH_2)_n$—; a group of the formula —CO—$NR^3$—$(CH_2)_n$—(in the definition of X, in all formula, n each denotes an integer of 0 to 7; and $R^3$ represents a lower alkyl group or benzyl group); a group of the formula —O—$CH_2CH_2CH(CH_3)$—; a group of the formula —O—$CH(CH_3)CH_2CH_2$—; a group of the formula —O—$CH_2CH_2CH$═; or a group of the formula —O—$CH_2CH(OH)CH_2$—; Ring A represents a group of the formula

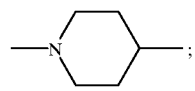

a group of the formula

a group of the formula

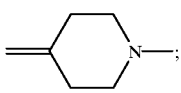

a group of the formula

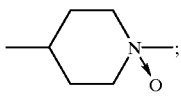

$R^2$ represents a hydrogen atom, a lower alkyl group, an optionally substituted benzyl group, optionally substituted benzoyl group, pyridyl group, 2-hydroxyethyl group, pyridylmethyl group or group of the formula:

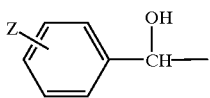

(wherein Z represents a halogen atom).

Practically, there is disclosed a compounds of the following formula among them:

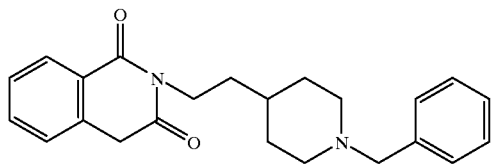

U.S. Pat. No. 4,895,841 corresponding to JPA-64(1989)-79151, and JPA-2(1990)-169569 disclose a cyclic amine derivative of the following general formula or pharmaceutically acceptable salts thereof:

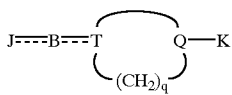

wherein

J represents
  (a) optionally substituted groups shown as follows; (1) a phenyl group, (2) a pyridyl group, (3) a pyrazyl group, (4) a quinolyl group, (5) a cyclohexyl group, (6) a quinoxalyl group or (7) a furyl group,
  (b) a mono- or di-valent group selected from the following groups which may be substituted on the phenyl group; (1) an indanyl group, (2) an indanonyl group, (3) an indenyl group, (4) an indenonyl group, (5) an indandionyl group, (6) a tetranonyl group, (7) a benzsperonyl group, (8) an indanolyl group or (9) a group of the formula:

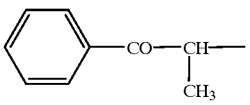

(c) a monovalent group derived from a cyclic amide compound,
(d) a lower alkyl group or
(e) a group of the formula $R^1$—CH=CH— (wherein $R^1$ represents a hydrogen atom or a lower alkoxycarbonyl group);

B represents a group of the formula —$(C(R^2)H)_n$—; a group of the formula —CO—$C(R^2)H)_n$—; a group of the formula —$NR^2$—$(C(R^2)H)_n$— (wherein $R^2$ represents a hydrogen atom, a lower alkyl group, an acyl group, a lower alkylsulfonyl group, an optionally substituted phenyl group or benzyl group); a group of the formula —CO—$NR^4$—$C(R^2)H)_n$— (wherein $R^4$ represents a hydrogen atom, a lower alkyl group or a phenyl group), a group of the formula —CH=CH—$(C(R^2)H)_n$—; a group of the formula —O—COO—$(C(R^2)H)_n$—; a group of the formula —O—CO—NH—$(C(R^2)H)_n$—; a group of the formula —NH—CO—$(C(R^2)H)_n$—; a group of the formula —$CH_2$—CO—NH—$(C(R^2)H)_n$—; a group of the formula —CO—NH—$(C(R^2)H)_n$—; a group of the formula —C(OH)H—$(C(R^2)H)_n$— (in the above formulae, n denotes 0 or an integer of 1 to 10, $R^2$ represents a hydrogen atom or a methyl group in the form of an alkylene group of the formula —$(C(R^2)H)_n$— which is unsubstituted or having one or more than one methyl group); a group of the formula=$(CH—CH=CH)_b$— (wherein b denotes an integer of 1 to 3); a group of the formula=CH—$(CH_2)_c$— (wherein c denotes 0 or an integer of 1 to 9); a group of the formula=$(CH—CH)_d$= (wherein d denotes 0 or an integer of 1 to 5); a group of the formula=CO—CH=CH—$CH_2$—; a group of the formula —CO—$CH_2$—C(OH)H—$CH_2$—; a group of the formula —$C(CH_3)$H—CO—NH—$CH_2$—; a group of the formula —CH=CH—CO—NH—$(CH_2)_2$—; a group of the formula —NH—; a group of the formula —O—; a group of the formula —S—; a dialkylaminoalkylcarbonyl group or a lower alkoxycarbonyl group;

T represents a nitrogen atom or a carbon atom;

Q represents a nitrogen atom, a carbon atom or a group of the formula >N→O;

K represents a hydrogen atom, an optionally substituted phenyl group, an arylalkyl group optionally substituted with a phenyl group, a cinnamyl group optionally substituted with phenyl group, a lower alkyl group, a pyridylmethyl group, a cycloalkylalkyl group, an adamantanemethyl group, a furylmethyl group, a cycloalkyl group, a lower alkoxycarbonyl group or an acyl group; q denotes an integer of 1 to 3 ═ and represents a single bond or a double bond, and a cholinesterase inhibitor containing the above mentioned compounds.

A practical embodiment thereof is the following compound.

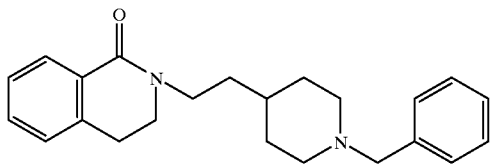

EP-A-0,468,187 discloses a cyclic amide compound of the formula:

wherein $R^1$ represents a group derived from an optionally substituted cyclic amide compound; n denotes an integer of 0 to 10; and Z represents a formula:

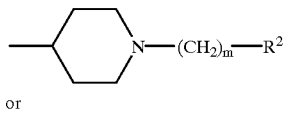
(1)

or

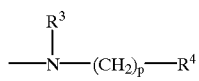
(2)

wherein $R^2$ represents an aryl group, a substituted aryl group, a cycloalkyl group or a heterocyclic group; m denotes an integer of 1 to 6; $R^3$ represents a hydrogen atom or a lower alkyl group; $R^4$ represents an aryl group, a substituted aryl group, a cycloalky group or a heterocyclic group; p denotes an integer of 1 to 6, provided that when the cyclic amide compound is quinazolinone or quinazolinedione derivative, $R^2$ and $R^4$ are neither an aryl group nor a substituted aryl group.

Practically, it discloses a compound of the following formula among them:

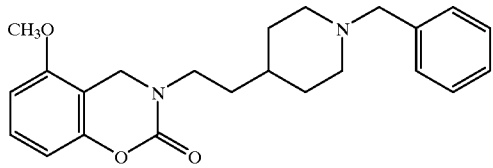

U.S. Pat. No. 4,064,255 corresponding to JPA-52(1977)-72829 discloses a pharmaceutical composition used for treatment of pathological conditions caused by disturbances in serotonin systems, which comprises a compound of the formula or pharmaceutically acceptable salts thereof:

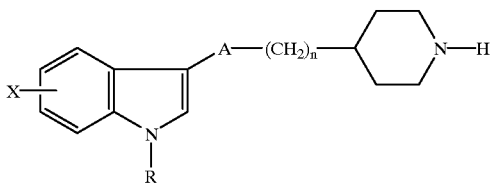

wherein R represents a hydrogen atom, a $C_{1-4}$ alkyl group or a aralkyl group having 1 or 2 carbon atom(s) in the alkyl moiety thereof; X represents a hydrogen atom or a halogen atom, an alkyl, an alkoxy or an alkylthio group each optionally having 1 to 4 carbon atoms, trifluoromethyl, nitro, hydroxy or unsubstituted amino group, or an amino group substituted with one or two alkyl, acyl or alkylsulfonyl group; A represents a group —CO—, or a group —CH$_2$—; and n represents 0, 1 or 2.

U.S. Pat. No. 4,208,417 corresponding to JPA-55(1980)-9070 discloses medicinally active compounds having an affinity for the binding site of $^3$H-diazepam which are indole derivatives having the general formula:

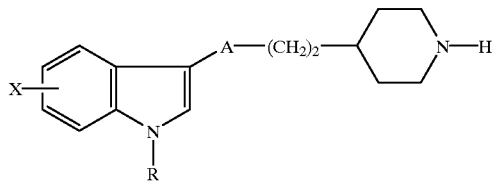

wherein R is a hydrogen atom, a $C_{1-4}$ alkyl group or an aralkyl group whose alkyl moiety has 1 or 2 carbon atoms; X is a hydrogen atom, a halogen atom, an alkyl group, an alkoxy group or an alkylthio group whose alkyl moiety has 1 to 4 carbon atoms; A sands for —CO— or —CH$_2$—; and n denotes 1 or 2.

Further, WO91/03243 discloses a compound, which is used as a psychopharmaceutical, of the following general formula or pharmaceutically acceptable salts thereof:

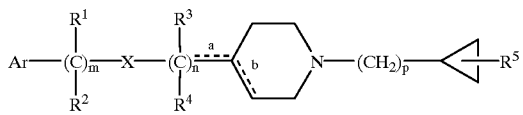

wherein m denotes 0 to 3; n denotes 0 to 3; m and n are not 0 simultaneously; p denotes 0 to 3; X represents O, S, SO, SO$_2$, NR$^6$, CR$^7$R$^8$, CO or CHOH; $R^1$, $R^3$ and $R^7$ each represents a hydrogen atom, a $C_{1-5}$ alkyl group, a halogen atom, a group of the formula NR$^{10}$R$^{11}$, OH, COOH, a $C_{2-6}$ alkoxycarbonyl group, CN, Ar, a $C_{1-5}$ alkoxy group or a $C_{1-5}$ alkylthio group; $R^2$, $R^4$ and $R^8$ each represents a hydrogen atom, a $C_{1-5}$ alkyl group, a $C_{2-6}$ alkoxycarbonyl, CN, a $C_{1-5}$ alkoxy group or Ar$^1$; when X is O, S, SO, SO$_2$ or NR$^6$, $R^1$, $R^2$, $R^3$ and $R^4$ are not a $C_{1-5}$ alkoxy, a $C_{1-5}$ alkylthio, the group NR$^{10}$R$^{11}$ or OH; $R^5$ represents a hydrogen atom, an alkyl group, a halogen atom, OH or an alkenyl group; $R^6$ represents a hydrogen atom, a $C_{1-5}$ alkyl group or Ar$^1$; Ar and Ar$^1$ each represents a naphthyl group, a pyridyl group, a pyrimidyl group, an indolyl group, a quinolinyl group, an isoquinolinyl group or a phenyl group, and these groups being optionally substituted with a $C_{1-3}$ alkyl group, a $C_{1-3}$ alkoxy group, a $C_{1-3}$ haloalkyl group having 1 to 7 halogen atoms, SH, a S(O)$_t$—$C_{1-3}$ alkyl group (wherein t denotes 1, 2 or 3), a $C_{2-6}$ dialkylamino group, a halogen atom, a $C_{1-3}$ alkylamino group, NH$_2$, CN, NO$_2$, SO$_3$H, a tetrazole group, COOH, a $C_{2-6}$ alkoxycarbonyl, CONH$_2$, SO$_2$NO$_2$, COR$^9$, CONR$^{12}$R$^{13}$, SO$_2$NR$^{12}$R$^{13}$, Ar$^2$, OAr$^2$ or SAr$^2$; Ar$^2$ represents a naphthyl or a phenyl group, and these groups optionally substituted with a $C_{1-3}$ alkyl group, a $C_{1-3}$ haloalkyl group having 1 to 7 halogen atoms, a $C_{1-3}$ alkoxy group, a halogen atom or a $C_{1-3}$ alkylthio group; $R^9$, $R^{10}$, $R^{11}$, $R^{12}$ and $R^{13}$ each represents a halogen atom, a $C_{1-5}$ alkyl group or a phenyl group, $R^{10}$ and $R^{11}$ may, taken together, form a $C_{3-6}$ alkylene chain and $R^{12}$ and $R^{13}$ may, taken together, form a $C_{3-6}$ alkylene chain; a or b represents a single bond or double bond, both are not simultaneously a double bond.

Furthermore, various condensed heterocyclic derivatives containing a hetero atom such as a nitrogen, an oxygen, a sulfur atom and the like have been suggested and their biological activity and pharmacological actions have been reported. Cholinesterase inhibitory action and actions as therapeutic/prophylactic agents of senile dementia, however, have not been disclosed therein.

More definitely, Chem. Abstr., 107, 190332h(1987) discloses that a compound of the following general formula has an anti-inflammatory action:

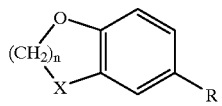

wherein R is Ac, COEt, COPr, COCHMe$_2$, CO(CH$_2$)$_2$Cl, CO(CH$_2$)$_3$Cl, COCH$_2$NMe$_2$, CO(CH$_2$)$_2$NMe$_2$, CO(CH$_2$)$_3$NMe$_2$, and salts thereof or R is COCH=CHPh; X is CH$_2$, or O; and n is 1, 2 or 3 (wherein Ac represents an acetyl group; Et, Pr and Me represent a ethyl group, a propyl group, a methyl group respectively; and Ph represents a phenyl group).

Chem. Abstr., 89, 36594y(1978) discloses that the compound of the general formula has an antispasmic action, depressing action of arterial blood pressure and a local anesthetic action:

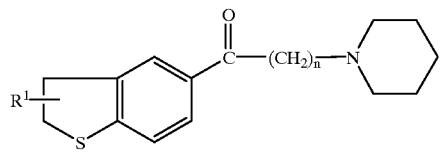

wherein $R^1$ is H or Me; n is 2 or 3.

Journal of Pharmacology, 97, 540(1977) discloses that a compound of the following general formula has an antidepressant action:

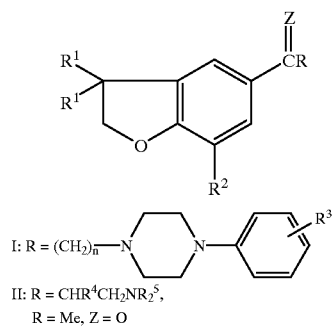

I: R = (CH$_2$)$_n$—
II: R = CHR$^4$CH$_2$NR$^5_2$,
R = Me, Z = O wherein $R^1$ is H or Me; $R^2$ is H, Cl or Me; $R^3$ is H, F, Me, OMe or Cl; n is 1, 2 or 3; Z is O, OH or H (for compound I) or $R^2$ is H or Cl; $R^4$ is H or Me; $NR^5_2$ is NMe$_2$, morpholino or piperidino (for compound II).

EP-163,537 discloses that a compound of the general formula has a muscular relaxant action:

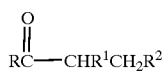

wherein R is a 4-cycloalkylphenyl group, 3,4-methylenedioxyphenyl group, 2,3-dihydro-5-benzofuranyl group; $R^1$ is an alkyl group, a cycloalkyl group or a cyclopentylmethyl group; $R^2$ is an optionally substituted pyrrolidino, piperidino, hexahydro-1H-azepine-1-yl or octahydro-1-azocinyl group.

Chem. Abstr., 91,211631y (1979) discloses that a compound of the following formula is synthesized as a derivative of cystisine, which is an alkaloid having an anticholinergic action:

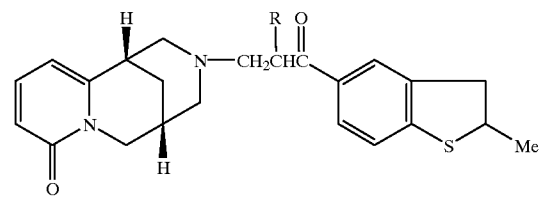

wherein R is H or Me.

Helvetica Chimica Acta, 51, 1616(1968) discloses compounds of the following formula (A) and (B):

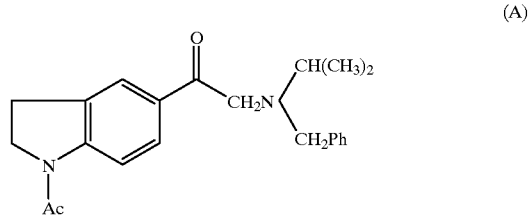

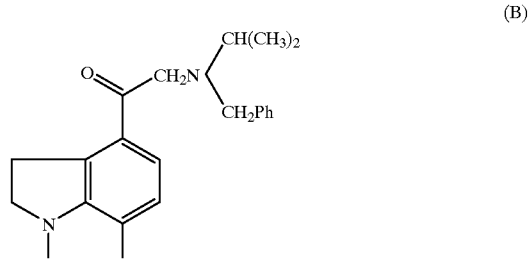

as an intermediate products for synthesizing alkanolamines of the following formula (C), which is an agent acting on the sympathetic nervous system:

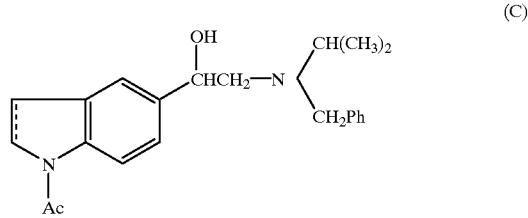

JPA-52(1977)-97952 discloses a compound of the formula:

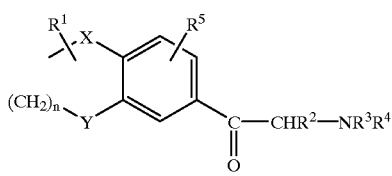

wherein $R^1$ is an alkyl group or a phenyl group; $R^2$ is a $C_{1-3}$ alkyl group; $R^3$ is an alkenyl group, an alkynyl group, a cycloalkyl group or an alkyl group; $R^4$ is H or an alkyl group; $NR^3R^4$ is a morpholino group, a pyrrolidino group or a piperidino group; $R^5$ is H or a $C_{1-3}$ alkyl group; $R^6$ is H or an acyl group; n is 1 to 3; X is S, O or NH; and Y is $CH_2$ or S, as an intermediate product of aminoalchol derivatives of the following formula, which has a depressing action, an antispasmodic action, a vasodilating action and a calmative action:

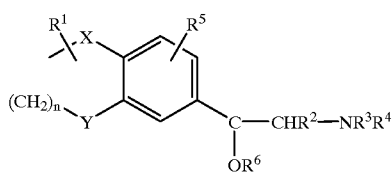

wherein each symbol has the same meaning as defined above.

In JPA-59(1984)-7185 there is disclosed that a 1,5-benzoxepine derivative of the following formula or acid adducts thereof has a depressing action of blood pressure:

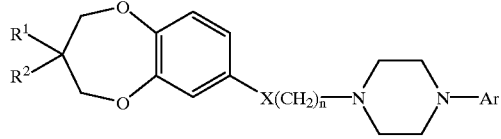

wherein $R^1$ represents a hydrogen atom or an alkyl group having 1 to 3 carbon atom(s); $R^2$ shows a $C_{1-3}$ alkyl group;

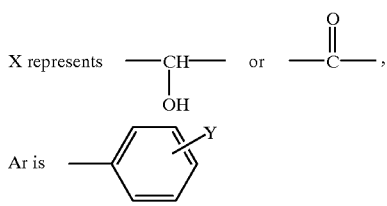

wherein Y represents a hydrogen atom, —$OCH_3$, a halogen atom or

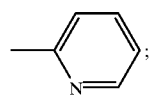

n denotes an integer of 1 to 5.

Chem. Abstr., 70, 106531j (1969) corresponding to FR-M3,635 discloses, for example, a compound of the formula:

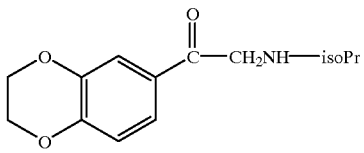

as an intermediate product of 1,4-benzodioxane derivatives of the formula:

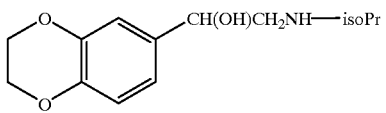

which is an agent acting on the sympathetic nervous system.

Further, Chem. Abstr., 67, 54087k (1967), 68, 105121x (1968), 75, 88548s (1971), 76, 153682t (1972) disclose methods for preparing 1,4-benzoxane derivatives of the formula:

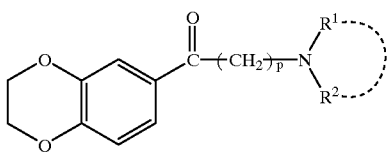

wherein

represents an optionally substituted amino group or a cyclic amino group, and p denotes 1 or 2.

However, in these literatures, there is no disclosure of biological activity, pharmacological action and the like.

SUMMARY OF THE INVENTION

In the present situation that patients of senile dementia have become increased, the development excellent therapeutic and/or prophylactic agent, having stronger action and longer action and less toxicity than the compounds already known to have therapeutic and/or prophylactic efficacy on senile dementia, has been desired.

Accordingly, it is an object of the present invention to provide novel heterocyclic compounds or salts thereof which are useful as a cholinesterase inhibitor, especially as an agent of preventing senile dementia.

It is another object of the present invention to provide heterocyclic compounds and salts thereof having a stronger and longer cholinesterase inhibitory action and a less toxicity than compounds already known to have a therapeutic and/or prophylactic efficacy on senile dementia.

It is yet another object of the invention to provide methods of producing the heterocyclic compounds or salts thereof useful as a cholinesterase inhibitor.

It is a further object of the present invention to provide intermediate products useful for producing the heterocyclic compounds or salts thereof.

A still further object of the invention is to provide a cholinesterase inhibitor containing a heterocyclic compound having a cholinesterase inhibitory activity.

A yet further object of the present invention is to provide a pharmaceutical composition for an agent for a disease caused by acetylcholinesterase activity.

The present invention further discloses a method of treating a disease caused by acetylcholinesterase activity and use of the heterocyclic compound or a salt thereof as a cholinesterase inhibitor.

The present invention was accomplished by investigating various aspects of heterocyclic compounds including novel compounds in biological activity and pharmacological action and by finding that the compounds having structural characteristics in bicyclic-heteroyclic group wherein the heterocyclic ring containing, the same or different, two or more hetero atoms, condensed on the benzene ring have unexpectedly excellent cholinesterase inhibitory activity and antidepressant activity, thus being useful as therapeutic and/or prophylactic agents for senile dementia. Based on these structural characteristics, these compounds show above-mentioned excellent actions.

More specifically, the present invention relates to;

(1) heterocyclic compounds of the formula:

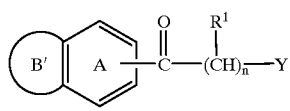
[I']

wherein ring A is an optionally substituted benzene ring; ring B' is an optionally substituted non-aromatic heterocyclic ring having, the same or different, two or more hetero atoms; $R^1$ is a hydrogen atom or an optionally substituted hydrocarbon group, which may be different from one another in the repetition of n; Y is an optionally substituted amino group or an optionally substituted N-containing saturated heterocyclic group; n denotes an integer of 1 to 10, provided that when ring B' is a 5- to 7-membered ring, ring B' contains at least one nitrogen atom as hetero atoms and n denotes an integer of 2 to 10, or a salt thereof.

The present invention also provides (2) a compound of the formula:

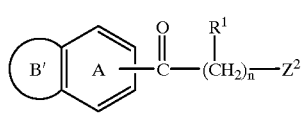
[IV]

wherein ring A, ring B' $R^1$ and n have the same meanings as defined above; and $Z^2$ represents a leaving group, or a salt thereof.

The present invention further provides (3) a method of producing the compound [I'], which comprises reacting a compound of the formula:

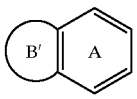
[II]

wherein ring A and ring B' are as defined above, or a salt thereof, with a compound of the formula:

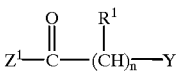
[III]

wherein $Z^1$ is a leaving group; $R^1$, Y and n are as defined above, or a salt thereof.

Furthermore, the present invention provides (4) a method of producing a compound of the formula:

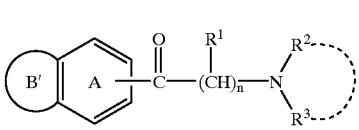
[VI]

wherein $R^2$ and $R^3$ are, the same or different, H, an optionally substituted hydrocarbon group or an optionally substituted acyl group, and $R^2$ and $R^3$ may form an optionally substituted N-containing saturated heterocyclic group; and ring A, ring B', $R^1$ and n are as defined above, or a salt thereof, which comprises reacting a compound of the formula:

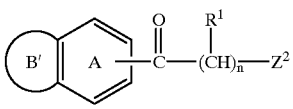
[IV]

wherein $Z^2$ is a leaving group; ring A, ring B', $R^1$ and n are as defined above, or a salt thereof, with a compound of the formula:

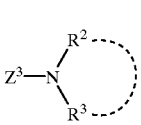
[V]

wherein $Z^3$ is a leaving group which can be left with $Z^2$; $R^2$ and $R^3$ are as defined above, or a salt thereof.

The present invention also provides (5) a cholinesterase inhibitor, which contains a compound of the formula:

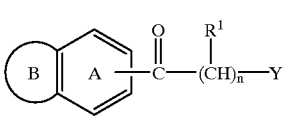
[I]

wherein ring A is an optionally substituted benzene ring; ring B is an optionally substituted non-aromatic heterocyclic ring having independently two or more hetero atoms; $R^1$ is a hydrogen atom or an optionally substituted hydrocarbon group, which may be different from one another in the repetition of n; Y is an optionally substituted amino group or an optionally substituted N-containing saturated heterocyclic group, n denotes an integer of 1 to 10, or a salt thereof.

The present invention further provides (6) a pharmaceutical composition for an agent for a disease caused by acetylcholinesterase activity which contains an effective cholinesterase inhibiting amount of the compound [I] or a salt thereof and a pharmacologically acceptable carrier.

According to the present invention, (7) a pharmaceutical composition of senile dementia and/or Alzheimer's disease containing the compound [I] or a salt thereof is also provided.

The present invention also relates to a method of treating a disease such as senile dementia and/or Alzheimer's disease caused by acetylcholinesterase activity which comprises administering a therapeutically effective amount of the compound [I] or a salt thereof, together with a pharmaceutically acceptable carrier to a mammal suffering from such disease, and use of the compound [I] or a salt thereof as a component in the preparation of a cholinesterase inhibitor.

The compound [I'] or salts thereof of this invention are novel compounds having structural characteristics in that the non-aromatic heterocyclic ring B' containing two or more hetero atoms (e.g. O, S or N) is condensed on the benzene ring A and a substituent

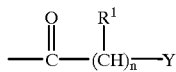

is bonded to the carbon atom of the benzene ring A, and these compounds show excellent therapeutic and/or prophylactic actions for senile dementia due to these characteristics.

DETAILED DESCRIPTION OF THE INVENTION

The groups given in terms of symbols in the above general formulae are respectively described in more detail in the following.

In the above-identified formulae, $R^1$ represents a hydrogen atom or an optionally substituted hydrocarbon group, which may be different from one another in the repetition of n.

Examples of "hydrocarbon group" of "optionally substituted hydrocarbon group" shown by the above-mentioned $R^1$ include a chain-like or cyclic or their combined type $C_{1-18}$ hydrocarbon group.

Examples of the chain-like hydrocarbon group include a straight-chain or branched $C_{1-11}$ alkyl group (e.g. methyl, ethyl, n-propyl, i-propyl, n-butyl, i-butyl, tert-butyl, n-pentyl, n-hexyl, etc.), a straight-chain or branched $C_{2-6}$ alkenyl group (e.g. vinyl, allyl, 2-butenyl, etc.) and a straight-chain or branched $C_{2-6}$ alkynyl group (e.g. propargyl, 2-butynyl, etc.).

As typical examples of the cyclic hydrocarbon group include a $C_{3-7}$ monocyclic cycloalkyl group (e.g. cyclobutyl, cyclopentyl, cyclohexyl, etc.), a $C_{8-14}$ bridge ring saturated hydrocarbon group (e.g. bicyclo[3.2.1]oct-2-yl, bicyclo (3.3.1]non-2-yl, adamantan-1-yl, etc.), a $C_{6-14}$ aryl group (e.g. phenyl group, naphthyl group, etc.) among others.

Examples of hydrocarbon group composed of chain-like and cyclic ones include a $C_{7-18}$ aralkyl group (e.g. phenyl-$C_{1-12}$ alkyl group or naphthyl-$C_{1-8}$ alkyl group such as benzyl, phenylethyl, phenylpropyl, phenylbutyl, phenylpentyl, phenylhexyl, α-naphthylmethyl and the like; a diphenyl-$C_{1-3}$ alkyl group such as diphenylmethyl, diphenylethyl and the like), a $C_{6-14}$ aryl-$C_{2-12}$ alkenyl group (e.g. phenyl-$C_{2-12}$ alkenyl group such as styryl, cinnamyl, 4-phenyl-2-butenyl, 4-phenyl-3-butenyl and the like), a $C_{6-14}$ aryl-$C_{2-12}$ alkynyl group (e.g. phenyl-$C_{2-12}$ alkynyl group such as phenylethynyl, 3-phenyl-2-propinyl, 3-phenyl-1-propinyl and the like), a $C_{3-7}$ cycloalkyl-$C_{1-6}$ alkyl group (e.g. cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl, cycloheptylhexyl, etc.).

The preferred examples of the "hydrocarbon group" shown by $R^1$ include a straight-chain or branched $C_{1-11}$ alkyl group, more preferably a straight-chain or branched $C_{1-7}$ alkyl group (e.g. methyl, ethyl, n-propyl, i-propyl, n-butyl, i-butyl, tert-butyl, n-pentyl, n-hexyl, etc.) or a $C_{7-18}$ aralkyl group, preferably a $C_{7-10}$ aralkyl group (e.g. phenyl-$C_{1-4}$ alkyl group such as benzyl, phenylethyl, phenylpropyl, etc.).

The hydrocarbon group shown by $R^1$ may optionally have substituents, and, as such substituents, use is properly made of those generally used as substituents of hydrocarbon group. As typical examples of such substituents of the above-mentioned $C_{1-11}$ alkyl group, a $C_{2-6}$ alkenyl group, a $C_{2-6}$ alkynyl group, a $C_{3-7}$ monocyclic cycloalkyl group and $C_{8-14}$ bridge ring saturated hydrocarbon group, there may be mentioned groups selected from a halogen atom (e.g. fluorine, chlorine, bromine, iodine), a nitro group, a cyano group, a hydroxyl group, a $C_{1-4}$ alkoxy group (e.g. methoxy, ethoxy, propyloxy, butyloxy, isopropyloxy, etc.), a $C_{1-4}$ alkylthio group (e.g. methylthio, ethylthio, propylthio, etc.), an amino group, a mono- or di-$C_{1-4}$ alkylamino group (e.g. methylamino, ethylamino, propylamino, dimethylamino, diethylamino, etc.), a 5- to 7-membered cyclic amino group which may have, other than carbon atoms and one nitrogen atom, 1 to 3 of nitrogen, oxygen and/or sulfur atoms (e.g. pyrrolidino, piperidino, morpholino, etc.), a $C_{1-4}$ alkyl-carbonylamino group (e.g. acetylamino, propionylamino, butyrylamino, etc.), a $C_{1-4}$ alkylsulfonylamino group (e.g. methylsulfonylamino, ethylsulfonylamino, etc.), a $C_{1-4}$ alkoxy-carbonyl group (e.g. methoxycarbonyl, ethoxycarbonyl, propoxycarbonyl, etc.), a carboxyl group, a $C_{1-6}$ alkyl-carbonyl group (e.g. methylcarbonyl, ethylcarbonyl, propylcarbonyl, etc.), a carbamoyl group, a mono- or di-$C_{1-4}$ alkyl-carbamoyl group (e.g. methylcarbamoyl, ethylcarbamoyl, etc.), a $C_{1-6}$ alkylsulfonyl group (e.g. methylsulfonyl, ethylsulfonyl, propylsulfonyl, etc.). The number of such substituents is about 1 to 5.

Examples of the substituents of $C_{6-14}$ aryl group, a $C_{7-18}$ aralkyl group, a $C_{6-14}$ aryl-$C_{2-12}$alkenyl group, a $C_{6-14}$ aryl-$C_{2-12}$ alkynyl group and $C_{3-7}$ cycloalkyl-$C_{1-6}$ alkyl group shown by $R^1$ include a $C_{1-4}$ alkyl group (e.g. methyl, ethyl, propyl, butyl, etc.), a halogen atom (e.g. fluorine, chlorine, bromine, iodine), a nitro group, a cyano group, a hydroxyl group, a $C_{1-4}$ alkoxy group (e.g. methoxy, ethoxy, propyloxy, butyloxy, isopropyloxy, etc.), a $C_{1-4}$ alkylthio group (e.g. methylthio, ethylthio, propylthio, isopropylthio, butylthio, etc.), an amino group, a mono- or di-$C_{1-4}$ alkylamino group (e.g. methylamino, ethylamino, propylamino, dimethylamino, diethylamino, etc.), a 5- to 7-membered cyclic amino group which may have, other than carbon atoms and one nitrogen atom, 1 to 3 of nitrogen, oxygen and/or sulfur atoms as hetero atoms (e.g. pyrrolidino, piperidino, morpholino, etc.), a $C_{1-4}$ alkyl-carbonylamino group (e.g. acetylamino, propionylamino, butyrylamino, etc.), an aminocarbonyloxy group, a mono- or di-$C_{1-4}$ alkylamino-carbonyloxy group (e.g. methylaminocarbonyloxy, ethylaminocarbonyloxy, dimethylaminocarbonyloxy, diethylaminocarbonyloxy, etc.), a $C_{1-4}$ alkylsulfonylamino group (e.g. methylsulfonylamino, ethylsulfonylamino, propylsulfonylamino, etc.), a $C_{1-4}$ alkoxy-carbonyl group (e.g. methoxycarbonyl, ethoxycarbonyl, propoxycarbonyl, isobutoxycarbonyl, etc.), a carboxyl group, a $C_{1-6}$ alkylcarbonyl group (e.g. methylcarbonyl, ethylcarbonyl, butylcarbonyl, etc.), a $C_{3-7}$ cycloalkyl-carbonyl group (e.g. cyclohexylcarbonyl, etc.), a carbamoyl group, a mono- or di-$C_{1-4}$ alkyl-carbamoyl group (e.g. methylcarbamoyl, ethylcarbamoyl, propylcarbamoyl, butylcarbamoyl, diethylcarbamoyl, dibutylcarbamoyl, etc.), a $C_{1-6}$ alkylsulfonyl group (e.g. methylsulfonyl, ethylsulfonyl, propylsulfonyl, etc.), a $C_{3-7}$ cycloalkylsulfonyl (e.g. cyclopentylsulfonyl, cyclohexylsulfonyl, etc.) as well as phenyl, naphthyl, a mono- or di-phenyl-$C_{1-3}$ alkyl group (e.g. benzyl, diphenylmethyl, etc.), a phenoxy group, a benzoyl group, a phenoxycarbonyl group, a benzylcarbonyl group, a phenyl-$C_{1-4}$ alkyl-carbamoyl group, a phenylcarbamoyl group, a phenyl-$C_{1-4}$ alkyl-carbonylamino, benzoylamino group, a phenyl-$C_{1-4}$ alkylsulfonyl group, a phenylsulfonyl group, a phenyl-$C_{1-4}$ alkylsulfinyl group, a phenyl-$C_{1-4}$ alkylsulfonylamino group or a phenylsulfonylamino group.

As examples of substituents of each phenyl group or naphthyl group of the above-mentioned substituents, there may be mentioned 1 to 4 groups selected from a $C_{1-4}$ alkyl group such as methyl, ethyl, propyl, butyl, isopropyl and the like, a $C_{1-4}$ alkoxy group such as methoxy, ethoxy, n-propyloxy, i-propyloxy, n-butoxy, etc., a halogen atom such as fluorine, chlorine, bromine and iodine, a hydroxyl group, a benzyloxy group, an amino group, a mono- or di-$C_{1-4}$ alkylamino group as described above, a nitro group, a $C_{1-6}$ alkyl-carbonyl group as described above, a benzoyl group and so on.

The number of substituents which may optionally be substituted on these $C_{6-14}$ aryl group, a $C_{7-18}$ aralkyl group, a $C_{6-14}$ aryl-$C_{2-12}$ alkenyl group, a $C_{6-14}$ aryl-$C_{2-12}$ alkynyl group and $C_{3-7}$ cycloalkyl-$C_{1-6}$ alkyl group is suitably about 1 to 5.

The benzene ring represented by ring A is condensed on the ring B or ring B' and may have substituents besides the group of the formula:

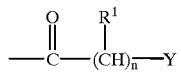

Such substituents include, for example, 1 to 3 substituents similar to those mentioned in $C_{6-14}$ aryl group, a $C_{7-18}$ aralkyl group, a $C_{6-14}$ aryl-$C_{2-12}$ alkenyl group, a $C_{6-14}$ aryl-$C_{2-12}$ alkynyl group and $C_{3-7}$ cycloalkyl-$C_{1-6}$ alkyl group of $R^1$. Preferred examples of the substituents are, among others, a halogen atom such as fluorine, chlorine, etc., a halogeno-$C_{1-3}$ alkyl group such as trifluoromethyl, etc., a $C_{1-3}$ alkyl group such as methyl, etc. and a $C_{1-3}$ alkoxy group such as methoxy, etc. Especially, halogen atoms such as fluorine, chlorine, etc. are preferable.

Ring B represents a non-aromatic heterocyclic ring having the same or different, two or more hetero atoms, and may have substituent(s).

As ring B, there may be mentioned, for example, a 4- to 14-membered ring, preferably, a 5- to 9-membered ring. Typical examples of the hetero atoms, for example, include 2 or 3 atoms selected from nitrogen atom, oxygen atom, sulfur atom, etc. Practically preferred is a 5- to 9-membered non-aromatic heterocyclic ring having, the same or different, two hetero atoms. Especially, a non-aromatic heterocyclic ring having, other than carbon atoms and one nitrogen atom, one hetero atom selected from nitrogen, oxygen and sulfur atom is frequently utilized. Namely, typical examples of bicyclic condensed heterocyclic ring shown by the formula:

include benzoxazole such as 2,3-dihydrobenzoxazole, etc.; benzothiazole such as 2,3-dihydrobenzothiazole, etc.; benzimidazole such as 2,3-dihydro-1H-benzimidazole, etc.; benzoxazine such as 3,4-dihydro-1H-2,1-benzoxazine, 3,4-dihydro-1H-2,3-benzoxazine, 3,4-dihydro-2H-1,2-benzoxazine, 3,4-dihydro-2H-1,4-benzoxazine, 3,4-dihydro-2H-1,3-benzoxazine, 3,4-dihydro-2H-3,1-benzoxazine, etc.; benzothiazine such as 3,4-dihydro-1H-2,1-benzothiazine, 3,4-dihydro-1H-2,3-benzothiazine, 3,4-dihydro-2H-1,2-benzothiazine, 3,4-dihydro-2H-1,4-benzothiazine, 3,4-dihydro-2H-1,3-benzothiazine, 3,4-dihydro-2H-3,1-benzothiazine, etc.; benzodiazine such as 1,2,3,4-tetrahydrocinnoline, 1,2,3,4-tetrahydrophthalazine, 1,2,3,4-tetrahydroquinazoline, 1,2,3,4-tetrahydroquinoxaline, etc.; benzoxathiin such as 3,4-dihydro-1,2-benzoxathiin, 3,4-dihydro-2,1-benzoxathiin, 2,3-dihydro-1,4-benzoxathiin, 1,4-dihydro-2,3-benzoxathiin, 4H-1,3-benzoxathiin, 4H-3,1-benzoxathiin, etc.; benzodioxin such as 3,4-dihydro-1,2-benzodioxin, 2,3-dihydro-1,4-benzodioxin, 1,4-dihydro-2,3-benzodioxin, 4H-1,3-benzodioxin, etc.; benzodithiin such as 3,4-dihydro-1,2-benzodithiin, 2,3-dihydro-1,4-benzodithiin, 1,4-dihydro-2,3-benzodithiin, 4H-1,3-benzodithiin, etc.; benzoxazepine such as 2,3,4,5-tetrahydro-1,2-benzoxazepine, 2,3,4,5-tetrahydro-1,3-benzoxazepine, 2,3,4,5-tetrahydro-1,4-benzoxazepine, 2,3,4,5-tetrahydro-1,5-benzoxazepine, 1,3,4,5-tetrahydro-2,1-benzoxazepine, 1,3,4,5-tetrahydro-2,3-benzoxazepine, 1,3,4,5-tetrahydro-2,4-benzoxazepine, 1,2,4,5-tetrahydro-3,1-benzoxazepine, 1,2,4,5-tetrahydro-3,2-benzoxazepine, 1,2,3,5-tetrahydro-4,1-benzoxazepine, etc.; benzothiazepine such as 2,3,4,5-tetrahydro-1,2-benzothiazepine, 2,3,4,5-tetrahydro-1,4-benzothiazepine, 2,3,4,5-tetrahydro-1,5-benzothiazepine, 1,3,4,5-tetrahydro-2,1-benzothiazepine, 1,3,4,5-tetrahydro-2,4-benzothiazepine, 1,2,4,5-tetrahydro-3,1-benzothiazepine, 1,2,4,5-tetrahydro-3,2-benzothiazepine, 1,2,3,5-tetrahydro-4,1-benzothiazepine, etc.; benzodiazepine such as 2,3,4,5-tetrahydro-1H-1,2-benzodiazepine, 2,3,4,5-tetrahydro-1H-1,3-benzodiazepine, 2,3,4,5-tetrahydro-1H-1,4-benzodiazepine, 2,3,4,5-tetrahydro-1H-1,5-benzodiazepine, 2,3,4,5-tetrahydro-1H-2,3-benzodiazepine, 2,3,4,5-tetrahydro-1H-2,4-benzodiazepine, etc.; benzodioxepin such as 4,5-dihydro-1,3-benzodioxepin, 4,5-dihydro-3H-1,2-benzodioxepin, 2,3-dihydro-5H-1,4-benzodioxepin, 3,4- dihydro-2H-1,5-benzodioxepin, 4,5-dihydro-1H-2,3-benzodioxepin, 1,5-dihydro-2,4-benzodioxepin, etc.; benzodithiepin such as 4,5-dihydro-1H-2,3-benzodithiepin, 1,5-dihydro-2,4-benzodithiepin, 3,4-dihydro-2H-1,5-benzodithiepin, 2,3-dihydro-5H-1,4-benzodithiepin, etc.; benzoxazocine such as 3,4,5,6-tetrahydro-2H-1,5-benzoxazocine, 3,4,5,6-tetrahydro-2H-1,6-benzoxazocine, etc.; benzothiazocine such as 3,4,5,6-tetrahydro-2H-1,5-benzothiazocine, 3,4,5,6-tetrahydro-2H-1,6-benzothiazocine, etc.; benzodiazocine such as 1,2,3,4,5,6-hexahydro-1,6-benzodiazocine, etc.; benzoxathiocine such as 2,3,4,5-tetrahydro-1,6-benzoxathiocine, etc.; benzodioxocin such as 2,3,4,5-tetrahydro-1,6-benzodioxocin, etc.; benzotrioxepin such as 1,3,5-benzotrioxepin, 5H-1,3,4-benzotrioxepin, etc.; benzoxathiazepine such as 3,4-dihydro-1H-5,2,1-benzoxathiazepine, 3,4-dihydro-2H-5,1,2-benzoxathiazepine, 4,5-dihydro-3,1,4-benzoxathiazepine, 4,5-dihydro-3H-1,2,5-benzoxathiazepine, etc.; benzoxadiazepine such as 2,3,4,5-tetrahydro-1,3,4-benzoxadiazepine, etc.; benzothiadiazepine such as 2,3,4,5-tetrahydro-1,3,5-benzothiadiazepine, etc.; benzotriazepine such as 2,3,4,5-tetrahydro-1H-1,2,5-benzotriazepine, etc.; benzoxathiepin such as 4,5-dihydro-1,3,2-benzoxathiepin, 4,5-dihydro-1H-2,3-benzoxathiepin, 3,4-dihydro-2H-1,5-benzoxathiepin, 4,5-dihydro-3H-1,2-benzoxathiepin, 4,5-dihydro-3H-2,1-benzoxathiepin, 2,3-dihydro-5H-1,4-benzoxathiepin, 2,3-dihydro-5H-4,1-benzoxathiepin and the like.

The preferred examples of the condensed heterocyclic rings are shown as follows:

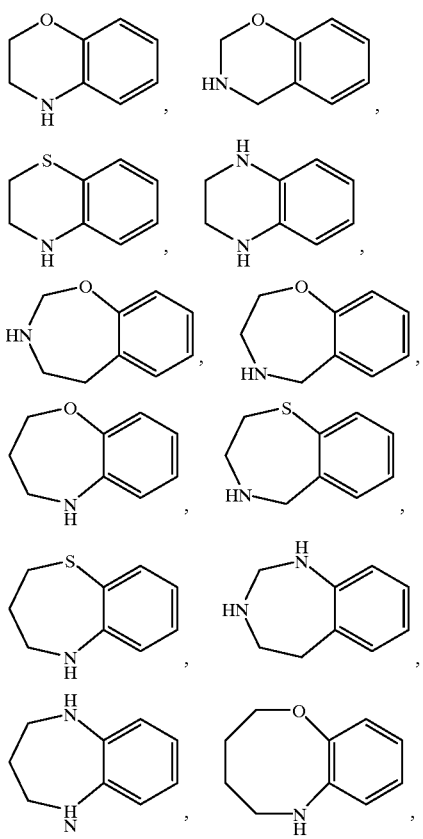

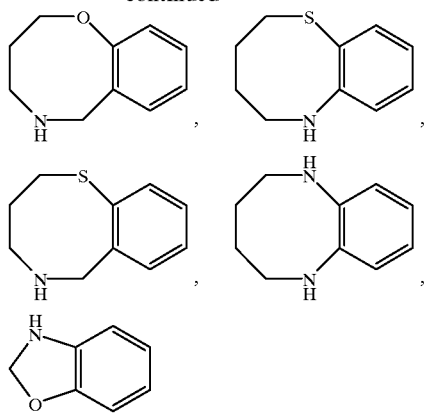

Ring B' represents an optionally substituted nonaromatic heterocyclic ring including, the same or differint, two or more hetero atoms. Provided that when the ring B' represents a 5- to 7-membered ring, the ring B' has at least one nitrogen atom as a hetero atom.

As the ring B' there may be mentioned, for example, a 4- to 14-membered ring, preferably 5- to 9-membered ring. As the typical examples of the hetero atoms, there may be mentioned 2 or 3 atoms selected from nitrogen, oxygen, sulfur atoms and so on. The preferred is a 5- to 9-membered non-aromatic heterocyclic ring having, the same or different, two hetero atoms. Especially, a non-aromatic heterocyclic ring having, other than carbon atoms and one nitrogen atom, one hetero atom selected from nitrogen, oxygen and sulfur atoms is frequently utilized.

More specifically, preferred examples of bicyclic condensed heterocyclic ring shown by the formula:

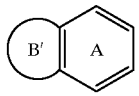

include benzoxazole such as 2,3-dihydrobenzoxazole, etc.; benzothiazole such as 2,3-dihydrobenzothiazole, etc.; benzimidazole such as 2,3-dihydro-1H-benzimidazole, etc.; benzoxazine such as 3,4-dihydro-1H-2,1-benzoxazine, 3,4-dihydro-1H-2,3-benzoxazine, 3,4-dihydro-2H-1,2-benzoxazine, 3,4-dihydro-2H-1,4-benzoxazine, 3,4-dihydro-2H-1,3-benzoxazine, 3,4-dihydro-2H-3,1-benzoxazine, etc.; benzothiazine such as 3,4-dihydro-1H-2,1-benzothiazine, 3,4-dihydro-1H-2,3-benzothiazine, 3,4-dihydro-2H-1,2-benzothiazine, 3,4-dihydro-2H-1,4-benzothiazine, 3,4-dihydro-2H-1,3-benzothiazine, 3,4-dihydro-2H-3,1-benzothiazine, etc.; benzodiazine such as 1,2,3,4-tetrahydrocinnoline, 1,2,3,4-tetrahydrophthalazine, 1,2,3,4-tetrahydroquinazoline, 1,2,3,4-tetrahydroquinoxaline, etc.; benzoxazepine such as 2,3,4,5-tetrahydro-1,2-benzoxazepine, 2,3,4,5-tetrahydro-1,3-benzoxazepine, 2,3,4,5-tetrahydro-1,4-benzoxazepine, 2,3,4,5-tetrahydro-1,5-benzoxazepine, 1,3,4,5-tetrahydro-2,1-benzoxazepine, 1,3,4,5-tetrahydro-2,3-benzoxazepine, 1,3,4,5-tetrahydro-2,4-benzoxazepine, 1,2,4,5-tetrahydro-3,1-benzoxazepine, 1,2,4,5-tetrahydro-3,2-benzoxazepine, 1,2,3,5-tetrahydor-4,1-benzoxazepine, etc.; benzothiazepine such as 2,3,4,5-tetrahydro-1,2-benzothiazepine, 2,3,4,5-tetrahydro-1,4-benzothiazepine, 2,3,4,5-tetrahydro-1,5-benzothiazepine, 1,3,4,5-tetrahydro-2,1-benzothiazepine, 1,3,4,5-tetrahydro-2,4-benzothiazepine, 1,2,4,5-tetrahydro- 3,1-benzothiazepine, 1,2,4,5-tetrahydro-3,2-benzothiazepine, 1,2,3,5-tetrahydro-4,1-benzothiazepine, etc.; benzodiazepine such as 2,3,4,5-tetrahydro-1H-1,2-benzodiazepine, 2,3,4,5-tetrahydro-1H-1,3-benzodiazepine, 2,3,4,5-tetrahydro-1H-1,4-benzodiazepine, 2,3,4,5-tetrahydro-1H-1,5-benzodiazepine, 2,3,4,5-tetrahydro-1H-2,3-benzodiazepine, 2,3,4,5-tetrahydro-1H-2,4-benzodiazepine, etc.; benzoxazocine such as 3,4,5,6-tetrahydro-2H-1,5-benzoxazocine, 3,4,5,6-tetrahydro-2H-1,6-benzoxazocine, etc.; benzothiazocine such as 3,4,5,6-tetrahydro-2H-1,5-benzothiazocine, 3,4,5,6-tetrahydro-2H-1,6-benzothiazocine, etc.; benzodiazocine such as 1,2,3,4,5,6-hexahydro-1,6-benzodiazocine, etc.; benzoxathiocin such as 2,3,4,5-tetrahydro-1,6-benzoxathiocin, etc.; benzodioxocin such as 2,3,4,5-tetrahydro-1,6-benzodioxocin, etc.; benzoxathiazepine such as 3,4-dihydro-1H-5,2,1-benzoxathiazepine, 3,4-dihydro-2H-5,1,2-benzoxathiazepine, 4,5-dihydro-3,1,4-benzoxathiazepine, 4,5-dihydro-3H-1,2,5-benzoxathiazepine, etc.; benzoxadiazepine such as 2,3,4,5-tetrahydro-1,3,4-benzoxadiazepine, etc.; benzothiadiazepine such as 2,3,4,5-tetrahydro-1,3,5-benzothiadiazepine, etc.; benzotriazepine such as 2,3,4,5-tetrahydro-1H-1,2,5-benzotriazepine, etc.; and the like.

Typically preferred examples of the condensed heterocyclic rings are shown as follows:

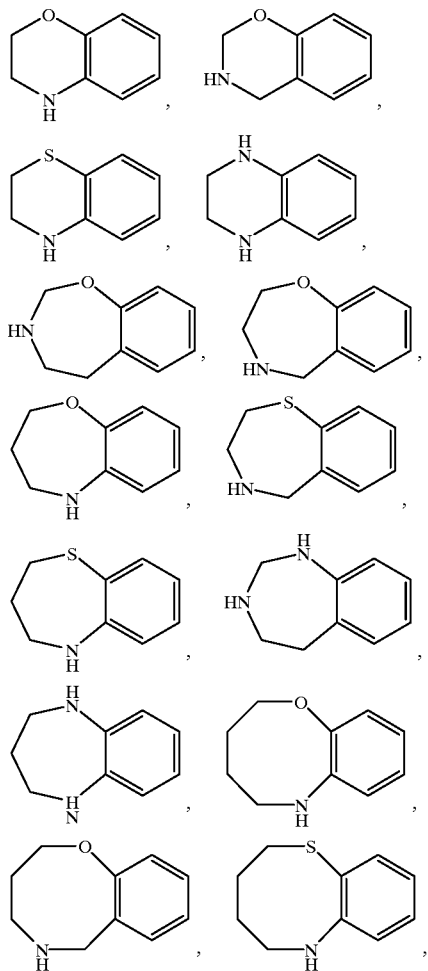

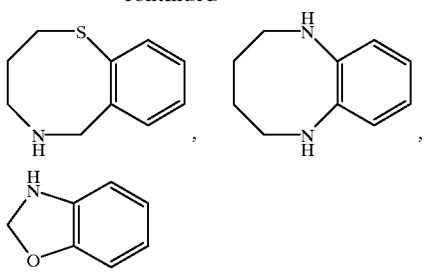

The ring B and ring B' may have substituents on optional carbon atoms thereof. The examples of the substituents include those selected from a halogen atom (e.g. fluorine, chlorine, bromine, iodine), a nitro group, a cyano group, an oxo group, a thioxo group, a hydroxyl group, a $C_{1-4}$ alkoxy group (e.g. methoxy, ethoxy, propyloxy, butyloxy, isopropyloxy, etc.), a $C_{1-4}$ alkylthio group (e.g. methylthio, ethylthio, propylthio, etc.), an amino group, a mono- or di-$C_{1-4}$ alkylamino group (e.g. methylamino, ethylamino, propylamino, dimethylamino, diethylamino, etc.), a 5- to 7-membered cyclic amino group which may have, other than carbon atoms and one nitrogen atom, 1 to 3 of hetero atoms selected from nitrogen, oxygen, sulfur atoms and the like (e.g. pyrrolidino, piperidino, morpholino, thiomorpholino, etc.), a $C_{1-4}$ alkyl carbonylamino group (e.g. acetylamino, propionylamino, butyrylamino, etc.), a $C_{1-4}$ alkylsulfonylamino group (e.g. methylsulfonylamino, ethylsulfonylamino, etc.), a $C_{1-4}$ alkoxy-carbonyl group (e.g. methoxycarbonyl, ethoxycarbonyl, propoxycarbonyl, etc.), a carboxyl group, a $C_{1-6}$ alkyl-carbonyl group (e.g. methylcarbonyl, ethylcarbonyl, propylcarbonyl, etc.), a carbamoyl group, a mono- or di-$C_{1-4}$ alkyl-carbamoyl group (e.g. methylcarbamoyl, ethylcarbamoyl, etc.), a $C_{1-6}$ alkylsulfonyl group (e.g. methylsulfonyl, ethylsulfonyl, propylsulfonyl, etc.) and so on. The number of the substituents which may be substituted on the carbon atoms of the ring B and ring B' is about 1 to 5.

Further, when the ring B and ring B' have nitrogen atom as a ring constituting atom, the nitrogen atom may have a substituent. Namely, the ring B and ring B' may have the following constituting unit:

$$>N-R^6$$

wherein $R^6$ represents a hydrogen atom, an optionally substituted hydrocarbon group or an optionally substituted acyl group.

As the optionally substituted hydrocarbon group shown by $R^6$, there may be mentioned, for example, an optionally substituted hydrocarbon group referring to the above mentioned $R^1$. Among these groups, for example, a $C_{1-7}$ alkyl group (e.g. methyl, ethyl, n-propyl, i-propyl, n-butyl, i-butyl, tert-butyl, n-pentyl, n-hexyl, n-heptyl, etc.) or a $C_{7-10}$ aralkyl group (e.g. phenylmethyl, phenylethyl, phenylpropyl, phenylbutyl, etc.) which may be substituted with substituents selected from a $C_{1-4}$ alkyl group (e.g. methyl, ethyl, n-propyl, i-propyl, n-butyl, i-butyl, tert-butyl, etc.), a halogen atom (e.g. fluorine, chlorine, bromine, iodine), a nitro group, a $C_{14}$ alkoxy group (e.g. methoxy, ethoxy, propyloxy, butyloxy, isopropyloxy, etc.) and a hydroxyl group are preferable. Among these groups, $C_{7-10}$ aralkyl group which may be substituted with a $C_{1-4}$ alkyl group, a halogen atom, a nitro group or a $C_{1-4}$ alkoxy group is frequently utilized.

Examples of "acyl group" of "optionally substituted acyl group" shown by $R^6$ include an acyl group constituting a carboxylic acid (e.g. formyl group, a $C_{1-6}$ alkyl-carbonyl group such as acetyl, propionyl, butyryl, etc., or a phenyl-carbonyl group such as benzoyl, etc.), an acyl group constituting a sulfonic acid (e.g. a $C_{1-7}$ alkylsulfonyl group such as methanesulfonyl, ethanesulfonyl, propanesulfonyl, etc., or a phenylsulfonyl group such as benzenesulfonyl, p-toluenesulfonyl, etc.), an acyl group constituting a phosphonic acid (e.g. a $C_{1-7}$ alkylphosphonyl group such as methanephosphonyl, ethanephosphonyl, propanephosphonyl, etc., or a phenylphosphonyl group such as benzenephosphonyl, p-toluenephosphonyl, etc.), a substituted oxycarbonyl group (e.g. a $C_{1-6}$ alkoxy-carbonyl group such as methoxycarbonyl, tert-butoxycarbonyl, etc., or a $C_{7-8}$ aralkyloxy-carbonyl group such as benzyloxycarbonyl, etc.) and the like.

As examples of the substituents of these acyl groups, there may be mentioned 1 to 3, preferably 1 to 2 substituents selected from a halogen atom (e.g. fluorine, chlorine, bromine, iodine), a nitro group, a hydroxyl group, an amino group, a mono- or di-$C_{1-6}$ alkylamino group (e.g. methylamino, ethylamino, dimethylamino, diethylamino, etc.), a $C_{1-4}$ alkoxy group (e.g. methoxy, ethoxy, propoxy, etc.) and so on.

The preferred examples of acyl group shown by $R^6$ include an unsubstituted formyl group and an unsubstituted $C_{1-6}$ alkyl-carbonyl group (e.g. acetyl, propionyl, butyryl, valeryl, caproyl, etc.).

Y represents an optionally substituted amino group or a N-containing saturated heterocyclic group.

As examples of "optionally substituted amino group" represented by Y, there may be mentioned the group shown by the formula:

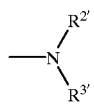

[VII]

wherein $R^{2'}$ and $R^{3'}$ represent, respectively, a hydrogen atom, an optionally substituted hydrocarbon group or an optionally substituted acyl group.

Examples of optionally substituted hydrocarbon group shown by $R^{2'}$ and $R^{3'}$ include those mentioned in reference to the optionally substituted hydrocarbon group of $R^1$.

As the preferred examples of optionally substituted hydrocarbon group shown by $R^{2'}$ and $R^{3'}$, there may be mentioned a straight-chain or branched $C_{1-11}$ alkyl group, preferably a straight-chain or branched $C_{1-7}$ alkyl group (e.g. methyl, ethyl, n-propyl, i-propyl, n-butyl, i-butyl, tert-butyl, n-pentyl, n-hexyl, etc.) or a $C_{7-18}$ aralkyl group (e.g. phenyl-$C_{1-12}$ alkyl such as phenylmethyl, phenylethyl, phenylpropyl, phenylhexyl, or a naphthyl-$C_{1-8}$ alkyl such as α-naphthylmethyl, etc.), preferably a $C_{7-10}$ aralkyl group (e.g. phenylmethyl, phenylethyl, phenylpropyl, etc.).

These hydrocarbon groups such as the above $C_{1-11}$ alkyl group and $C_{7-18}$ aralkyl group shown by $R^{2'}$ and $R^{3'}$ may be substituted with one to three substituents selected from, for example, a halogen atom (e.g. fluorine, chlorine, bromine, iodine), a $C_{1-4}$, alkoxy group (e.g. methoxy, ethoxy, propoxy, etc.), hydroxyl group and the like.

The examples of "acyl group" of "optionally substituted acyl group" shown by $R^{2'}$ and $R^{3'}$ include an acyl group constituting a carboxylic acid (e.g. formyl group, a $C_{1-6}$ alkyl-carbonyl group such as acetyl, propionyl, butyryl, etc., or a phenyl-carbonyl group such as benzoyl, etc.), an acyl group constituting a sulfonic acid (e.g. a.$C_{1-7}$ alkylsulfonyl group such as methanesulfonyl, ethanesulfonyl, propanesulfonyl, etc., or a phenylsulfonyl group such as benzenesulfonyl, p-toluenesulfonyl, etc.), an acyl group constituting a phosphonic acid (e.g. a $C_{1-7}$ alkylphosphonyl group such as methanephosphonyl, ethanephosphonyl, propanephosphonyl, etc., or a phenylphosphonyl group such as benzenephosphonyl, p-toluenephosphonyl, etc.), a substituted oxycarbonyl group (e.g. a $C_{1-6}$ alkoxy-carbonyl group such as methoxycarbonyl, tert-butoxycarbonyl, etc., or a $C_{7-8}$ aralkyloxy-carbonyl group such as benzyloxycarbonyl, etc.). Among them, a $C_{1-6}$ alkoxy-carbonyl group (e.g. methoxycarbonyl, ethoxycarbonyl, t-butoxycarbonyl, etc.) is preferred.

The exemplified substituents of these acyl groups include 1 to 3, preferably 1 to 2 substituents selected from a halogen atom (e.g. fluorine, chlorine, bromine, iodine), a nitro group, a hydroxy group, an amino group, a mono- or di-$C_{1-6}$ alkylamino group (e.g. methylamino, ethylamino, propylamino, hexylamino, dimethylamino, diethylamino, etc.), a $C_{1-4}$ alkoxy group (e.g. methoxy, ethoxy, propoxy, etc.) and the like.

As the preferred examples of $R^{2'}$ and $R^{3'}$, there may be mentioned a straight-chain or branched $C_{1-7}$ alkyl group (e.g. methyl, ethyl, n-propyl, i-propyl, tert-butyl, n-pentyl, n-hexyl, etc.) and a $C_{7-10}$ aralkyl group (e.g. phenylmethyl, phenylethyl, phenylpropyl, etc.). Among them, a $C_{1-3}$ alkyl group such as methyl, ethyl, n-propyl and i-propyl and a $C_{7-10}$ aralkyl group such as phenylmethyl, phenylethyl, phenylpropyl, etc. are preferable.

The examples of "N-containing saturated heterocyclic group" of "optionally substituted N-containing saturated heterocyclic group" shown by Y include a 5- to 9-membered N-containing saturated heterocyclic group which may have, other than carbon atoms and one nitrogen atom, 1 to 3 of hetero atoms selected from nitrogen atoms, oxygen atoms, sulfur atoms, etc. These N-containing saturated heterocyclic groups may be a group having bond on ring-constituting nitrogen atom or on ring-constituting carbon atoms.

As the group having bond on ring-constituting nitrogen atom, there may be mentioned, for example, a group shown by the formula:

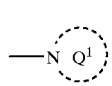

[Y$^1$]

wherein ring $Q^1$ represents a 5- to 9-membered N-containing saturated heterocyclic group which may have, other than carbon atoms and one nitrogen atom, 1 to 2 hetero atoms selected from nitrogen, oxygen, sulfur atoms and so on. Practical examples of these rings are shown as follows:

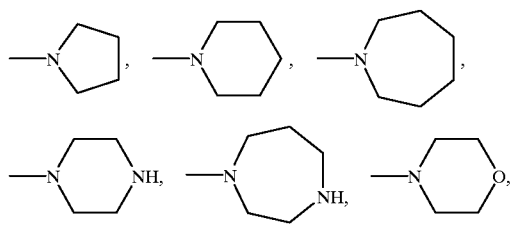

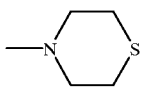

The examples of the group having bond on ring-constituting carbon atoms include a group of the formula:

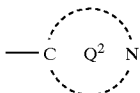

wherein ring $Q^2$ represents a 5- to 9-membered N-containing saturated heterocyclic group which may have, other than carbon atoms and one nitrogen atom, 1 or 2 of nitrogen, oxygen, sulfur atoms, etc. as hetero atoms. As typical examples of these rings, there may be mentioned:

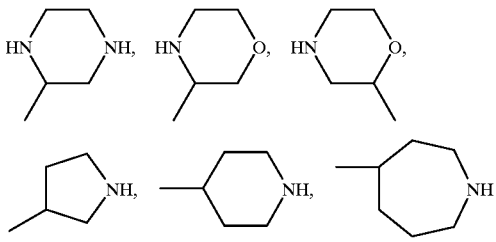

As examples of the substituents which above-mentioned "N-containing saturated heterocyclic group" may have, there may be mentioned those of an optionally substituted hydrocarbon group as described above in $R^1$, an optionally substituted acyl group as described above in $R^{2'}$ and $R^{3'}$, a halogen atom (e.g. fluorine, chlorine, bromine, iodine), a nitro group, a cyano group, an oxo group, a hydroxyl group, a $C_{1-4}$ alkoxy group (e.g. methoxy, ethoxy, propoxy, butoxy, isopropoxy, etc.), a $C_{1-4}$ alkylthio group (e.g. methylthio, ethylthio, propylthio, isopropylthio, butylthio, etc.), an amino group, a mono- or di-$C_{1-4}$ alkylamino group (e.g. methylamino, ethylamino, propylamino, dimethylamino, diethylamino, etc.), a 5- to 7-membered cyclic amino group which may have, other than carbon atoms and one nitrogen atom, 1 to 3 of hetero atoms such as nitrogen, oxygen, sulfur atoms, etc. (e.g. pyrrolidino, piperidino, morpholino, thiomorpholino, etc.), a $C_{1-4}$ alkyl-carbonylamino group (e.g. acetylamino, propionylamino, butyrylamino, etc.), a $C_{1-4}$ alkylsulfonylamino group (e.g. methylsulfonylamino, ethylsulfonylamino, propylsulfonylamino, etc.), a $C_{1-4}$ alkoxy-carbonyl group (e.g. methoxycarbonyl, ethoxycarbonyl, propoxycarbonyl, etc.), a phenyl-$C_{1-4}$ alkyl-oxycarbonyl group (e.g. benzyloxycarbonyl, etc.), a carboxyl group, a $C_{1-6}$ alkyl-carbonyl group (e.g. methylcarbonyl, ethylcarbonyl, propylcarbonyl, butylcarbonyl, etc.), an optionally substituted benzoyl group (e.g. 4-fluorobenzoyl, 3,4-dimethoxybenzoyl, etc.), a carbamoyl group, a mono- or di-$C_{1-4}$ alkyl-carbamoyl group (e.g. methylcarbamoyl, ethylcarbamoyl, etc.), a $C_{1-6}$ alkyl-sulfonyl group (e.g. methylsulfonyl, ethylsulfonyl, propylsulfonyl, etc.) and so on.

The number of substituents which may optionally substituted on the N-containing saturated heterocyclic group is 1 to 5.

Such benzoyl group as described above may be substituted with one to three of substituents selected from a $C_{1-4}$ alkyl group such as methyl, ethyl, etc., a halogen atom such as fluorine, chlorine, bromine and the like, a $C_{1-4}$ alkoxy group such as methoxy, ethoxy, etc., a mono- or di-$C_{1-4}$ alkylamine such as methylamine, diethylamine, etc., a 5- to 7-membered cyclic amino group such as piperidino, morpholino, etc., a nitro group, a hydroxyl group and the like.

Among these substituents, the preferred is an optionally substituted hydrocarbon group as mentioned above in $R^1$ such as a straight-chain or branched $C_{1-11}$ alkyl group, preferably a straight-chain or branched $C_{1-7}$ alkyl group (e.g. methyl, ethyl, n-propyl, i-propyl, n-butyl, i-butyl, tert-butyl, n-pentyl, n-hexyl, etc.), a $C_{7-18}$ aralkyl group (e.g. a phenyl-$C_{1-12}$ alkyl group such as phenylmethyl, phenylethyl, phenylpropyl, phenylbutyl, phenylpentyl, phenylhexyl, etc., or a naphthyl-$C_{1-8}$ alkyl group such as α-naphthylmethyl, etc.), preferably a $C_{7-10}$ aralkyl group (e.g. phenylmethyl, phenylethyl, phenylpropyl, etc.) and a diphenyl-$C_{1-3}$ alkyl group (e.g. diphenylmethyl etc.), which may be substituted with substituents such as a $C_{1-4}$ alkyl group (e.g. methyl, ethyl, propyl, n-butyl, i-butyl, tert-butyl, etc.), a halogen atom (e.g. fluorine, chlorine, bromine, iodine), a nitro group, a $C_{1-4}$ alkoxy group (e.g. methoxy, ethoxy, etc.), a hydroxyl group, and the like. The substitution sites may be on carbon atoms and/or nitrogen atom of the N-containing saturated heterocyclic group.

The N-containing saturated heterocyclic ring represented by Y may be condensed to an other ring such as a benzene ring and so on, and may form, taken together, a bicyclic condensed heterocyclic ring such as a benzoxazepine, and the like.

$R^2$ and $R^3$ each represents a hydrogen atom, an optionally substituted hydrocarbon group or an optionally substituted acyl group, and may form an optionally substituted N-containing saturated heterocyclic group, taken together, with the adjacent nitrogen atom.

As the optionally substituted hydrocarbon group and optionally substituted acyl group shown by $R^2$ and $R^3$, those described in $R^{2'}$ and $R^{3'}$ are utilized.

As the examples above of the optionally substituted N-containing saturated heterocyclic group formed by $R^2$ and $R^3$, taken together, with the adjacent nitrogen atom, there may be mentioned a group having bond on ring-constituting nitrogen atom such as described in [$Y^1$] and the like, among optionally substituted N-containing saturated heterocyclic groups as described in Y.

n denotes an integer of 1 to 10. Provided that when ring B' represents a 5- to 7-membered ring, n denotes an integer of 2 to 10.

The compound of the formula [I'] having ring B' or salts thereof of the present invention involved in the compound of the formula [I] or salts thereof is a novel compound and has more excellent cholinesterase inhibitory activity.

In the above-mentioned formulae, as substituent shown by $R^1$, for example, a hydrogen atom is preferable.

Preferred examples of the benzene ring shown by ring A include an unsubstituted benzene ring.

Examples of the preferred ring B and ring B' include an optionally substituted 5- to 9-membered, more preferably 5- to 7-membered nonaromatic heterocyclic ring having, as hetero atoms, one nitrogen atom and one atom selected from nitrogen, oxygen and sulfur atoms. Among them, a heterocyclic ring having one nitrogen atom and one oxygen atom as hetero atoms is more preferable.

As substituent(s) which the ring B and ring B' may have, (a) an optionally substituted acyl group or an optionally substituted $C_{7-10}$ aralkyl group on the ring-constituting nitrogen atom, and (b) an oxo group on the ring-constituting carbon atom are preferred. More practically, examples of the ring B and ring B' include

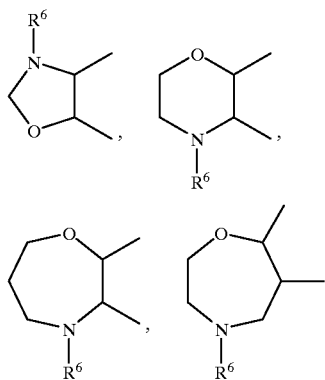

wherein $R^6$ represents a hydrogen atom, an optionally substituted $C_{7-10}$ aralkyl group, or an optionally substituted acyl group, which may be substituted with an oxo group.

The preferred examples of substituent(s) which the acyl group and the $C_{7-10}$ aralkyl group may have, include a halogen atom such as fluorine, chlorine, bromine, etc., a $C_{1-4}$ alkyl group (for example, methyl, ethyl, n-propyl, i-propyl, n-butyl, i-butyl, tert-butyl), a nitro group, a hydroxyl group, a $C_{1-4}$ alkoxy group (e.g. methoxy, ethoxy, propoxy, butoxy, etc.) and the like.

As the preferred examples of Y, there may be mentioned (a) the group of the formula [VII] (especially in case that one of $R^{2'}$ and $R^{3'}$ is a straight-chain or branched $C_{1-7}$ alkyl group (e.g. methyl, ethyl, n-propyl, i-propyl, n-butyl, i-butyl, tert-butyl, n-pentyl, n-hexyl, etc.) and the other is a $C_{7-10}$ aralkyl group (e.g. phenylmethyl, phenylethyl, phenylpropyl, phenylbutyl, etc.) and the like), or (b) a 5- to 9-membered N-containing saturated heterocyclic group which may have, other than carbon atoms and one nitrogen atom, one to two of hetero atoms selected from nitrogen, oxygen and sulfur atoms and which may be substituted with an optionally substituted acyl group or an optionally substituted aralkyl group and the like.

Among them, Y represents preferably a 5- to 9-membered, more preferably a 5- to 7-membered N-containing saturated heterocyclic group represented by the ring $Q^1$ or the ring $Q^2$ which may have, other than carbon atoms and one nitrogen atom, one to two of hetero atoms selected from nitrogen, oxygen and sulfur atoms. These rings may be substituted, preferably on the ring-constituting nitrogen atom, with an optionally substituted acyl group such as formyl or a $C_{1-6}$ alkylcarbonyl, etc., an optionally substituted $C_{7-10}$ aralkyl group and the like.

Typical examples of the group shown by Y, include a ring having the skeleton of pyrrolidine, piperidine, piperazine, morpholine, 1,2,3,4-tetrahydroquinoline, 1,2,3,4-tetrahydroisoquinoline, 2,3,4,5-tetrahydro-1H-1-benzazepine, 2,3,4,5-tetrahydro-1H-2-benzazepine, or 2,3,4,5-tetrahydro-1H-3-benzazepine, which may be substituted with an optionally substituted acyl group, an optionally substituted $C_{7-10}$ aralkyl group and so on are preferable. The practically preferred is a ring having the skeleton of pyrrolidine, piperidine, piperazine or morpholine which may be substituted with an optionally substituted acyl group or an optionally substituted $C_{7-10}$ aralkyl group.

As substituents which these acyl group and $C_{7-10}$ aralkyl group may have, a halogen atom such as fluorine, chlorine, bromine, etc., a $C_{1-4}$ alkyl group (e.g. methyl, ethyl, n-propyl, i-propyl, n-butyl, i-butyl, tert-butyl), a nitro group, a hydroxy group and a $C_{1-4}$ alkoxy group (for example, methoxy, ethoxy, propoxy, butoxy, etc.) and so on are preferable.

n denotes preferably an integer of 2 to 6, more preferably 2 to 4.

The preferred compounds involved in compound of the formula [I] or salts thereof are shown by as follows:

TABLE 1

TABLE 1-continued

| No. | B-A structure | n | Y |
|---|---|---|---|
| 3 | 7-methyl-2,3,4,5-tetrahydro-1,4-benzoxazepine (HN) | 2 | 4-(N-CH₂Ph)piperidin-1-yl |
| 4 | 7-methyl-2,3,4,5-tetrahydro-1,4-benzoxazepine (HN) | 1 | 4-(N-CH₂Ph)piperidin-1-yl |
| 5 | 7-methyl-2,3,4,5-tetrahydro-1,4-benzoxazepine (HN) | 3 | 4-(N-CH₂Ph)piperidin-1-yl |
| 6 | 7-methyl-2,3,4,5-tetrahydro-1,4-benzoxazepine (HN) | 4 | 4-(N-CH₂Ph)piperidin-1-yl |
| 7 | 7-methyl-2,3,4,5-tetrahydro-1,4-benzoxazepine (AcN) | 2 | 4-(N-CH₂Ph)piperidin-1-yl |
| 8 | 7-methyl-2,3,4,5-tetrahydro-1,4-benzoxazepine (EtOC(O)N) | 2 | 4-(N-CH₂Ph)piperidin-1-yl |
| 9 | 7-methyl-2,3,4,5-tetrahydro-1,4-benzoxazepine (PhCH₂N) | 2 | 4-(N-CH₂Ph)piperidin-1-yl |
| 10 | 7-methyl-2,3,4,5-tetrahydro-1,4-benzoxazepine (CH₃N) | 2 | 4-(N-CH₂Ph)piperidin-1-yl |
| 11 | 7-methyl-2,3,4,5-tetrahydro-1,4-benzoxazepine (PhC(O)N) | 2 | 4-(N-CH₂Ph)piperidin-1-yl |

TABLE 1-continued

![structure: B-A-C(=O)-(CH2)n-Y]

| No. | B-A | n | Y |
|---|---|---|---|
| 12 | 2,3,4,5-tetrahydro-1,5-benzoxazepine with 7-OH and 8-CH3 | 2 | 4-methylpiperidine-N-CH2-(3-fluorophenyl) |
| 13 | 2,3,4,5-tetrahydro-1,5-benzoxazepine with 9-OCH3 and 7-CH3 | 2 | 4-methylpiperidine-N-CH2-(4-methoxyphenyl) |

TABLE 2

| No. | B-A | n | Y |
|---|---|---|---|
| 14 | 2,3,4,5-tetrahydro-1,5-benzoxazepine with 9-F and 7-CH3 | 2 | 4-methylpiperidine-N-CH2-(3-methoxyphenyl) |
| 15 | 2,3,4,5-tetrahydro-1,5-benzoxazepine with 9-CH3 and 7-CH3 | 2 | 4-methylpiperidine-N-CH2-(3-hydroxyphenyl) |
| 16 | 2,3,4,5-tetrahydro-1,5-benzoxazepine with 7-CH3 and 6-CH3 | 2 | 4-methylpiperidine-N-CH2Ph |
| 17 | 2,3,4,5-tetrahydro-1,5-benzoxazepine with 7-CH3 and 6-CH3 | 2 | 4-methylpiperidine-N-CH2Ph |

TABLE 2-continued
| No. | (structure with B and A rings) | n | Y |
|---|---|---|---|
| 18 | 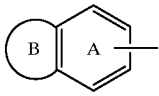 | 2 | 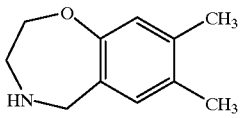 |
| 19 | 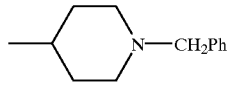 | 2 | 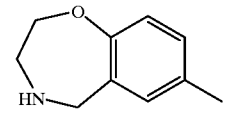 |
| 20 | 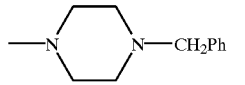 | 2 | 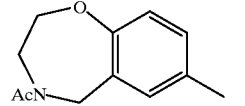 |
| 21 | 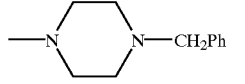 | 2 | 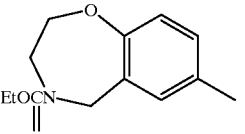 |
| 22 | 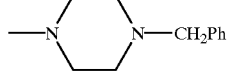 | 2 | 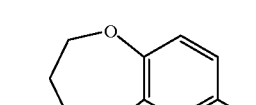 |
| 23 | 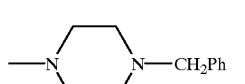 | 1 | 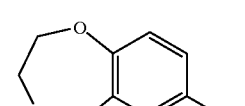 |
| 24 | 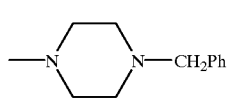 | 3 | 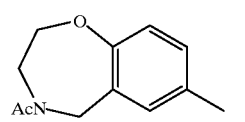 |
| 25 | 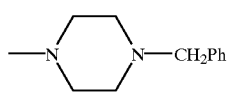 | 4 | 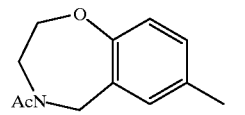 |
| 26 | 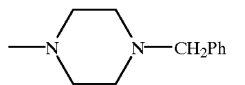 | 2 | 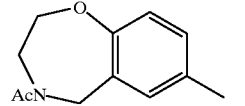 |
| 27 | 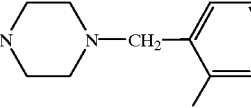 | 2 | 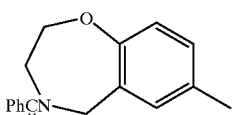 |

TABLE 3

| No. | (structure with B, A rings) | n | Y |
|---|---|---|---|
| 28 | benzoxazepine with 7-methyl, AcN | 2 | 4-methylpiperidine-N-CH₂-(4-nitrophenyl) |
| 29 | benzoxazepine with 7-methyl, EtOC(O)N | 2 | 4-methylpiperidine-N-CH₂-(4-aminophenyl) |
| 30 | benzoxazepine with 7-methyl, PhCH₂N | 2 | 4-methylpiperidine-N-CH₂-(1-naphthyl) |
| 31 | benzoxazepine with 7-methyl, HN | 2 | 4-methyl-N-phenylpiperidine |
| 32 | benzoxazepine with 7-methyl, HN | 2 | 4-methyl-N-(2-pyridyl)piperidine |
| 33 | benzoxazepine with 7-methyl, AcN | 2 | 4-methyl-N-(2-pyrimidinyl)piperidine |
| 34 | benzoxazepine with 7-methyl, AcN | 2 | methylpiperazine-N-CHPh₂ |
| 35 | benzoxazepine with 7-methyl, HN | 2 | N-methylpiperidine |
| 36 | benzoxazepine with 7-methyl, HN | 2 | 4-(4-fluorobenzoyl)-N-methylpiperidine |
| 37 | benzoxazepine with 7-methyl, CH₃N | 2 | 4-(4-chlorophenyl)-4-hydroxy-N-methylpiperidine |

TABLE 3-continued

| No. | (structure with B, A rings) | n | Y |
|---|---|---|---|
| 38 | benzoxazepine, C₃H₇N-CH₂-, methyl | 2 | N-morpholine |
| 39 | benzoxazepine, PhCH₂N-, methyl | 2 | N-thiazolidine |
| 40 | benzoxazepine, PhCH₂CH₂N-, methyl | 2 | —N(CH₃)₂ |
| 41 | benzoxazepine, HN-, methyl | 2 | —N(C₂H₅)₂ |
| 42 | benzoxazepine, HN-, methyl | 5 | —N(C₂H₅)(CH₂Ph) |
| 43 | benzoxazepine, PhCH₂N-, methyl | 5 | —N(C₂H₅)(CH₂Ph) |

TABLE 4

| No. | (structure with B, A rings) | n | Y |
|---|---|---|---|
| 44 | benzoxazepine, HN-, methyl | 6 | —N(C₂H₅)(CH₂Ph) |
| 45 | benzoxazepine, PhCH₂N-, methyl | 6 | —N(C₂H₅)(CH₂Ph) |
| 46 | benzoxazepine, HN-, methyl | 3 | N-phenylpiperazine |

TABLE 4-continued
| No. | 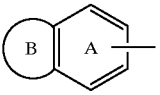 | n | Y |
|---|---|---|---|
| 47 | 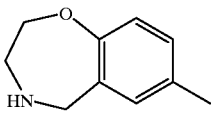 | 3 | 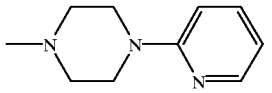 |
| 48 | 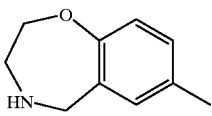 | 3 | 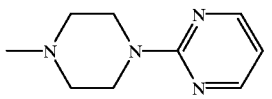 |
| 49 | 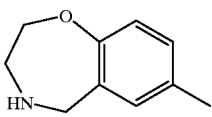 | 3 | 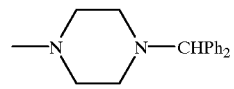 |
| 50 | 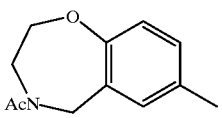 | 3 | 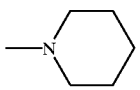 |
| 51 | 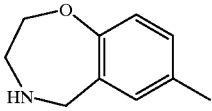 | 3 | 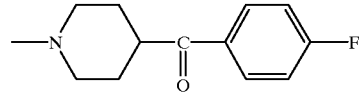 |
| 52 | 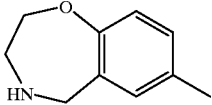 | 3 | 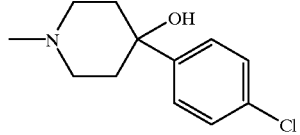 |
| 53 | 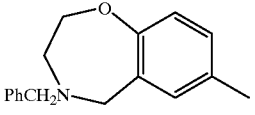 | 3 | 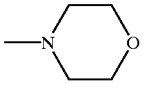 |
| 54 | 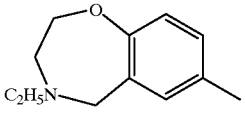 | 3 | 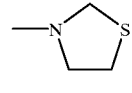 |
| 55 | 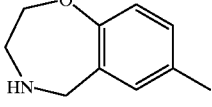 | 3 | —N(CH$_3$)$_2$ |
| 56 | 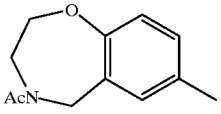 | 3 | —N(C$_2$H$_5$)$_2$ |

TABLE 4-continued
| No. | 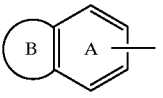 | n | Y |
|---|---|---|---|
| 57 | 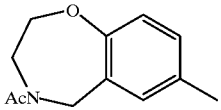 | 5 | 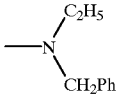 |
| 58 | 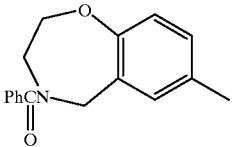 | 5 | 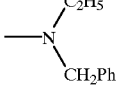 |
| 59 | 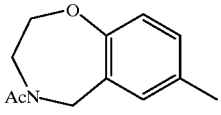 | 6 | 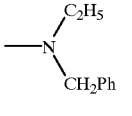 |
TABLE 5
| No. | 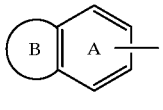 | n | Y |
|---|---|---|---|
| 60 | 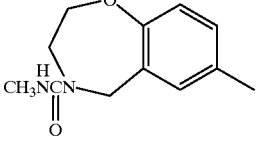 | 6 | 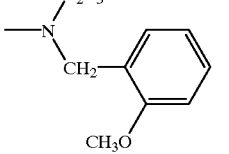 |
| 61 | 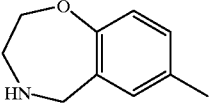 | 2 | 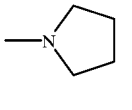 |
| 62 | 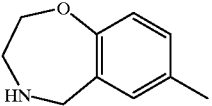 | 2 | 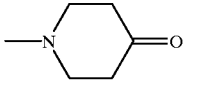 |
| 63 | 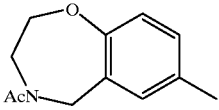 | 2 | 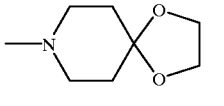 |
| 64 | 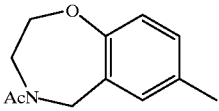 | 2 | 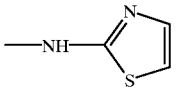 |

TABLE 5-continued

| No. | (B-A structure) | n | Y |
|---|---|---|---|
| 65 | benzoxazepine with EtOCN(=O), 7-methyl | 2 | N-methylazepane |
| 66 | benzoxazepine with AcN, 7-methyl | 2 | 2,3,4,5-tetrahydro-1H-3-benzazepin-3-yl (N-methyl) |
| 67 | benzoxazepine with HN, 7-methyl | 2 | 1,2,3,4-tetrahydroisoquinolin-2-yl (N-methyl) |
| 68 | benzoxazepine with HN, 7-methyl | 2 | —N(piperazine)NAc |
| 69 | benzoxazepine with HN, 7-methyl | 2 | —N(piperazine)N—CHO |
| 70 | benzoxazepine with CH₃N, 7-methyl | 2 | —N(piperazine)N—CH₂CH₂OH |
| 71 | benzoxazepine with PhCH₂N, 7-methyl | 1 | —N(piperazine)N—CHPh₂ |
| 72 | benzoxazepine with HN, 7-methyl | 4 | —N(piperazine)N—CHPh₂ |
| 73 | benzoxazepine with AcN, 7-methyl | 4 | —N(piperazine)N-(pyrimidin-2-yl) |
| 74 | benzoxazepine with HN, 7-methyl | 5 | —N(piperazine)N—CHPh₂ |

TABLE 5-continued

| No. | (B-A structure) | n | Y |
|---|---|---|---|
| 75 | 7-methyl-4-acetyl-2,3,4,5-tetrahydro-1,4-benzoxazepine | 5 | 1-methyl-4-(pyrimidin-2-yl)piperazine |

TABLE 6

| No. | (B-A structure) | n | Y |
|---|---|---|---|
| 76 | 7-methyl-2,3,4,5-tetrahydro-1,4-benzoxazepine (HN) | 1 | —NH—(1-benzylpiperidin-4-yl) |
| 77 | 7-methyl-2,3,4,5-tetrahydro-1,4-benzoxazepine (HN) | 1 | —N(CH₃)—(1-benzylpiperidin-4-yl) |
| 78 | 7-methyl-4-acetyl-2,3,4,5-tetrahydro-1,4-benzoxazepine | 2 | 1-methyl-4-acetyl-homopiperazine |
| 79 | 7-methyl-2,3,4,5-tetrahydro-1,4-benzoxazepine (HN) | 2 | 1-methyl-4-benzyl-homopiperazine |
| 80 | 7-methyl-4-benzyl-2,3,4,5-tetrahydro-1,4-benzoxazepine | 2 | 1-methyl-4-benzyl-homopiperazine |
| 81 | 7-methyl-4-benzyl-2,3,4,5-tetrahydro-1,4-benzoxazepine | 2 | 4-[4-(dimethylamino)benzyl]piperidine |
| 82 | 7-methyl-4-benzyl-2,3,4,5-tetrahydro-1,4-benzoxazepine | 2 | 4-(4-nitrobenzyl)piperidine |
| 83 | 7-methyl-4-benzyl-2,3,4,5-tetrahydro-1,4-benzoxazepine | 2 | 4-(4-acetylbenzyl)piperidine |

TABLE 6-continued

| No. | [B-A structure] | n | Y |
|---|---|---|---|
| 84 | PhCH₂-N-benzoxazepine-methyl | 2 | 4-methylpiperidine-N-CH₂-phenyl-3-OAc |
| 85 | PhCH₂-N-benzoxazepine-methyl | 2 | 4-methylpiperidine-N-CH₂-phenyl-4-Br |
| 86 | PhCH₂-N-benzoxazepine-methyl | 2 | piperazine-N-CH₂-phenyl-4-OH |
| 87 | PhCH₂-N-benzoxazepine-methyl | 2 | piperazine-N-CH(CH₃)-phenyl-4-OH |
| 88 | PhCH₂-N-benzoxazepine-methyl | 2 | piperazine-N-CH₂-phenyl-3-OCH₃ |
| 89 | PhCH₂-N-benzoxazepine-methyl | 2 | piperazine-N-CH₂-phenyl-3,4-di-OCH₃ |
| 90 | PhCH₂-N-benzoxazepine-methyl | 2 | piperazine-N-CH₂-phenyl-3-OCH₃ |

TABLE 7

| No. | [B-A structure] | n | Y |
|---|---|---|---|
| 91 | 2,3-diethyl-5-methyl-benzoxazoline | 2 | 4-methylpiperidine-N-CH₂Ph |
| 92 | 2,3-diethyl-6-methyl-benzoxazoline | 2 | 4-methylpiperidine-N-CH₂Ph |

TABLE 7-continued
| No. | (structure with B/A) | n | Y |
|---|---|---|---|
| 93 | 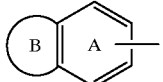 | 2 | 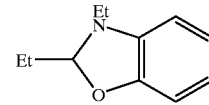 |
| 94 | 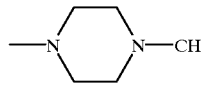 | 2 | 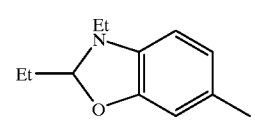 |
| 95 | 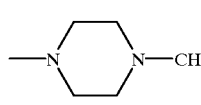 | 2 | 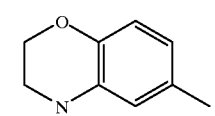 |
| 96 | 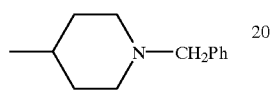 | 2 | 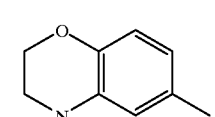 |
| 97 | 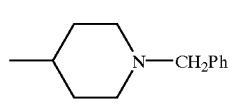 | 2 | 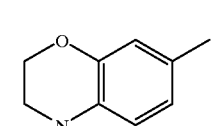 |
| 98 | 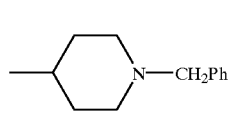 | 2 | 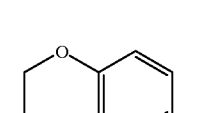 |
| 99 | 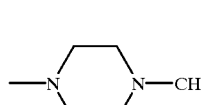 | 2 | 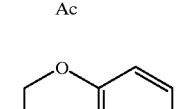 |
| 100 | 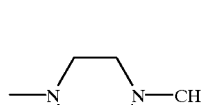 | 2 | 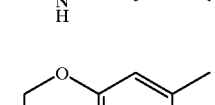 |
| 101 | 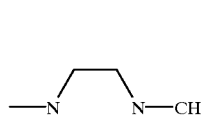 | 2 | 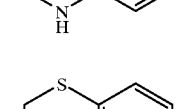 |
| 102 |  | 2 | 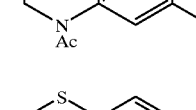 |
| 103 | 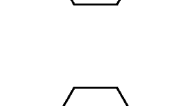 | 2 | 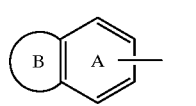 |
TABLE 8
| No. | (structure with B/A) | n | Y |
|---|---|---|---|
| 104 | 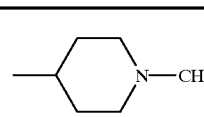 | 2 | 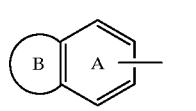 |
| 105 | 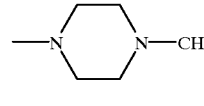 | 2 | 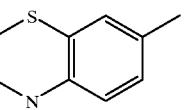 |
| 106 | 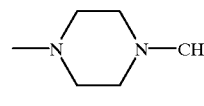 | 2 | 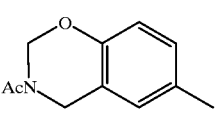 |
| 107 | 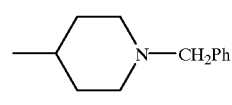 | 2 | 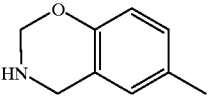 |
| 108 | 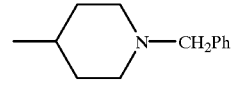 | 2 | 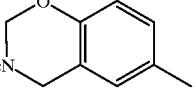 |
| 109 | 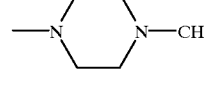 | 2 | 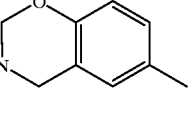 |
| 110 | 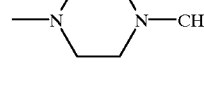 | 2 | 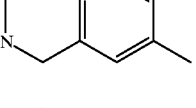 |
| 111 | 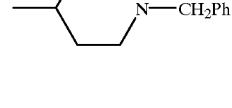 | 2 | 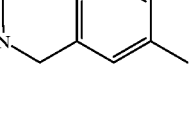 |

TABLE 8-continued

| No. | (structure with B, A rings) | n | Y |
|---|---|---|---|
| 112 | 2H-1,3-benzothiazine, 3-Ac, 6-methyl | 2 | piperazine-N-CH₂Ph |
| 113 | 2H-1,3-benzothiazine, 3-H, 6-methyl | 2 | piperazine-N-CH₂Ph |
| 114 | 2H-1,3-benzoxathiine (O up, S down), 6-methyl | 2 | piperidine-N-CH₂Ph |
| 115 | 2H-1,3-benzoxathiine (S up, O down), 6-methyl | 2 | piperidine-N-CH₂Ph |
| 116 | 2H-1,3-benzodioxine variant (O,S), 6-methyl | 2 | piperazine-N-CH₂Ph |
| 117 | 2H-1,3-benzoxathiine variant, 6-methyl | 2 | piperazine-N-CH₂Ph |
| 118 | 1,2,3,4-tetrahydroquinoxaline, 1,4-diAc, 6-methyl | 2 | piperidine-N-CH₂Ph |
| 119 | 1,2,3,4-tetrahydroquinoxaline, 6-methyl | 2 | piperidine-N-CH₂Ph |

TABLE 9

| No. | (structure with B, A rings) | n | Y |
|---|---|---|---|
| 120 | 1-Ac-4-Ac tetrahydrobenzo[1,4]oxazine variant | 2 | piperazine-N-CH₂Ph |
| 121 | 1,5-benzoxazepine, N-Ac, methyl | 2 | piperidine-N-CH₂Ph |
| 122 | 1,5-benzoxazepine, N-H, methyl | 2 | piperidine-N-CH₂Ph |
| 123 | 1,5-benzoxazepine, N-Ac, methyl | 2 | piperazine-N-CH₂Ph |
| 124 | 1,5-benzoxazepine, N-H, methyl | 2 | piperazine-N-CH₂Ph |
| 125 | 1,5-benzothiazepine, N-Ac, methyl | 2 | piperidine-N-CH₂Ph |
| 126 | 1,5-benzothiazepine, N-H, methyl | 2 | piperidine-N-CH₂Ph |
| 127 | 1,5-benzothiazepine, N-Ac, methyl | 2 | piperazine-N-CH₂Ph |
| 128 | 1,5-benzothiazepine, N-H, methyl | 2 | piperazine-N-CH₂Ph |
| 129 | 2,3,4,5-tetrahydro-1H-1,5-benzodiazepine, 1,5-diAc, methyl | 2 | piperidine-N-CH₂Ph |

TABLE 9-continued

| No. | ![B-A structure] | n | Y |
|---|---|---|---|
| 130 | benzodiazepine with two NH, methyl | 2 | piperidine-N-CH2Ph |

TABLE 10

| No. | ![B-A structure] | n | Y |
|---|---|---|---|
| 131 | benzodiazepine N-Ac, N-Ac, methyl | 2 | piperazine-CH2Ph |
| 132 | benzodiazepine NH, NH, methyl | 2 | piperazine-CH2Ph |
| 133 | benzoxazepine O, HN, methyl | 2 | piperidine-N-CH2Ph |
| 134 | benzoxazepine O, AcN, methyl | 2 | piperidine-N-CH2Ph |
| 135 | benzoxazepine O, HN, methyl | 2 | piperazine-CH2Ph |
| 136 | benzothiazepine S, AcN, methyl | 2 | piperidine-N-CH2Ph |
| 137 | benzothiazepine S, HN, methyl | 2 | piperidine-N-CH2Ph |

TABLE 10-continued

| No. | ![B-A structure] | n | Y |
|---|---|---|---|
| 138 | benzothiazepine S, AcN, methyl | 2 | piperazine-CH2Ph |
| 139 | benzothiazepine S, HN, methyl | 2 | piperazine-CH2Ph |
| 140 | benzodiazepine AcN, AcN, methyl | 2 | piperidine-N-CH2Ph |
| 141 | benzodiazepine HN, HN, methyl | 2 | piperidine-N-CH2Ph |
| 142 | benzodiazepine AcN, AcN, methyl | 2 | piperazine-CH2Ph |
| 143 | benzodiazepine HN, HN, methyl | 2 | piperazine-CH2Ph |

TABLE 11

| No. | ![B-A structure] | n | Y |
|---|---|---|---|
| 144 | benzodiazepine AcN, AcN, methyl | 2 | piperidine-N-CH2Ph |
| 145 | benzodiazepine HN, HN, methyl | 2 | piperidine-N-CH2Ph |

TABLE 11-continued

| No. | [structure A/B] | n | Y |
|---|---|---|---|
| 146 | benzodiazepine with Ac, Ac, CH₃ | 2 | piperazine-N-CH₂Ph |
| 147 | benzodiazepine with H, NH, CH₃ | 2 | piperazine-N-CH₂Ph |
| 148 | benzodiazepine with Ac, Ac, CH₃ | 2 | piperidine-N-CH₂Ph |
| 149 | benzodiazepine with Ac, Ac, CH₃ | 2 | piperidine-N-CH₂Ph |
| 150 | benzodiazepine with Ac, Ac, CH₃ | 2 | piperazine-N-CH₂Ph |
| 151 | benzoxazocine with O, N-Ac, CH₃ | 2 | piperidine-N-CH₂Ph |
| 152 | benzoxazocine with O, NH, CH₃ | 2 | piperidine-N-CH₂Ph |
| 153 | benzoxazocine with O, N-Ac, CH₃ | 2 | piperazine-N-CH₂Ph |
| 154 | benzoxazocine with O, NH, CH₃ | 2 | piperazine-N-CH₂Ph |
| 155 | benzothiazocine with S, N-Ac, CH₃ | 2 | piperidine-N-CH₂Ph |

TABLE 12

| No. | [structure A/B] | n | Y |
|---|---|---|---|
| 156 | benzothiazocine with S, NH, CH₃ | 2 | piperidine-N-CH₂Ph |
| 157 | benzothiazocine with S, N-Ac, CH₃ | 2 | piperazine-N-CH₂Ph |
| 158 | benzothiazocine with S, NH, CH₃ | 2 | piperazine-N-CH₂Ph |
| 159 | benzoxazocine with O, AcN-CH₂, CH₃ | 2 | piperidine-N-CH₂Ph |
| 160 | benzoxazocine with O, HN-CH₂, CH₃ | 2 | piperidine-N-CH₂Ph |
| 161 | benzoxazocine with O, AcN-CH₂, CH₃ | 2 | piperazine-N-CH₂Ph |
| 162 | benzoxazocine with O, HN-CH₂, CH₃ | 2 | piperazine-N-CH₂Ph |

TABLE 12-continued
| No. | | n | Y |
|---|---|---|---|
| 163 | 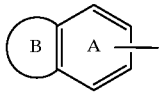 | 2 | 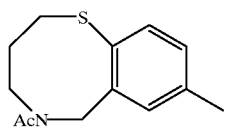 |
| 164 | 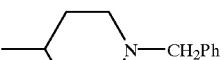 | 2 | 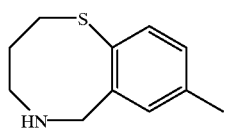 |
| 165 | 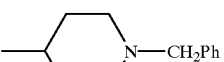 | 2 | 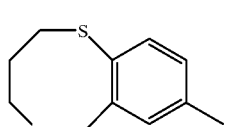 |
| 166 | 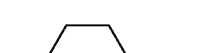 | 2 | 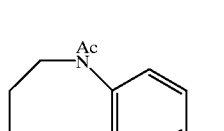 |
TABLE 13
| No. | | n | Y |
|---|---|---|---|
| 167 | 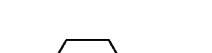 | 2 | 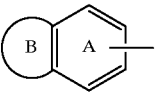 |
| 168 | 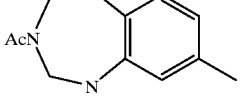 | 2 | 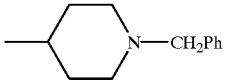 |
| 169 | 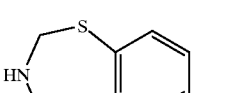 | 2 | 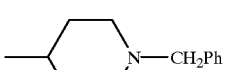 |
TABLE 13-continued
| No. | | n | Y |
|---|---|---|---|
| 170 | 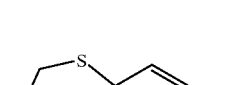 | 2 |  |
| 171 |  | 2 |  |
| 172 |  | 2 | 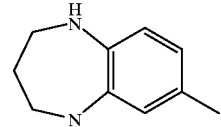 |
| 173 | 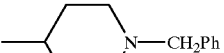 | 2 | 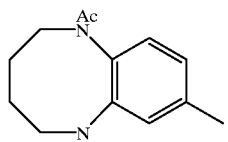 |
| 174 | 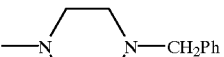 | 2 | 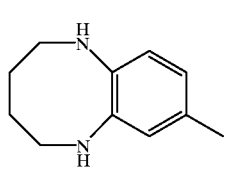 |
| 175 | 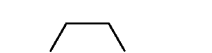 | 2 | 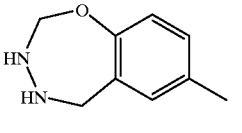 |
| 176 | 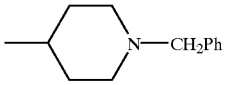 | 2 | 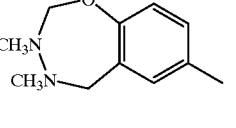 |
| 177 | 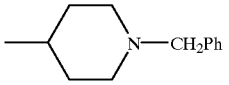 | 2 | 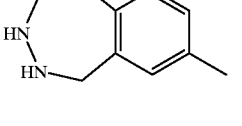 |

TABLE 14
| No. | ![B-A ring] | n | Y |
|---|---|---|---|
| 178 | 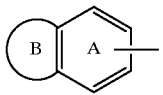 | 2 | 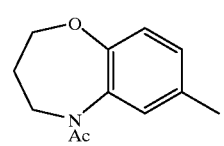 |
| 179 | 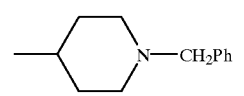 | 2 | 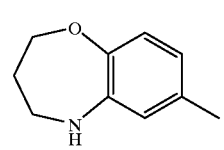 |
| 180 | 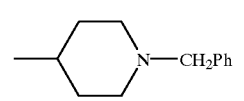 | 2 | 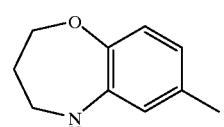 |
| 181 | 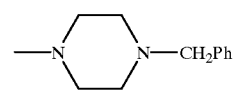 | 2 | 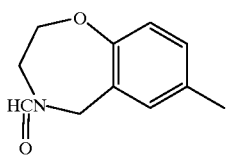 |
| 182 | 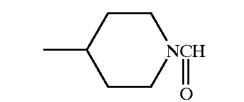 | 2 | 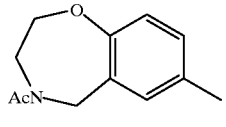 |
| 183 | 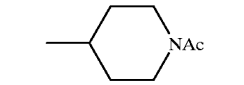 | 2 | 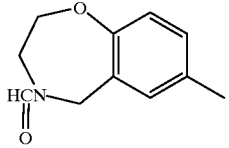 |
| 184 | 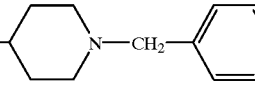 | 2 | 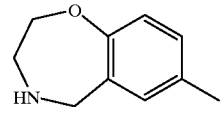 |
| 185 | 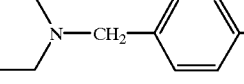 | 2 | 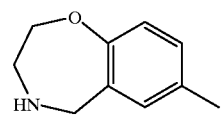 |
| 186 | 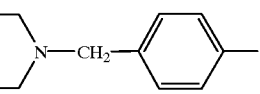 | 2 | 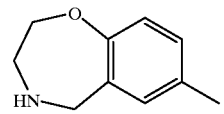 |
| 187 | 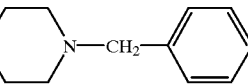 | 2 | 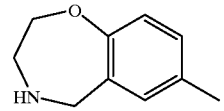 |

TABLE 14-continued
| No. | 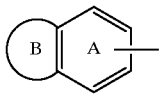 | n | Y |
|---|---|---|---|
| 188 | 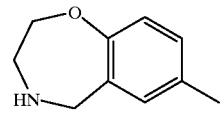 | 2 | 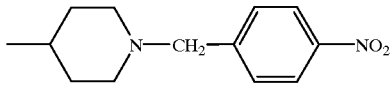 |
| 189 | 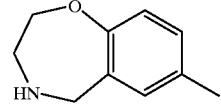 | 2 | 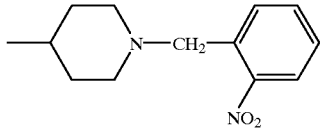 |
| 190 | 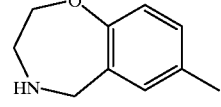 | 2 | 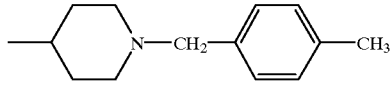 |
TABLE 15
| No. | 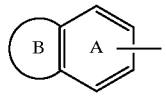 | n | Y |
|---|---|---|---|
| 191 | 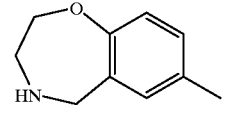 | 2 | 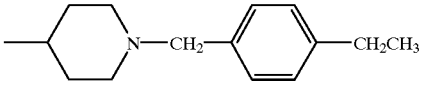 |
| 192 | 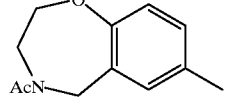 | 2 | 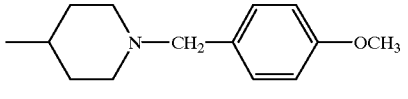 |
| 193 | 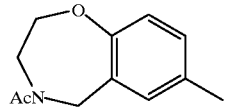 | 2 | 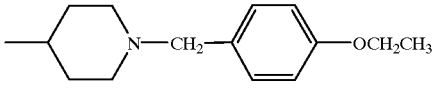 |
| 194 | 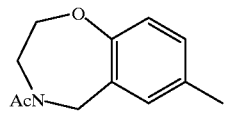 | 2 | 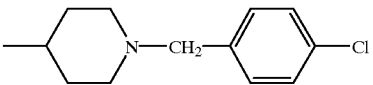 |
| 195 | 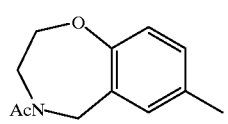 | 2 | 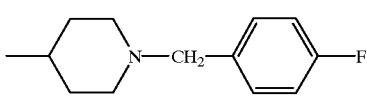 |

TABLE 15-continued
| No. | 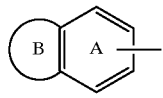 | n | Y |
|---|---|---|---|
| 196 | 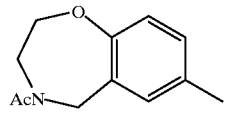 | 2 | 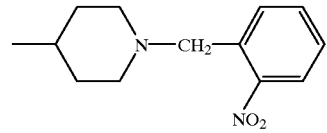 |
| 197 | 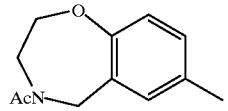 | 2 | 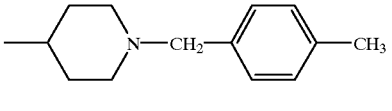 |
| 198 | 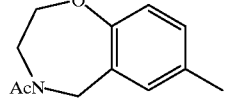 | 2 | 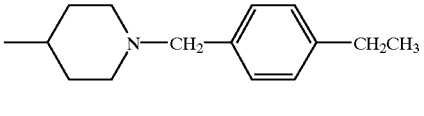 |
| 199 | 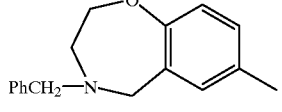 | 2 | 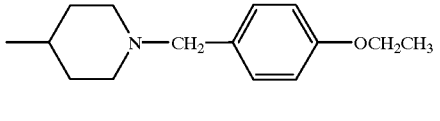 |
| 200 | 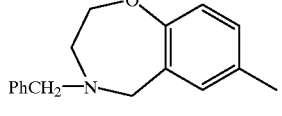 | 2 | 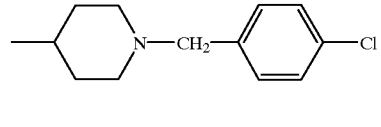 |
| 201 | 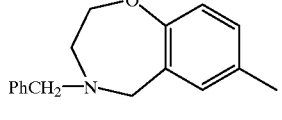 | 2 | 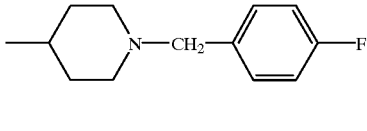 |
| 202 | 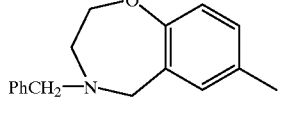 | 2 | 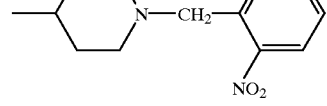 |
| 203 | 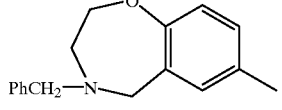 | 2 | 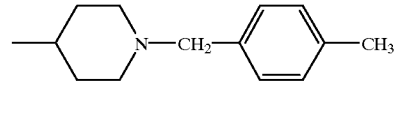 |
| 204 | 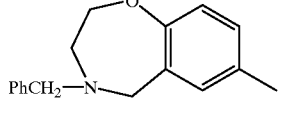 | 2 | 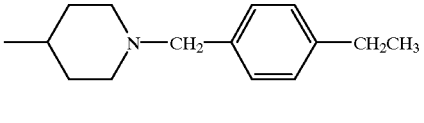 |

TABLE 16
| No. | | n | Y |
|---|---|---|---|
| 205 | 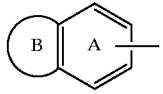 | 2 |  |
| 206 | 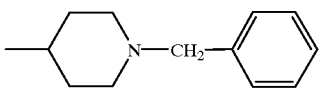 | 2 | 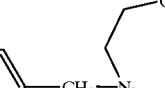 |
| 207 | 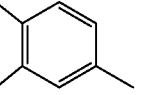 | 2 | 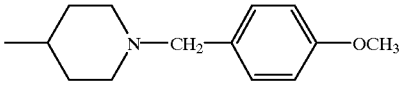 |
| 208 | 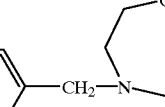 | 2 | 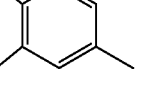 |
| 209 | 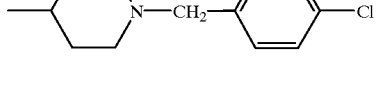 | 2 | 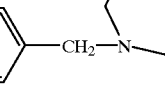 |
| 210 | 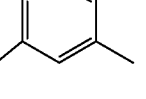 | 2 |  |
| 211 | 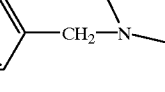 | 2 | 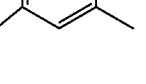 |
| 212 |  | 2 | 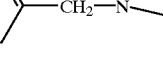 |
| 213 |  | 2 |  |

TABLE 16-continued

| No. | ![B-A structure] | n | Y |
|---|---|---|---|
| 214 | 4-Cl-C6H4-CH2-N-benzoxazepine-7-CH3 | 2 | 4-piperidinyl-N-CH2-C6H4-4-F |
| 215 | 4-Cl-C6H4-CH2-N-benzoxazepine-7-CH3 | 2 | 4-piperidinyl-N-CH2-C6H4-4-NO2 |
| 216 | 4-Cl-C6H4-CH2-N-benzoxazepine-7-CH3 | 2 | 4-piperidinyl-N-CH2-C6H4-4-CH3 |

TABLE 17

| No. | ![B-A structure] | n | Y |
|---|---|---|---|
| 217 | 4-F-C6H4-CH2-N-benzoxazepine-7-CH3 | 2 | 4-piperidinyl-N-CH2-C6H5 |
| 218 | 4-F-C6H4-CH2-N-benzoxazepine-7-CH3 | 2 | 4-piperidinyl-N-CH2-C6H4-4-OCH3 |
| 219 | 4-F-C6H4-CH2-N-benzoxazepine-7-CH3 | 2 | 4-piperidinyl-N-CH2-C6H4-4-Cl |
| 220 | 4-F-C6H4-CH2-N-benzoxazepine-7-CH3 | 2 | 4-piperidinyl-N-CH2-C6H4-4-F |

TABLE 17-continued
| No. | (structure with B, A rings) | n | Y |
|---|---|---|---|
| 221 | 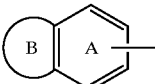 | 2 | 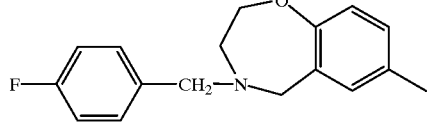 |
| 222 | 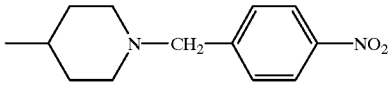 | 2 | 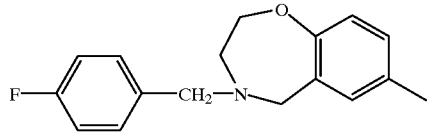 |
| 223 | 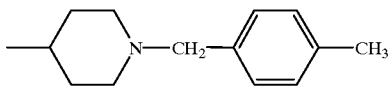 | 2 | 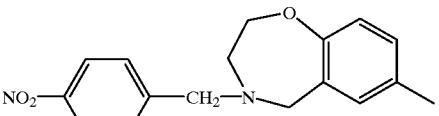 |
| 224 | 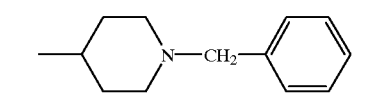 | 2 | 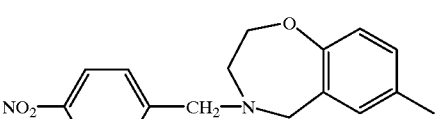 |
| 225 | 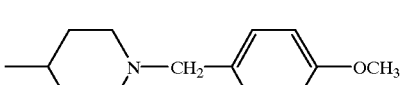 | 2 | 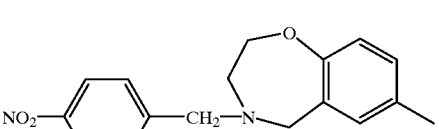 |
| 226 | 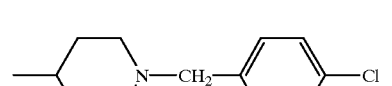 | 2 | 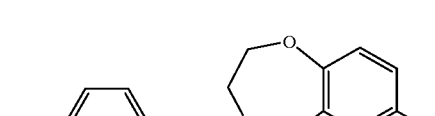 |
| 227 |  | 2 | 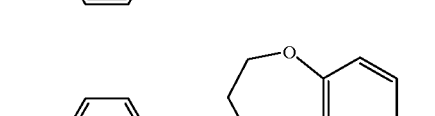 |
| 228 |  | 2 | 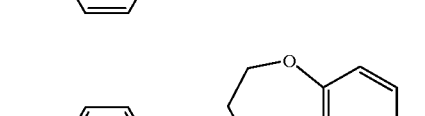 |

TABLE 18

| No. | (B A)— | n | Y |
|---|---|---|---|
| 229 | CH₃-⌬-CH₂-N(benzoxazepine-CH₃) | 2 | piperidine-N-CH₂-Ph |
| 230 | CH₃-⌬-CH₂-N(benzoxazepine-CH₃) | 2 | piperidine-N-CH₂-⌬-OCH₃ |
| 231 | CH₃-⌬-CH₂-N(benzoxazepine-CH₃) | 2 | piperidine-N-CH₂-⌬-Cl |
| 232 | CH₃-⌬-CH₂-N(benzoxazepine-CH₃) | 2 | piperidine-N-CH₂-⌬-F |
| 233 | CH₃-⌬-CH₂-N(benzoxazepine-CH₃) | 2 | piperidine-N-CH₂-⌬-NO₂ |
| 234 | CH₃-⌬-CH₂-N(benzoxazepine-CH₃) | 2 | piperidine-N-CH₂-⌬-CH₃ |
| 235 | HN(benzoxazepine-CH₃) | 2 | piperazine-N-CH₂-Ph |
| 236 | PhCH₂-N(benzoxazepine-CH₃) | 4 | piperidine-N-CH₂Ph |
| 237 | AcN(benzoxazepine-CH₃) | 3 | piperidine-N-CH₂Ph |

TABLE 18-continued
| No. | 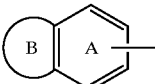 | n | Y |
|---|---|---|---|
| 238 | 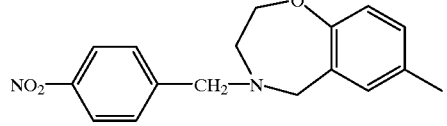 | 3 | 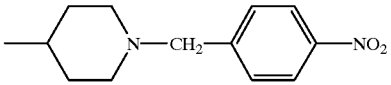 |
| 239 | 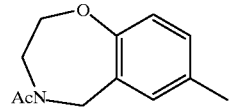 | 4 | 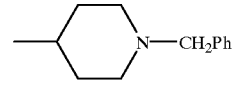 |
| 240 | 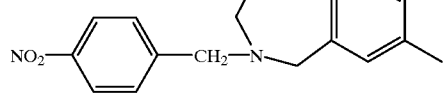 | 4 | 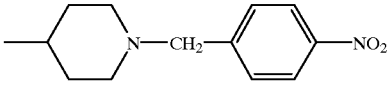 |
TABLE 19
| No. | 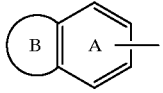 | n | Y |
|---|---|---|---|
| 241 | 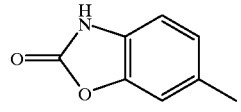 | 2 | 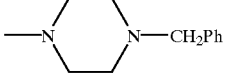 |
| 242 | 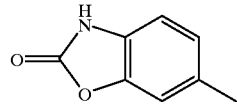 | 4 | 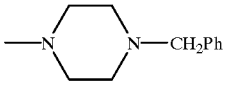 |
| 243 | 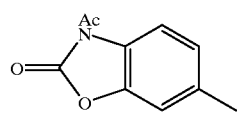 | 2 | 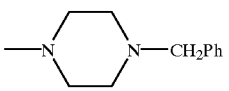 |
| 244 | 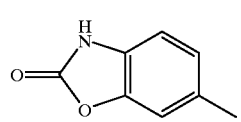 | 2 | 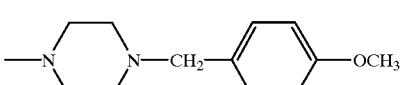 |

TABLE 19-continued

| No. | 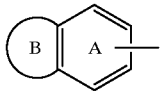 | n | Y |
|---|---|---|---|
| 245 | 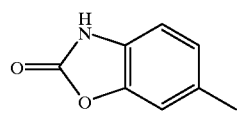 | 2 | 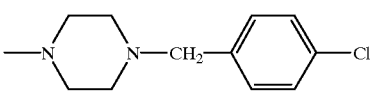 |
| 246 | 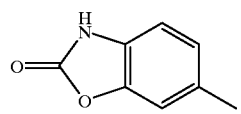 | 2 | 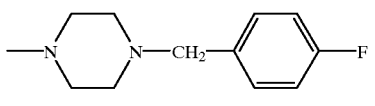 |
| 247 | 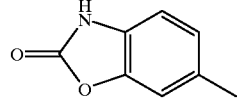 | 2 | 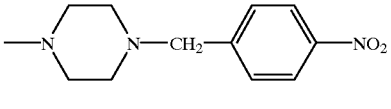 |
| 248 | 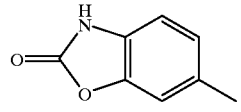 | 2 | 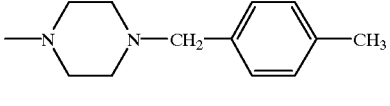 | wherein Ac represents an acetyl group; Et represents an ethyl group; and Ph represents a phenyl group.

As salts of the compound of the formula [I] and [I'] of this invention, physiologically acceptable acid addition salts are preferred. Examples of these salts include salts with inorganic acids (e.g. hydrochloric acid, phosphoric acid, hydrobromic acid, sulfuric acid, etc.) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.).

Further, where the compound of the formula [I] and [I'] of this invention has an acid group such as —COOH, the compound of the formula [I] and [I'] may form a salt with an inorganic base (e.g. ammonia, an alkali metal such as sodium, potassium, etc. or alkaline earth metal such as calcium, magnesium, etc.) or with an organic base (e.g. a tri-$C_{1-3}$ alkylamine such as trimethylamine, triethylamine and the like), and these salts are involved in the subjects of the present invention.

In the following, the method of producing the compound of the formula [I] or its salts of the present invention is described.

It should be understood that the following description applies not only to the production of the compound of the formula [I] per se but also to the production of its salts, and these compounds are simply referred to as the compound of the formula [I] inclusively in the description.

The compound of the formula [I] may be produced by, for example, reacting a compound represented by the formula:

[II-a]

wherein each symbol is of the same meaning as defined above, or a salt thereof, with a compound represented by the formula:

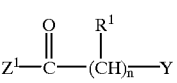

[III]

wherein $Z^1$ represents a leaving group and other symbols have the same meanings as defined above, or a salt thereof.

As examples of the leaving group shown by $Z^1$ there may be mentioned a halogen atom (e.g. chlorine, bromine, iodine, etc.), a $C_{1-6}$ alkylsulfonyloxy group (e.g. methanesulfonyloxy, ethanesulfonyloxy, propanesulfonyloxy, etc.), a $C_{6-10}$ arylsulfonyloxy group (e.g. benzenesulfonyloxy, p-toluenesulfonyloxy and the like) and so on. The preferred leaving group includes a halogen atom such as chlorine.

The compound of the formula [II-a] or salts thereof may be prepared in accordance with a conventional method or a method analogous thereto, for example, descriptions on Indian J. Chem., 2, 211 (1964), Indian J. Chem., 12, 247, (1974), Bull. Chem. Soc., Jpn., 43, 1824 (1970), Chem. Pharm. Bull., 20, 1328 (1972), Chem. Pharm. Bull., 27, 1982 (1979), Helv. Chem. Acta, 46, 1696 (1963), Synthesis, 541 (1979), U.S. Pat. Nos. 3,682,962, 3,911,126, Ger. Offen. 2,314,392 and Ger. Offen. 1,545,805.

The compound of the formula [III] and salts thereof of may be produced in accordance with a conventional method or a method analogous thereto. For example, the same can be produced in accordance with descriptions on Chem. Pharm. Bull., 34, 3747–3761 (1986) and EP-A-0,378,207.

Examples of the salts of the compound of the formula [II-a] and [III] include salts with inorganic acids (e.g. hydrochloric acid, phosphoric acid, hydrobromic acid, sulfuric acid, etc.) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.). Further, where the compound of the formula [II-a] and [III] has an acid group such as —COOH, the compound of the formula [II-a] and [III] may form a salt with an inorganic base (e.g. an alkali metal such as sodium, potassium, etc., an alkaline earth metal such as calcium, magnesium, etc., or ammonia) or with an organic base (e.g. tri-$C_{1-3}$ alkylamine such as trimethylamine, triethylamine. and the like).

The reaction of the compound of the formula [III] or a salt thereof with the compound of the formula [II-a] or a salt thereof can be conducted by reacting the compound of the formula [III] or a salt thereof, with the compound of the formula [II-a] or a salt thereof without using a solvent or, upon necessity, in a solvent.

As the solvent, any one which is conventionally usable in chemical reactions, unless it disturbs proceeding of the reaction, can be employed, as exemplified by organic solvents including hydrocarbons (e.g. pentane, hexane, benzene, toluene, nitrobenzene, etc.), halogenated hydrocarbons (e.g. dichloromethane, chloroform, 1,2-dichloroethane, carbon tetrachloride, etc.), ethers (e.g. ethyl ether, tetrahydrofuran, dioxane, dimethoxyethane, etc.), nitro alkanes (e.g. nitromethane, propionitrile, etc.) and carbon disulfide. The preferred examples of such solvent include dichloromethane, 1,2-dichloroethane, nitrobenzene and carbon disulfide.

The amount of the solvent ranges usually from 0.5 to 100 ml, preferably from 5 to 20 ml, relative to 1 mmol. of the compound of the formula [III] or a salt thereof. The reaction temperature is usually from about −30° C. to about 150° C., preferably from about 20° C. to about 100° C. The reaction time runs usually from 0.5 to 72 hours, preferably from 1 to 16 hours.

The reaction may be carried out in the presence of a Lewis acid. As the Lewis acid to be employed in this reaction, use is made of, for example, aluminum chloride, zinc chloride, titanium chloride, tin(IV) chloride, boron trifluoride, iron(II) chloride, iron(III) chloride, antimony(V) pentachloride, bismuth(III) chloride, silver(II) chloride, hydrogen fluoride sulfuric acid, polyphosphoric acid and so on. As the preferred examples, there may be mentioned Fiedel-Crafts catalysts such as aluminum chloride and the like. The amount of the Lewis acid ranges usually from 1 to 10 mol., preferably from 2 to 10 mol., relative to 1 mol. of the compound of the formula [III] or a salt thereof. The amount to the compound of the formula [II-a] or a salt thereof relative to 1 mol. of the compound of the formula [III] or a salt thereof is usually from about 1 to 20 mol., preferably from about 1 to 5 mol.

In the above reaction, the position where the group of the formula of the compound of the formula [III] or a salt thereof:

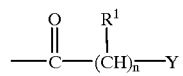

is introduced into the compound of the formula [II-a] or a salt thereof may be any of the positions on the ring A on with the substitution can take place. For example, when the skeleton of the compound of the formula [II-a] or a salt thereof is 2,3,4,5-tetrahydro-1,4-benzoxazepine (provided that the ring A is unsubstituted), the group of the compound of the formula [III] or a salt thereof is introduced mainly into 7-position, while such compounds as having the group introduced at any other positions (6-position, 8-position or 9-position) can be produced and isolated as well.

The compound of the formula:

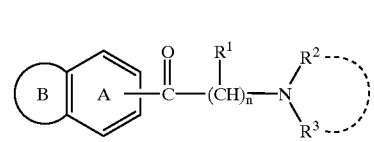

[VI-a]

wherein each symbol has the same meaning as defined above, or a salt thereof, may be produced also by reacting a compound of the formula:

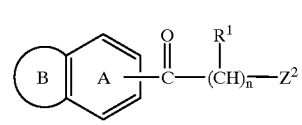

[IV-a]

wherein each symbol has the same meaning as defined above, or a salt thereof, with a compound of the formula:

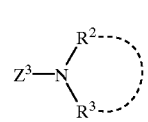

[V]

wherein each symbol has the same meaning as defined above, or a salt thereof.

As examples of the leaving group shown by $Z^2$, there may be mentioned, a halogen atom (e.g. chlorine, bromine, iodine, etc.), a $C_{1-6}$ alkylsulfonyloxy group (e.g. methanesulfonyloxy, ethanesulfonyloxy, etc.), a $C_{6-10}$ arylsulfonyloxy group (e.g. benzenesulfonyloxy, p-toluenesulfonyloxy, etc.) and so on. The preferred examples of the leaving group shown by $Z^2$ include a halogen atom such as chlorine, bromine and the like.

As the leaving group shown by $Z^3$, which can be left with $Z^2$, there may be mentioned, for example, a hydrogen atom, a trialkylsilyl group (e.g. trimethylsilyl, triethylsilyl, t-butyldimethylsilyl, etc.). The preferred includes a hydrogen atom.

As salts of the compound of the formula [VI-a], use is made of those similar to the salts of the compound of the formula [I] as described above.

The salts of the compound of the formula [IV-a] and [V] are exemplified as salts with inorganic acids (e.g. hydrochloric acid, phosphoric acid, hydrobromic acid, sulfuric acid, etc.) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid and the like). Further, in the case where the compound of the formula [IV-a] and [V] of this invention has an acid group such as —COOH, the compound of the formula [IV-a] and [V] may form a salt with an inorganic base (e.g. an alkali metal such as sodium, potassium, etc., an alkaline earth metal such as calcium, magnesium, etc., or ammonia) or with an organic base (e.g. tri-$C_{1-3}$ alkylamine such as trimethylamine, triethylamine and the like).

The amount of the compound of the formula [V] or a salt thereof to be employed in this reaction is, usually, from 1.0 to 50.0 times as much mol., preferably 1.0 to 10.0 times as much mol. relative to one mol. of the compound of the formula [IV-a] or a salt thereof. This reaction can be conducted under cooling or under heating (at temperatures ranging from 0° C. to 120° C.). The reaction is completed in, usually, from 10 minutes to 48 hours, preferably from 2 to 16 hours.

The reaction can be conducted in the absence of solvent, or if necessary, in a solvent. As the solvent, any one can be employed unless it disturbs the proceeding of the reaction. Examples of such solvent include lower alcohols such as methanol, ethanol, propanol, isopropanol, n-butanol, t-butanol, etc., ethers such as dioxane, ethyl ether, tetrahydrofuran, etc., aromatic hydrocarbons such as benzene, toluene, xylene, etc., amides such as dimethylformamide, dimethylacetamide, hexamethylphosphonotriamide, etc., esters such as ethyl acetate, butyl acetate, etc. and so on. The amount of the solvent relative to 1 mmol. of the compound of the formula [IV-a] or a salt thereof is, usually, from 0.5 to 100 ml, preferably from 5 to 20 ml.

The reaction can also be carried out in the presence of a base, if necessary. Examples of the base to be used include inorganic bases such as sodium carbonate, potassium carbonate, lithium carbonate, sodium hydroxide, potassium hydroxide, sodium methoxide, sodium ethoxide, sodium hydride, etc. and organic bases such as pyridine, 4-dimethylaminopyridine, triethylamine and the like. The amount of the base runs, usually, from equimol. to excess amount, preferably from 1.0 to 5.0 times as much mol. relative to the compound of the formula [V] or a salt thereof.

It is also possible to promote the reaction by allowing an iodide (e.g. sodium iodide, potassium iodide, lithium iodide, etc.) to be present in the reaction system. The amount of the iodide relative to the compound of the formula [IV-a] or a salt thereof is, usually, from 1 to 5, preferably 1.0 to 1.5 times as much mol.

The starting compound of the formula [IV-a] or a salt thereof may be prepared by reacting a compound represented by the formula:

[II-a]

wherein each symbol has the same meaning as defined above, or a salt thereof, with a compound represented by the formula:

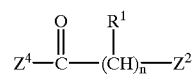

[VIII]

wherein $Z^4$ represents a leaving group, and other symbols have the same meanings as defined above.

As examples of the leaving group shown by $Z^4$, there may be mentioned a halogen atom (e.g. chlorine, bromine, iodine, etc. ), a $C_{1-6}$ alkylsulfonyloxy group (e.g. methanesulfonyloxy, ethanesulfonyloxy, propanesulfonyl, etc.), a $C_{6-10}$ arylsulfonyloxy group (e.g. benzenesulfonyloxy, p-toluenesulfonyloxy, etc.) and so on. The preferred examples of the leaving group include a halogen atom such as chlorine, etc.

The compound of the formula [VIII] can be produced by a conventionally known method or a method analogous thereto.

The reaction of the compound of the formula [II-a] or a salt thereof with the compound of the formula [VIII] can be conducted under the same conditions as in the reaction of the compound of the formula [II-a] or a salt thereof with the compound of the formula [III] or a salt thereof.

In the above reaction, the position where the group of the compound of the formula [VIII] or a salt thereof:

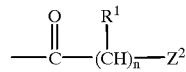

is introduced into the compound of the formula [II-a] or a salt thereof may be any of the positions on the ring A on which the substitution can take place. For example, where the skeleton of the compound of the formula [II-a] or a salt thereof is 2,3,4,5-tetrahydro-1,4-benzoxazepine (provided that the ring A is unsubstituted), the group of the compound of the formula [VIII] may be introduced mainly into 7-position, while such compounds as having the group introduced at any other positions (namely, 6-position, 8-position or 9-position) can also be produced and isolated.

The compound of the formula [IV-a] or salts thereof thus obtained can be isolated and purified by a conventional means such as concentration, phasic transfer, solvent transfer, solvent extraction, fractional distillation, distillation, crystallization, recrystallization and chromatography, while they may be fed to the subsequent process as the material in the state of mixture without isolation.

The starting compound of the formula [V] or a salt thereof may be prepared by a conventionally known method or a method analogous thereto.

Among the compounds [I], a compound in which n is 2, namely, the compound of the formula:

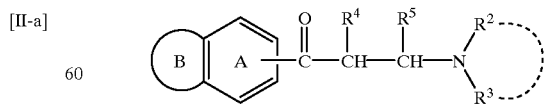

[IX]

wherein $R^4$ and $R^5$ each represents a hydrogen atom or an optionally substituted hydrocarbon group, and other symbols have the same meanings as defined above, or a salt thereof, can be produced also by reacting, for example, a compound of the formula:

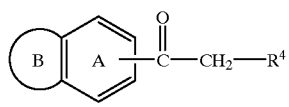 [X]

wherein each symbol has the same meaning as defined above, or a salt thereof, with a compound represented by the formula:

$R^5$—CHO [XI]

wherein $R^5$ represents the same meaning as defined above and a compound represented by the formula:

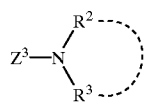 [V]

wherein each symbol has the same meaning as defined above, or a salt thereof.

As examples of the optionally substituted hydrocarbon group shown by $R^4$ and $R^5$, there may be mentioned an optionally substituted hydrocarbon group similar to those shown by $R^1$ and the like.

The example of the salts of the compound of the formula [IX] include those similar to the salts of the compound of the formula [I].

The salts of the compound [X] are exemplified as salts with inorganic acids (e.g. hydrochloric acid, phosphoric acid, hydrobromic acid, sulfuric acid, etc.) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.). Further, when the compound of the formula [X] has an acid group such as —COOH, the compound of the formula [X] may form a salt with an inorganic base (e.g. an alkali metal such as sodium, potassium, etc., an alkaline earth metal such as calcium, magnesium, etc., or ammonia) or with an organic base (e.g. tri-$C_{1-3}$ alkylamine such as trimethylamine, triethylamine and the like) and so on.

The reaction may be carried out in substantially the same manner as Mannich reaction described in Organic Reaction, Vol. 1, p 303 to 341. More practically, the reaction is conducted by allowing, for example, the compound of the formula [XI] and the compound of the formula [V] or a salt thereof to react with the compound of the formula [X] or a salt thereof in a ratio of usually 0.9 to 10, preferably 1.0 to 3.0 equivalents of the former relative to 1 equivalent of the latter.

While the reaction may be carried out usually at temperatures from room temperature to under heating (10 to 150° C.), it is conducted preferably at temperatures from 80 to 120° C. The reaction may be completed in, usually, from 1 to 48 hours, preferably from 2 to 24 hours.

The reaction may usually be carried out in the absence or presence of solvent. As the solvent, any one generally used for Mannich reaction can be applied, unless it inhibits the proceeding of the reaction. For example, alcohols such as ethanol and the like are frequently utilized. The amount of the solvent is, usually from 0.5 to 200 ml, preferably from 5 to 40 ml, relative to 1 mmol. of the compound of the formula [X] or a salt thereof.

Further, the reaction can be conducted, if desired, in the presence of an inorganic acid such as hydrochloric acid. The proportion of the acid relative to the compound [X] or a salt thereof is a catalytic amount such as 0.001 to 0.05 equivalent relative to 1 equivalent of the compound of the formula [X]. Where the compound of the formula [V] or [X] to be employed for the reaction is not in the form of salt, however, it is preferable to use the acid in an excess amount sufficient for allowing these compounds to form salts.

The compound of the formula [X] or salts thereof may be obtained by allowing the compound of the formula [II-a] or a salt thereof to react with a compound represented by the formula:

$Z^5$—CO—CH$_2$—$R^4$ [XII]

wherein $Z^5$ represents a leaving group, and other symbols have the same meanings as described above.

The reaction may be carried out under the conditions similar to those in the reaction of the compound of the formula [II-a] or a salt thereof with the compound of the formula [VIII].

The compound of the formula [XI] or salts thereof may be prepared by a conventionally known method or a method analogous thereto.

In each reactions mentioned above, where the starting compound has, as substituents, amino group, carboxyl group, hydroxyl group, etc., these groups may be protected with such protecting groups as generally used in peptide chemistry, and the object compound may be obtained by, if necessary, removing these protecting groups after the reaction.

As examples of the protecting groups of amino group, there may be mentioned formyl, an optionally substituted $C_{1-6}$ alkyl-carbonyl group (e.g. acetyl, ethylcarbonyl, etc.), a benzoyl group, a $C_{1-6}$ alkoxy-carbonyl group (e.g. methoxycarbonyl, ethoxycarbonyl, etc.), a phenyloxycarbonyl group, a $C_{7-15}$ aralkyloxy-carbonyl (e.g. benzyloxy carbonyl, fluorenyloxycarbonyl, etc.), a trityl group, a phthaloyl group and so on. The examples of the substituents which these protecting group may have include a halogen atom (e.g. fluorine, chlorine, bromine, iodine), a $C_{1-6}$ alkyl-carbonyl group (e.g. methylcarbonyl, ethylcarbonyl, butylcarbonyl, etc.), nitro group and the like. The number of these substituents is from 1 to about 3.

The protecting group of carboxyl group include, for example, an optionally substituted $C_{1-6}$ alkyl group (e.g. methyl, ethyl, n-propyl, i-propyl, n-butyl, tert-butyl, etc.), a phenyl group, a trityl group, a silyl group and so on. As examples of the substituents which these protecting group may have, there may be mentioned a halogen atom (e.g. fluorine, chlorine, bromine, iodine), formyl, a $C_{1-6}$ alkyl-carbonyl group (e.g. ethylcarbonyl, butylcarbonyl, etc.), nitro group and so on. The number of these substituents is from 1 to about 3.

The examples of the protecting group of hydroxyl group include an optionally substituted $C_{1-6}$ alkyl group (e.g. methyl, ethyl, n-propyl, i-propyl, n-butyl, tert-butyl, etc.), phenyl group, a $C_{7-10}$ aralkyl group (e.g. benzyl, etc.), formyl, a $C_{1-6}$ alkyl-carbonyl group (e.g. acetyl, ethylcarbonyl, etc.), a phenyloxycarbonyl group, a $C_{7-10}$ aralkyl-carbonyl group (e.g. benzyloxycarbonyl, etc.), pyranyl group, a furanyl group, a silyl group and so on. As examples of the substituents which these protecting group may have, there may be mentioned a halogen atom (e.g. fluorine, chlorine, bromine, iodine), a $C_{1-6}$ alkyl group, a phenyl group, a $C_{7-10}$ aralkyl group, a nitro group and the like. The number of these substituents varies from 1 to about 4.

As the means of removing these protecting group, conventionally known means or those analogous thereto are employed. Examples of such means include those which comprise processing with an acid, a base, reduction, ultraviolet-ray radiation, hydrazine, phenyl hydrazine, sodium N-methyldithiocarbamate, tetrabutylammonium fluoride, palladium acetate, and so on.

When the compound of the formula [I], [VI-a] or [IX] or salts thereof has optionally substituted acylamino group, the compound having an unsubstituted amino group or a mono-substituted amino group or a salt thereof may be produced by conducting a deacylation reaction. The compound of the formula [I], [VI-a] or [IX] having an optionally substituted acylamino group or salts thereof used as the starting compound includes those isolated and purified by a conventional means such as concentration, phasic transfer, solvent transfer, solvent extraction, fractional distillation, distillation, crystallization, recrystallization, and chromatography, while they may be fed to the subsequent process as the material in the state of mixture without isolation.

In the deacylation reaction, the compound of the formula [I], [VI-a] or [IX] having an optionally substituted acylamino group or a salt thereof is to be maintained at temperature from 10 to 150° C., preferably 50 to 100° C., in an aqueous solution of an acid such as inorganic acid (e.g. nitric acid, hydrochloric acid, hydrobromic acid, iodic acid, sulfuric acid, etc.) or of a base such as alkali metal hydroxide (e.g. sodium hydroxide, potassium hydroxide, lithium hydroxide, etc.). The amount of said acid or base relative to 1 mmol. of the compound of the formula [XII] or a salt thereof varies, usually, from 1 to 100 equivalents, preferably, from 1 to 40 equivalents. The normality of the acid or base is, usually, from about 0.1 to 10 N, preferably from about 2 to 10 N. The reaction time runs, while it also depends on the reaction temperature, usually from 1 to 24 hours, preferably from 2 to 10 hours.

Introducing optionally substituted hydrocarbon groups into the unsubstituted amino group or mono-substituted amino group of the compound of the formula [I], [VI-a] or [IX] thus obtained above or salts thereof gives the compound of the formula [I], [VI-a] or [IX] or salts thereof, whose amino groups are substituted with optionally substituted hydrocarbon groups. The compound of the formula [I], [VI-a] or [IX] having a unsubstituted amino group or a mono-substituted amino group or salts thereof, used as the starting compound, includes those isolated and purified by a conventional means such as concentration, phasic transfer, solvent transfer, solvent extraction, fractional distillation, distillation, crystallization, recrystallization, chromatography and the like, while they may be fed to the subsequent process as the material in the state of mixture without isolation.

The compound of the formula [I], [VI-a] or [IX] or salts thereof, whose amino groups are substituted with optionally substituted hydrocarbon groups, may be prepared also by reacting the compound of the formula [I], [VI-a] or [IX] or salts thereof with a compound of the formula:

$$R^7—Z^3 \qquad [XIII]$$

wherein $R^7$ represents an optionally substituted hydrocarbon group; and $Z^3$ represents a leaving group.

For example, when the ring B, the ring B' and/or the group shown by Y of the compound of the formula [I] or [II'] or salts thereof has a unsubstituted amino group or a mono-substituted amino group, the group shown by $R^7$ may be introduced into the ring B, the ring B' and/or the group shown by Y by means of reaction with the compound of the formula [XIII]. Further, when the ring B, the ring B' and/or the group shown by Y of the compound of the formula [I] or [I'] or salts thereof has a nitrogen atom of an unsubstituted amino group or a mono-substituted amino group as their ring-constituting atom, such optionally substituted hydrocarbon group may be introduced on the ring as a substituent.

The optionally substituted hydrocarbon group represented by $R^7$ include, for example, those similar to optionally substituted hydrocarbon groups as mentioned in $R^2$, $R^3$ and $R^6$.

As the leaving group shown by $Z^3$, there may be mentioned, for example, a halogen atom (e.g. chlorine, bromine, iodine, etc.), a $C_{1-6}$ alkylsulfonyloxy group (e.g. methanesulfonyloxy, ethanesulfonyloxy, etc.), a $C_{6-10}$ arylsulfonyloxy group (e.g. benzenesulfonyloxy, p-toluenesulfonyloxy, etc.) and so on. The preferred examples of these leaving groups include a halogen atom such as chlorine and the like.

The reaction may be carried out in the absence or presence of solvent or, upon necessity, in the presence of base. Examples of the base to be employed include inorganic bases such as sodium carbonate, potassium carbonate, lithium carbonate, sodium hydroxide, potassium hydroxide, sodium methoxide, sodium ethoxide, sodium hydride, etc. and organic bases such as pyridine, 4-dimethylaminopyridine, triethylamine and the like. As the solvent, any one can be employed unless it inhibits the proceeding of the reaction. As such solvent, there may be mentioned, for example, lower alcohols such as methanol, ethanol, propanol, isopropanol, n-butanol, t-butanol, etc., ethers such as dioxane, ethyl ether, tetrahydrofuran, etc., aromatic hydrocarbons such as benzene, toluene, xylene, etc., amides such as dimethylformamide, dimethylacetamide, hexamethylphosphonotriamide, etc., esters such as ethyl acetate, butyl acetate, etc. The reaction may be carried out under cooling such as at the temperature from about 0° C. to 10° C., at the room temperature such as at the temperature from about 10° C. to 40° C. or under heating such as at the temperature from about 40° C. to 120° C., and the reaction time varies, usually, from 10 minutes to 48 hours, preferably from 2 to 16 hours.

The amount of the compound of the formula [XIII] is, preferably, from 0.3 to 5.0 times as much mol. relative to the compound of the formula [I], [VI-a] or [IX] having an unsubstituted amino group or a mono-substituted amino group or a salt thereof. The amount of the base to be used relative to the compound of the formula [I], [VI-a] or [IX] having an unsubstituted amino group or a mono-substituted amino group or a salt thereof varies, usually, from equimol. to excess amount, preferably from 1.1 to 5.0 times as much mol.

It is also possible to promote the reaction by allowing an iodide (e.g. sodium iodide, potassium iodide, lithium iodide, etc.) to be present in the reaction system. The amount of the iodide to be employed is, usually, from 1 to 5, preferably 1.1 to 1.5 times as much mol. relative to the compound of the formula [XI].

The compound of the formula [XIII] may be prepared by a conventionally known method or a method analogous thereto.

The novel compound of the formula [I'] or salts thereof of the present invention may be produced in the same manner as mentioned in the production of the compound of the formula [I] or salts thereof.

Where the resulting compound of the formula [I] or [I'] thus obtained above is in the free form, they may be led to salts thereof by conventional means or those analogous thereto. Conversely, when the compound is obtained in the form of salt, it may be led to the free compound or any other salt by conventional means or those analogous thereto. The resulting compound of the formula [I] or [I'] or a salt thereof may be isolated and refined by conventional separating means as mentioned above.

The compound of the formula [I] or [I'] or salts thereof include their stereoisomers due to the presence of asymmetric carbon atoms. These isomers may be isolated and purified by conventional means as mentioned above or by means such as fractional recrystallization, chromatography using optical active column and so on.

The compound of the formula [I] or [I'] or salts thereof of the present invention act on the central nervous system of mammals, have strong cholinesterase inhibitory activity, and exhibit excellent antiamnestic effects on various amnesia-inducing actions in man and animals such as mice and so on.

The compound of the formula [I] or [I'] or salts thereof of the present invention are remarkably excellent in separation of effects on central nervous system from those on peripheral nervous system, as compared with physostigmine and, at the antiamnestic dose level, do not cause peripheral nervous system effects such as spasm, salivation, diarrhea, etc. or, if they do, only slightly. Moreover, they are characterized by a long duration of effects and low toxicity, ensuring a remarkably high efficacy when administered orally. The acute toxicity ($LD_{50}$) of the compound of the formula [I] or [I'] or salts thereof of the present invention is not less than 100 mg/kg. Therefore, the compounds of this invention are useful as a safely administrable agent for improving the cerebral function of mammalian animals such as human beings.

Examples of diseases on which the compounds of this invention are effective include senile dementia, Alzheimer's diseases, Huntington's chorea, hyperkinesia and mania. The compounds of this invention may be used for the prophylaxis or therapy of these diseases.

The compounds of this invention are usually formulated with pharmaceutically acceptable carriers or excipients, which may be administered orally or non-orally to man and other mammalian animals.

Such pharmaceutical preparations include those for oral administration (e.g. solid pharmaceutical preparations such as powders, tablets, granules and capsules, liquid pharmaceutical solutions such as solutions, suspensions and emulsions) and for non-oral administration (e.g. suppositories, injections such as solutions and suspensions, etc.). These pharmaceutical preparations may be prepared by conventionally known methods.

When the pharmaceutical composition is formulated into a solid pharmaceutical preparation, examples of the carriers include various excipients such as lactose, powder sugar, mannitol, cornstarch, talc, crystalline cellulose (Avicel etc.), magnesium stearate, light silicic anhydride, magnesium carbonate, calcium carbonate, L-cysteine, etc.; binders such as starch, alpha-starch, cane sugar, gelatin, powdered gum arabic, methylcellulose, carboxymethylcellulose, carboxymethylcellulose sodium, hydroxypropylcellulose, hydroxypropylmethylcellulose, polyvinylpyrrolidone, pullulan, dextrin, etc.; disintegrators such as carboxymethylcellulose calcium, low-substituted hydroxypropylcellulose, croscarmellose sodium, croscarmellose calcium, etc.; surfactants including anionic surfactants such as sodium alkylsulfates etc. and nonionic surfactants such as polyoxyethylene-sorbitan fatty acid esters, polyoxyethylene-fatty acid esters and polyoxyethylene-castor oil derivatives, etc.; colorants; corrigents; adsorbents; preservatives; wetting agents; antistatic agents; disintegration retarders; and so on. The solid pharmaceutical preparation may be a coated preparation which is prepared by coating powders, tablets granules and the like with a coating composition.

When the pharmaceutical preparation is formulated into an injection, the resulting solution and suspension are preferably sterilized, and are isotonic with respect to the blood. In formulating the pharmaceutical preparation into the form of a solution or suspension, diluents such as water, ethyl alcohol and the like can be used. Sodium chloride, glucose or glycerol may be incorporated into a pharmaceutical preparation, in an amount sufficient to prepare isotonic solutions. The pharmaceutical preparation may further contain ordinary dissolving aids, buffers, and optionally coloring agents, perfumes, flavors, sweeteners, preservatives, and other drugs.

While depending on the type and symptom of diseases to be treated, the dosage in oral administration to general adult humans (70 kg body weight) varies from about 0.01 mg to 50 mg, preferably from 0.1 to 30 mg, more preferably from 0.5 to 10 mg per day.

The cholinesterase inhibitors of the present invention contain, usually, about 0.01 to 70% by weight, preferably about 1 to 50% by weight of the compound of the formula [I] or [I'] based on the total weight of the preparation. It is advantageous that the compound of the formula [I] or [I'] of the present invention is contained in a single unit dose form, usually, in an amount of about 10 to 1000 mg while it depends on the type and symptom of diseases to be treated.

EXAMPLES

By the following examples, reference examples, formulation examples and experimental examples, the present invention will be illustrated in more concrete manner, but they should by no means be construed as defining the metes and bounds of this invention.

In the experimental examples and reference examples, elution in the procedure of column chromatography was carried out under observation by means of TLC (Thin Layer Chromatography) unless otherwise specified. In the TLC observation, $60F_{254}$ manufactured by Merck as the TLC plate, the solvent, as the developer, used as elution solvent for the column chromatography were utilized, and a UV detector was employed for detection. As an adjunctive detection procedure, the spot on the TLC plate was sprayed with 48% HBr, heated to hydrolyze, sprayed with a ninhydrin reagent and heated again, then the change to a red—reddish purple was regarded as positive reaction. The fractions containing the object compound were pooled. Unless otherwise specified, Merck Kieselgel 60 (70 to 230 mesh) was applied as the silica gel for the column.

The term "ambient temperature" or "room temperature" generally means temperatures ranging from about 5° C. to 40° C., and the term "atmospheric pressure" means the neighborhood of one atmospheric pressure.

Unless otherwise specified, "%" denotes percentage by weight.

Example 1

3-(1-Acetylpiperidin-4-yl)-1-(4-acetyl-2,3,4,5-tetrahydro-1,4-benzoxazepin-7-yl)-1-propanone

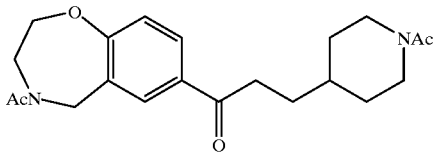

(1) To a solution of 1.5 g of 2,3,4,5-tetrahydro-1,4-benzoxazepin-5-one in 20 ml of tetrahydrofuran, was added 0.5 g of lithium aluminium hydride by portion, and the mixture was heated and refluxed for 2 hours. The reaction mixture was cooled to the room temperature. To the reaction mixture were added dropwise 1 ml of water and 0.8 ml of 10% aqueous solution of sodium hydroxide, and the mixture was stirred for 6 hours at room temperature. After the resultant solid mater was removed by filtration, the filtrate was concentrated under reduced pressure, and 20 ml of dichloromethane was added to the residue. The solution was dried over anhydrous sodium sulfate, then to the solution was added 0.94 ml of acetic anhydride, the mixture was stirred for 15 minutes at room temperature. The solvent was distilled off under reduced pressure, and the resulting oily residue was purified by means of column chromatography (developing solvent: dichloromethane-ethyl acetate=5:1 (V/V)) to give 1.8 g of 4-acetyl-2,3,4,5-tetrahydro-1,4-benzoxazepine as a colorless oily substance. The compound was used in the following steps without further purification.

(2) To a solution of 1.15 g of the oily substance thus obtained in the step (1) and 1.28 g of 3-(1-acetylpiperidin-4-yl)propionylchloride in 50 ml of 1,2-dichloroethane was added 2.50 g of aluminium chloride by portions and the mixture was heated for 2 hours under reflux. The reaction mixture was poured into ice-water and was subjected to extraction with dichloromethane. The extract was dried over anhydrous sodium sulfate and the solvent was distilled off. The residue was purified by means of chromatography (developing solvent: ethyl acetate-methanol=20:1 (V/V)) to give 1.6 g of the title compound as a viscous oily substance.

Elemental Analysis for $C_{21}H_{28}N_2O_4$:
Calcd.: C, 67.72; H, 7.58; N, 7.52
Found: C, 67.68; H, 7.61; N, 7.53

Example 2

3-(Piperidin-4-yl)-1-(2,3,4,5-tetrahydro-1,4-benzoxazepin-7-yl)-1-propanone dihydrochloride

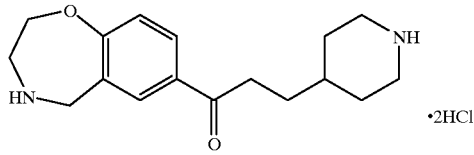

3-(1-Acetylpiperidin-4-yl)-1-(4-acetyl-2,3,4,5-tetrahydro-1,4-benzoxazepin-7-yl)-1-propanone (1.5 g) obtained in Example 1 was dissolved in 30 ml of conc. hydrochloric acid, and the mixture was stirred for 16 hours under reflux. Excess volume of the conc. hydrochloric acid was distilled off under reduced pressure and ethanol was added to the residue. The resultant crystals were collected by filtration, and washed with ethanol. The crystals were dried under reduced pressure to give 1.4 g of the title compound as colorless scaly crystals, m.p. >300° C.

Elemental Analysis for $C_{17}H_{24}N_2O_2.2HCl$:
Calcd.: C, 56.51; H, 7.25; N, 7.75
Found: C, 56.29; H, 7.33; N, 7.79

Example 3

(A) 3-[1-(Phenylmethyl)piperidin-4-yl]-1-(2,3,4,5-tetrahydro-1,4-benzoxazepin-7-yl)-1-propanone dihydrochloride and (B) 1-[4-(Phenylmethyl)-2,3,4,5-tetrahydro-1,4-benzoxazepin-7-yl]-3-[1-(phenylmethyl)piperidin-4-yl]-1-propanone dihydrochloride (A)

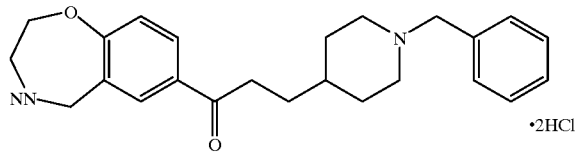

(B)

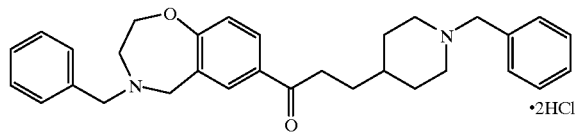

To a solution of 1.1 g of the compound obtained in Example 2 in 10 ml of water was added an 10% aqueous solution of sodium hydroxide to adjust basic and the mixture was subjected to extraction with dichloromethane. The extract was dried over anhydrous sodium sulfate and the solvent was distilled off under reduced pressure to give 0.80 g of the free base form of 3-(piperidin-4-yl)-1-(2,3,4,5-tetrahydro-1,4-benzoxazepin-7-yl)-1-propanone as a colorless oily substance.

A solution of 0.45 g of benzyl bromide in 5 ml of ethanol was added dropwise to a suspension of the 0.80 g of the oily substance thus obtained and 0.50 g of potassium carbonate in 30 ml of ethanol under ice-cooling and the mixture was stirred for 2 hours under ice-cooling. The solvent was distilled off under reduced pressure, and water was added to the residue and the mixture was subjected to extraction with dichloroethane. The extract was dried over anhydrous sodium sulfate, and the solvent was distilled off under reduced pressure. The residue was purified by means of silica gel column chromatography (developing solvent: ethyl acetate-methanol=50:1 to 5:1 (V/V)) to give 0.35 g of free base form of the title compound (B) as a colorless oily substance in the first eluted fraction and to give 0.42 g of free base form of the title compound (A) as colorless crystals in the second eluted fraction, m.p. 108–109° C.

To the oily substance thus obtained above (free base form of the compound (B)) was added 2 equivalents of methanolic hydrochloric acid. The excess amount of methanol was distilled off to give 0.32 g of the title compound (B) as colorless crystals, m.p. 201–205° C.

Elemental Analysis for $C_{31}H_{36}N_2O_2 \cdot 2HCl$:

Calcd.:C, 68.75; H, 7.07; N, 5.17

Found: C, 68.66; H, 7.21; N, 5.14

To the colorless crystals thus obtained above (free base form of the compound (A)) was added 2 equivalents of methanolic hydrochloric acid, and the excess amount of methanol was distilled off and the residue was crystallized from ether to give 0.41 g of the title compound (A) as colorless crystalline powder, m.p. 236–239° C.

Elemental Analysis for $C_{24}H_{30}N_2O_2 \cdot 2HCl$:

Calcd.: C, 63.86; H, 7.14; N, 6.21

Found : C, 63.69; H, 7.20; N, 6.09

Example 4

1-(4-Acetyl-2,3,4,5-tetrahydro-1,4-benzoxazepin-7-yl)-3-[1-(phenylmethyl)piperidin-4-yl]-1-propanone hydrochloride

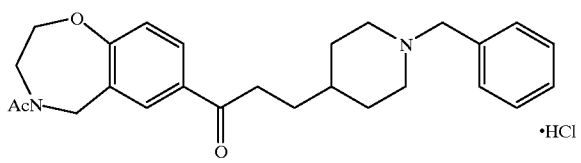

In 5 ml of dichloromethane, 0.2 g of free base form of the compound (A), that is, 3-[1-(phenylmethyl) piperidin-4-yl]-1-(2,3,4,5-tetrahydro-1,4-benzoxazepin-7-yl)-1-propanone obtained in Example 3 was dissolved. To the solution was added 60 mg of acetic anhydride, and the mixture was stirred for 30 minutes under reflux. Water was added to the reaction solution, and the mixture was subjected to extraction with dichloromethane. The extract was washed successively with 5% aqueous solution of sodium hydroxide, and water, and was dried over anhydrous sodium sulfate. The solvent was distilled off under reduced pressure, and the residue was purified by silica gel column chromatography (developing solvent: ethyl acetate-methanol=20:1 (V/V)) to give 0.21 g of free base form of the title compound as a colorless oily substance. To the oily substance was added 1 equivalent of methanolic hydrochloric acid, and methanol was distilled off to give 0.19 g of the title compound as colorless amorphous powder.

Elemental Analysis for $C_{26}H_{32}N_2O_3 \cdot HCl$:

Calcd.: C, 68.33; H, 7.28; N, 6.13

Found: C, 68.06; H, 7.27; N, 6.11

Example 5

1-[4-(4-Methoxyphenylmethyl)-2,3,4,5-tetrahydro-1,4-benzoxazepin-7-yl]-3-[1-(phenylmethyl)piperidin-4-yl]-1-propanone dihydrochloride

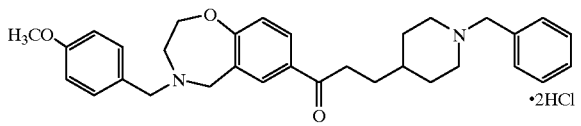

A suspension of 0.2 g of free base form of the compound (A) obtained in Example 3, namely, 3-[1-(phenylmethyl) piperidin-4-yl]-1-(2,3,4,5-tetrahydro-1,4-benzoxazepin-7-yl)-1-propanone, 90 mg of 4-methoxybenzylchloride, 0.1 g of potassium carbonate and 0.11 g of potassium iodide in 8 ml of ethanol was stirred for 4 hours under reflux. After the solvent was distilled off under reduced pressure, water was added to the residue, and the mixture was extracted with dichloromethane. The extract was dried over anhydrous sodium sulfate, and the solvent was distilled off. The residue was purified by means of silica gel column chromatography (developing solvent: ethyl acetate-methanol=20:1 (V/V)) to give 0.22 g of free base form of the title compound as a colorless oily substance. To the oily substance was added 2 equivalents of methanolic hydrochloric acid; and methanol was distilled off to give 0.21 g of the title compound as colorless powder, m.p. 208–211° C.

Elemental Analysis for $C_{32}H_{38}N_2O_3 \cdot 2HCl$:

Calcd.: C, 67.24; H, 7.05; N, 4.90

Found: C, 67.03; H, 7.09; N, 4.91

Example 6

1-(4-Formyl-2,3,4,5-tetrahydro-1,4-benzoxazepin-7-yl)-3-[4-(phenylmethyl)piperazin-1-yl]-1-propanone dihydrochloride

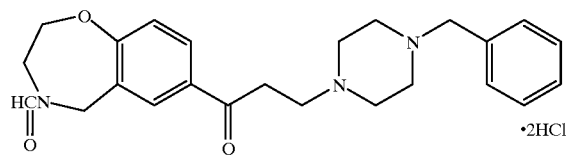

A solution of 1.9 g of 3-chloro-1-(4-formyl-2,3,4,5-tetrahydro-1,4-benzoxazepin-7-yl)-1-propanone obtained in Reference Example 1, 1.25 g of 1-(phenylmethyl)piperazine and 1.28 g of sodium carbonate in 20 ml of ethanol was stirred for 2 hours at room temperature, then the solvent was distilled off. To the residue was added water, and the mixture was subjected to extraction with dichloromethane. The extract was washed with water, then dried over anhydrous sodium sulfate. After the solvent was distilled off under reduced pressure, the residue was purified by means of silica gel column chromatography (developing solvent: ethyl acetate-methanol=10:1 (V/V)) to give 2.55 g of free base form of the title compound as a colorless oily substance. To 0.3 g of the oily substance was added 2 equivalents of methanolic hydrochloric acid, and methanol was distilled off. The residue was crystallized from ether to give 0.31 g of the title compound as colorless powder, m.p. 181–185° C.

Elemental Analysis for $C_{24}H_{29}N_3O_3 \cdot 2HCl$:

Calcd.: C, 60.00; H, 6.50; N, 8.75

Found: C, 59.79; H, 6.48; N, 8.71

Example 7

3-[4-(Phenylmethyl)piperazin-1-yl]-1-(2,3,4,5-tetrahydro-1,4-benzoxazepin-7-yl)-1-propanone trihydrochloride

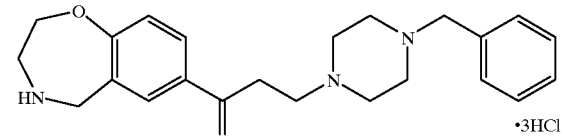

Free base form of 1-(4-formyl-2,3,4,5-tetrahydro-1,4-benzoxazepin-7-yl)-3-[4-(phenylmethyl)piperazin-1-yl]-1- propanone (1.3 g) obtained in Example 6 was dissolved in a mixed solution of methanol (24 ml) and 6N hydrochloric acid (24 ml). The mixture was stirred for 2 hours under reflux, and methanol was distilled off under reduced pressure. The aqueous solution was adjusted to weak basicity (pH=approximately 8) with a 10% aqueous solution of sodium hydroxide, and was subjected to extraction with dichloromethane. The extract was washed with water, then dried over anhydrous sodium sulfate. The solvent was distilled off under reduced pressure to give 1.1 g of free base form of the title compound as colorless crystals, m.p. 88–90° C. To 0.3 g of the free form of the compound was added 3 equivalents of methanolic hydrochloric acid, and methanol was distilled off to give 0.35 g of the title compound as colorless crystals, m.p. 196–201° C.

Elemental Analysis for $C_{23}H_{29}N_3O_2 \cdot 3HCl$:

Calcd.: C, 56.51; H, 6.60; N, 8.60

Found: C, 56.22; H, 6.65; N, 8.53

Example 8

Compounds shown in Table 20 were obtained by using the compound A (free base form) obtained in Example 3 or the compound obtained in Example 7 and conducting substantially the same procedure as in Example 4 (method A) or in Example 5 (method B).

TABLE 20

| Compound No. | Method | R | Z | m.p. (° C.) | Molecular formula | Elemental analysis Calcd. (Found) | | |
|---|---|---|---|---|---|---|---|---|
| | | | | | | C | H | N |
| 1 | B | $CH_2Ph$ | N | 163–167 | $C_{30}H_{35}N_2O_2 \cdot 3HCl$ | 62.23 (62.94 | 6.62 6.64 | 7.26 7.19) |
| 2 | A | Ac | N | 189–194 | $C_{25}H_{31}N_3O_3 \cdot 2HCl$ | 60.73 (60.54 | 6.73 6.65 | 8.50 8.44) |
| 3 | B | $CH_2$–C$_6$H$_4$–Cl | CH | 199–203 | $C_{31}H_{35}ClN_2O_2 \cdot 2HCl \cdot \frac{1}{2}H_2O$ | 63.65 (63.45 | 6.55 6.53 | 4.49 4.76) |
| 4 | B | $CH_2$–C$_6$H$_4$–F | CH | 209–212 | $C_{31}H_{35}FN_2O_2 \cdot 2HCl$ | 66.54 (66.40 | 6.66 6.67 | 5.01 4.93) |
| 5 | B | $CH_2$–C$_6$H$_4$–NO$_2$ | CH | 148–155 | $C_{31}H_{35}N_3O_4 \cdot 2HCl \cdot H_2O$ | 61.59 (61.63 | 6.50 6.47 | 6.95 6.94) |
| 6 | B | $CH_2$–C$_6$H$_4$–CH$_3$ | CH | 219–221 | $C_{32}H_{38}N_2O_2 \cdot 2HCl$ | 69.18 (69.02 | 7.26 7.33 | 5.04 4.90) |

Example 9

Compounds shown in Table 21 were obtained by using the compound (free base form) obtained in Example 2 and conducting substantially the same procedure as in Example 5.

TABLE 21

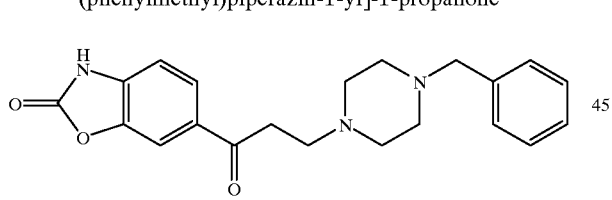

| Compound No. | R | m.p. (° C.) | Molecular formula | Elemental analysis Calcd. (Found) C | H | N |
|---|---|---|---|---|---|---|
| 1 | CH$_2$—⌬—F | 223–225 | $C_{31}H_{34}F_2N_2O_2 \cdot 2HCl$ | 64.47 (64.42 | 6.28 6.33 | 4.85 4.80) |
| 2 | CH$_2$—⌬—NO$_2$ | 150–155 | $C_{31}H_{34}N_4O_6 \cdot 2HCl$ | 58.96 (58.84 | 5.74 5.82 | 8.87 8.66) |
| 3 | CH$_2$—⌬—CH$_3$ | 205–210 | $C_{33}H_{40}N_2O_2 \cdot 2HCl$ | 69.58 (69.43 | 7.43 7.48 | 4.92 4.78) |

Example 10

1(2,3-Dihydro-2-oxobenzoxazol-6-yl)-3-[4-(phenylmethyl)piperazin-1-yl]-1-propanone Using 0.6 g of 3-chloro-1-(2,3-dihydro-2-oxobenzoxazol-6-yl)-1-propanone and 0.47 g of 1-(phenylmethyl)piperazine, 0.65 g of the title compound was obtained as colorless crystals, m.p. >300° C., in the same manner as in Example 6.

Elemental Analysis for $C_{21}H_{23}N_3O_3$:

Calcd.: C, 69.02; H, 6.34; N, 11.50

Found: C, 68.78; H, 6.37; N, 11.35

Reference Example 1

3-Chloro-1-(4-formyl-2,3,4,5-tetrahydro-1,4-benzoxazepin-7-yl)-1-propanone

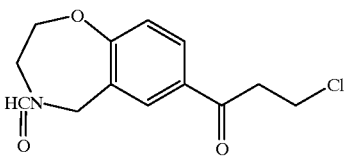

(1) To 15 ml of formic acid was added dropwise 5 ml of acetic anhydride, and the mixture was stirred for 20 minutes at room temperature. To the mixture was added dropwise a solution of 2.2 g of 2,3,4,5-tetrahydro-1,4-benzoxazepine in 10 ml of dichloromethane, and the mixture was stirred for 30 minutes at room temperature. The reaction mixture was poured into ice-water, then the mixture was subjected to extraction with dichloromethane. The extract was washed successively with a saturated aqueous solution of sodium bicarbonate, and water. The mixture was dried over anhydrous sodium sulfate, and the solvent was distilled off under reduced pressure to give 2.6 g of 4-formyl-2,3,4,5-tetrahydro-1,4-benzoxazepine as an oily anhydrous substance.

(2) To a solution of 1.7 g of 4-formyl-2,3,4,5-tetrahydro-1,4-benzoxazepine and 1.28 g of 3-chloropropionyl chloride in 20 ml of 1,2-dichloroethane was added 3.0 g of aluminum chloride by portions. The mixture was stirred for 6 hours under reflux. The reaction mixture was poured into ice-water, and the resultant was subjected to extraction with dichloromethane. The extract was washed with water, dried over anhydrous sodium sulfate, and the solvent was distilled off under reduced pressure. The residue was purified by means of silica gel column chromatography (developing solvent: ethyl acetate) to give 1.95 g of the title compound as a colorless oily substance.

Elemental Analysis for $C_{13}H_{14}ClNO_3$:
Calcd.: C, 58.32; H, 5.27; N, 5.23
Found: C, 58.41; H, 5.28; N, 5.18

Preparation Example 1

(1) 3-[1-(Phenylmethyl)piperidin-4-yl]-1-(2,3,4,5-tetrahydro-1,4-benzoxazepin-7-yl)-1-propanone dihydrochloride

| (the compound A in Example 3) | 1 g |
| (2) Lactose | 197 g |
| (3) Corn starch | 50 g |
| (4) Magnesium stearate | 2 g |

The above components (1), (2) and (3) were blended in an amount of 1 g of the component (1), 197 g of the component (2) and 20 g of the component (3), and the mixture was granulated with a paste prepared from 15 g of the component (3) and 25 ml of water. To this granular product were added 15 g of the component (3) and 2 g of the component (4), and the resulting composition was compression-molded to provide 2000 tablets each measuring 3 mm in diameter and containing 0.5 mg of the component (1).

Preparation Example 2

(1) 3-[1-(Phenylmethyl)piperidin-4-yl]-1-(2,3,4,5-tetrahydro-1,4-benzoxazepin-7-yl)-1-propanone dihydrochloride

| (the compound A in Example 3) | 2 g |
| (2) Lactose | 197 g |
| (3) Corn starch | 50 g |
| (4) Magnesium stearate | 2 g |

The above components (1), (2) and (3) were blended in an amount of 2 g of the component (1), 197 g of the component (2) and 20 g of the component (3), and the mixture was granulated with a paste prepared from 15 g of the component (3) and 25 ml of water. To this granular product were added 15 g of the component (3) and 2 g of the component (4), and the resulting composition was compression-molded to provide 2000 tablets each measuring 3 mm in diameter and containing 1.0 mg of the component (1).

Experimental Example 1

The cholinesterase inhibitory activity of the compound of this invention was assayed with (acetyl[$^3$H])-acetylcholine. More specifically, (acetyl[$^3$H])-acetylcholine as the substrate and the compound of this invention as the test sample were added to the $S_1$ fraction of a homogenate of male Wistar rat cerebral cortex as the cholinesterase source. The mixture was incubated for 30 minutes, after completion of the reaction, to the reaction mixture was added a toluene-based scintillator, and the mixture was shaken. The reaction product [$^3$H]-acetic acid was transferred to the toluene layer, which was subjected to determination of cholinesterase inhibitory activity by counting with a liquid scintillation counter.

The cholinesterase inhibitory activity of the test compound was expressed in 50% inhibitory concentration ($IC_{50}$). The cholinesterase inhibitory activity of physostigmine was also determined by the same procedure. The results are shown in Table 22.

TABLE 22

| Compound No. (Example No.) | Acetylcholinesterase inhibitory activity $IC_{50}$ ($\mu$M) |
| --- | --- |
| 3-A | 0.0175 |
| 3-B | 0.119 |
| 4 | 0.0545 |
| 5 | 0.0696 |
| 6 | 0.107 |
| 8-5 | 0.0127 |
| physostigmine | 0.220 |

The results shown in Table 22 indicate that the compounds of the present invention have superior cholinesterase inhibitory activity to physostigmine. Thus the compounds of the present invention have an excellent cholinesterase inhibitory activity and are useful as therapeutic/prophylactic medicament of senile dementia.

Experimental Example 2

The antidepressant activity of the compound of the present invention was assayed by means of tail suspension test using ICR male mice (five weeks of age, weighing 23.5 to 37.6 g) as test animals. Test compound was dissolved in saline solution or suspended in 5% arabic gum solution and administered orally to the test mice in a dose of 30 mg/kg. Thirty minutes later, the mice were suspended on tails for 10 minutes and immobility thereof (% control) was measured. The antidepressant activity of the test compound was shown as in percent control of immobility. As a comparative compound, desipramine, which is known to have an antidepressant activity, was employed and the immobility thereof was measured in the same manner as described above. The results are shown in Table 23.

TABLE 23

| Compound No. (Example No.) | n | Immobility (%) (% control) |
| --- | --- | --- |
| Saline | 17 | 49.45 ± 2.47 |
| 3-B | 13 | 34.37 ± 4.49** |
| desipramine | 16 | 37.25 ± 3.32** |

**$P < 0.01$

As clearly shown in Table 23, the compound of the present invention has an excellent antidepressant activity relative to the reference compound, that is, desipramine.

What is claimed is:

1. A compound of the formula:

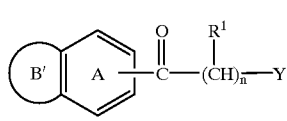

[I']

wherein ring A is an unsubstituted benzene ring or a substituted benzene ring, wherein said substituted benzene ring is substituted with 1 to 3 substituents selected from the group consisting of a $C_{1-4}$alkyl group, a halogen atom, a nitro group, a cyano group, a hydroxyl group, a $C_{1-4}$alkoxy group, a $C_{1-4}$alkoxy group $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, an aminocarbonyloxy group, a mono- or di-$C_{1-4}$alkylamino-carbonyloxy group, a $C_{1-4}$alkylsulfonylamino group, a $C_{1-4}$alkoxy-carbonyl group, a carboxyl group, a $C_{1-6}$alkyl-carbonyl group, a $C_{3-7}$cycloalkyl-carbonyl group, a carbamoyl group, a mono- or di-$C_{1-4}$alkyl-carbamoyl group, a $C_{1-6}$alkylsulfonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenylsulfonyl group, a phenyl-$C_{1-4}$alkylsulfinyl group, a phenyl-$C_{1-4}$alkylsulfonylamino group and a phenylsulfonylamino group, wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group;

ring B' is a non-aromatic heterocyclic ring represented by the following formulae:

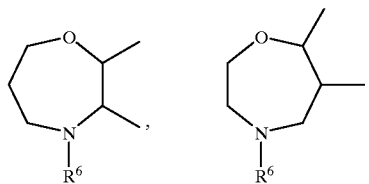

wherein $R^6$ is (1) a hydrogen atom, (2) a $C_{1-7}$ alkyl or a $C_{7-10}$ aralkyl group which may be substituted with a $C_{1-4}$ alkyl group, a halogen atom, a nitro group, a $C_{1-4}$ alkoxy group or a hydroxyl group, (3) a formyl group or (4) a $C_{2-8}$ alkylcarbonyl group;

R' is a hydrogen atom, an unsubstituted hydrocarbon group or a substituted hydrocarbon group, which may be different from one another in the repetition of n, wherein said substituted hydrocarbon group is substituted with 1 to 5 substituents selected from the group consisting of a halogen atom, a nitro group, a cyano group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, a $C_{1-4}$alkylsulfonylamino group, a $C_{1-4}$alkoxy-carbonyl group, a carboxyl group, a $C_{1-6}$alkyl-carbonyl group, a carbamoyl group, a mono- or di-$C_{1-4}$alykl-carbamoyl group, a $C_{1-6}$alkylsulfonyl group, a $C_{1-4}$alkyl group, an aminocarbonyloxy group, a mono- or di-$C_{1-4}$alkylamino-carbonyloxy group, a $C_{3-7}$cycloalkyl-carbonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenylsulfonyl group, a phenyl-$C_{1-4}$alkylsulfinyl group, a phenyl-$C_{1-4}$alkylsulfonylamino group and a phenylsulfonylamino group, wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group;

Y is an unsubstituted amino group, a substituted amino group, an unsubstituted N-containing saturated heterocyclic group, or a substituted N-containing saturated heterocyclic group, wherein said substituted amino group is substituted with 1 to 2 substituents selected from the group consisting of a hydrogen atom, an unsubstituted hydrocarbon group, said substituted hydrocarbon group of $R^1$, an unsubstituted acyl group and a substituted acyl group, wherein said substituted acyl group is substituted with 1 to 3 substituents selected from the group consisting of a halogen atom, a nitro group, a hydroxy group, an amino group, a mono- or di-$C_{1-6}$alkylamino group and a $C_{1-4}$alkoxy group, and said substituted N-containing saturated heterocyclic group is substituted with 1 to 5 substituents selected from the group consisting of an unsubstituted hydrocarbon group, said substituted hydrocarbon group of $R^1$, an unsubstituted acyl group, said substituted acyl group for said substituted amino group of Y, a halogen atom, a nitro group, a cyano group, an oxo group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 of hetero atoms selected from the group consisting of nitrogen, oxygen and sulfur atoms, a $C_{1-4}$alkyl-carbonylamino group, a $C_{1-4}$alkylsulfonylamino group, a $C_{1-4}$alkoxy-carbonyl group a phenyl-$C_{1-4}$alkyloxycarbonyl group, a carboxyl group, a C$_{1-6}$alkyl-carbonyl group, benzoyl group, a substituted benzoyl group, a carbamoyl group, a mono- or di-C$_{1-4}$alkyl-carbamoyl group and a C$_{1-6}$alkylsulfonyl group
wherein said substituted benzoyl group is substituted with 1 to 3 substituents selected from the group consisting of a C$_{1-4}$alkyl group, a halogen atom, a C$_{1-4}$alkoxy group, a mono- or di-C$_{1-4}$alkylamine, a 5- to 7-membered cyclic amino group, a nitro group and a hydroxyl group; and n denotes an integer of 2; or a salt thereof.

2. A compound as claimed in claim 1, wherein R$^1$ is a hydrogen atom or a chain-like or cyclic or their combined type unsubstituted C$_{1-18}$ hydrocarbon group or C$_{1-18}$ hydrocarbon substituted with 1 to 5 substituents selected from the group consisting of said substituent for said hydrocarbon of R$^1$;

Y is (1) a group shown by the formula:

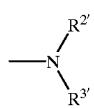

(VII)

wherein R$^{2'}$ and R$^{3'}$ each represents a hydrogen atom, an unsubstituted hydrocarbon group, a substituted hydrocarbon group an unsubstituted acyl group, or a substituted acyl group,
wherein said substituted hydrocarbon group is substituted with 1 to 5 substituents selected from the group consisting of said substituent for hydrocabon of R$^1$, and
said substituted acyl group is substituted with 1 to 3 substituents selected from the group consisting of a halogen atom, a nitro group, a hydroxy group, an amino group, a mono- or di-C$_{1-6}$alkylamino group and a C$_{1-4}$alkoxy group, or (2) an unsubstituted 5- to 9-membered N-containing heterocyclic group having 1 to 3 of hetero atoms or a substituted 5- to 9-membered N-containing heterocyclic group having 1 to 3 of hetero atoms,
wherein said substituted N-containing heterocyclic group is substituted with 1 to 5 substituents selected from the group consisting of said hydrocarbon group of R$^1$, an unsubstituted acyl group, said substituted acyl group for R$^{2'}$ and R$^{3'}$, a halogen atom, a nitro group, a cyano group, an oxo group, a hydroxyl group, a C$_{1-4}$alkoxy group, a C$_{1-4}$alkylthio group, an amino group, a mono- or di-C$_{1-4}$alkylamino group, a 5- to 7-membered cyclic amino group which may have, other than carbon atoms and one nitrogen atom, 1 to 3 of hetero atoms selected from the group consisting of nitrogen, oxygen and sulfur atoms, a C$_{1-4}$alkyl-carbonylamino group, a C$_{1-4}$alkylsulfonylamino group, a C$_{1-4}$alkoxy-carbonyl group, a phenyl-C$_{1-4}$alkyl-oxycarbonyl group, a carboxyl group, a C$_{1-6}$alkyl-carbonyl group, benzoyl group, and a substituted benzoyl group, a carbamoyl group, a mono- or di-C$_{1-4}$alkyl-carbamoyl group and a C$_{1-6}$alkylsulfonyl group,
wherein said substituted benzoyl group is substituted with 1 to 3 substituents selected from the group consisting of a C$_{1-4}$alkyl group, a halo-gen atom, a C$_{1-4}$alkoxy group, a mono- or di-C$_{1-4}$alkylamine, a 5- to 7-membered cyclic amino group, a nitro group and a hdroxyl group.

3. A compound as claimed in claim 1, wherein R$^1$ is (1) a hydrogen atom, (2) a straight-chain or branched C$_{1-11}$ alkyl, C$_{2-6}$ alkenyl or C$_{2-6}$ alkynyl group which may be substituted with 1 to 5 substituents selected from the group consisting of a halogen atom, a nitro group, a cyano group, a hydroxyl group, a C$_{1-4}$ alkoxy group, a C$_{1-4}$ alkylthio group, an amino group, a mono- or di-C$_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a C$_{1-4}$ alkyl-carbonylamino group, a C$_{1-4}$ alkylsulfonylamino group, a C$_{1-4}$ alkoxy-carbonyl group, a carboxyl group, a C$_{1-6}$ alkyl-carbonyl group, a carbamoyl group, a mono- or di-C$_{1-4}$ alkyl-carbamoyl group and a C$_{1-6}$ alkylsulfonyl group, (3) a C$_{3-7}$ monocyclic cycloalkyl group which may be substituted with 1 to 5 substituents selected from the group consisting of a halogen atom, a nitro group, a cyano group, a hydroxyl group, a C$_{1-4}$ alkoxy group, a C$_{1-4}$ alkylthio group, an amino group, a mono- or di-C$_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a C$_{1-4}$ alkyl-carbonylamino group, a C$_{1-4}$ alkylsulfonylamino group, a C$_{1-4}$ alkoxy-carbonyl group, a carboxyl group, a C$_{1-6}$ alkyl-carbonyl group, a carbamoyl group, a mono- or di-C$_{1-4}$ alkyl-carbamoyl group and a C$_{1-6}$ alkylsulfonyl group, (4) a C$_{8-14}$ bridge ring saturated hydrocarbon group which may be substituted with 1 to 5 substituents selected from the group consisting of a halogen atom, a nitro group, a cyano group, a hydroxyl group, a C$_{1-4}$ alkoxy group, a C$_{1-4}$ alkylthio group, an amino group, a mono- or di-C$_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a C$_{1-4}$ alkyl-carbonylamino group, a C$_{1-4}$ alkylsulfonylamino group, a C$_{1-4}$ alkoxy-carbonyl group, a carboxyl group, a C$_{1-6}$ alkyl-carbonyl group, a carbamoyl group, a mono- or di-C$_{1-4}$ alkyl-carbamoyl group and a C$_{1-6}$ alkylsulfonyl group, (5) a C$_{6-14}$ aryl group which may be substituted with 1 to 5 substituents selected from the group consisting of a C$_{1-4}$ alkyl group, a halogen atom, a nitro group, a cyano group, a hydroxyl group, a C$_{1-4}$ alkoxy group, a C$_{1-4}$ alkylthio group, an amino group, a mono- or di-C$_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a C$_{1-4}$ alkyl-carbonylamino group, an aminocarbonyloxy group, a mono- or di-C$_{1-4}$ alkylamino-carbonyloxy group, a C$_{1-4}$ alkylsulfonylamino group, a C$_{1-4}$ alkoxy-carbonyl group, a carboxyl group, a C$_{1-6}$ alkyl-carbonyl group, a C$_{3-7}$ cycloalkyl-carbonyl group, a carbamoyl group, a mono- or di-C$_{1-4}$ alkyl-carbamoyl group, a C$_{1-6}$ alkylsulfonyl group, a C$_{3-7}$ cycloalkylsulfonyl group, and a phenyl, naphthyl, mono- or di-phenyl-C$_{1-3}$ alkyl, phenoxy, benzoyl, phenoxycarbonyl, benzylcarbonyl, phenyl-C$_{1-4}$ alkylcarbamoyl, phenylcarbamoyl, phenyl-C$_{1-4}$ alkyl-carbonylamino, benzoylamino, phenyl-C$_{1-4}$ alkylsulfonyl, phenylsulfonyl, phenyl-C$_{1-4}$ alkylsulfinyl, phenyl-C$_{1-4}$ alkylsulfonylamino or phenylsulfonylamino group which may be substituted with 1 to 4 substituents selected from the group consisting of a $C_{1-4}$ alkyl group, a $C_{1-4}$ alkoxy group, a halogen atom, a hydroxyl group, a benzyloxy group, an amino group, a mono- or di-$C_{1-4}$ alkylamino group, a nitro group, a $C_{1-6}$ alkyl-carbonyl group and benzoyl group, or (6) a $C_{7-18}$ aralkyl, $C_{6-14}$ aryl-$C_{2-12}$ alkenyl, $C_{6-14}$ aryl-$C_{2-12}$ alkynyl or $C_{3-7}$ cycloalkyl-$C_{1-6}$ alkyl group which may be substituted with 1 to 5 substituents selected from the group consisting of a $C_{1-4}$ alkyl group, a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$ alkyl-carbonylamino group, an aminocarbonyloxy group, a mono- or di-$C_{1-4}$ alkylamino-carbonyloxy group, a $C_{1-4}$ alkylsulfonylamino group, a $C_{1-4}$ alkoxy-carbonyl group, a carboxyl group, a $C_{1-6}$ alkyl-carbonyl group, a $C_{3-7}$ cycloalkyl-arbonyl group, a carbamoyl group, a mono- or di-$C_{1-4}$ alkyl-carbamoyl group, a $C_{1-6}$ alkylsulfonyl group, a $C_{3-7}$ cycloalkylsulfonyl group, and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino group, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino group which may be substituted with 1 to 4 substituents selected from the group consisting of a $C_{1-4}$ alkyl group, a $C_{1-4}$ alkoxy group, a halogen atom, a hydroxyl group, a benzyloxy group, an amino group, a mono- or di-$C_{1-4}$ alkylamino group, a nitro group, a $C_{1-6}$ alkylcarbonyl group and a benzoyl group;

Y is (a) an amino group which may be substituted with 1 or 2 substituents selected from the group consisting of (1) a straight-chain or branched $C_{1-11}$ alkyl, $C_{2-6}$ alkenyl or $C_{2-6}$ alkynyl group which may be substituted with 1 to 5 substituents selected from the group consisting of a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$ alkyl arbonylamino group, a $C_{1-4}$ alkylsulfonylamino group, a $C_{1-4}$ alkoxyarbonyl group, a carboxyl group, a $C_{1-6}$ alkyl-carbonyl group, a carbamoyl group, a mono- or di-$C_{1-4}$ alkyl-carbamoyl group and a $C_{1-6}$ alkylsulfonyl group, (2) a $C_{3-7}$ monocyclic cycloalkyl group which may be substituted with 1 to 5 substituents selected from the group consisting of a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$ alkyl-carbonylamino group, a $C_{1-4}$ alkylsulfonylamino group, a $C_{1-4}$ alkoxy-carbonyl group, a carboxyl group, a $C_{1-6}$ alkyl-carbonyl group, a carbamoyl group, a mono- or di-$C_{1-4}$ alkyl-carbamoyl group and a $C_{1-6}$ alkylsulfonyl group, (3) a $C_{8-14}$ bridge ring saturated hydrocarbon group which may be substituted with 1 to 5 substituents selected from the group consisting of a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$ alkyl-carbonylamino group, a $C_{1-4}$ alkylsulfonylamino group, a $C_{1-4}$ alkoxy-carbonyl group, a carboxyl group, a $C_{1-6}$ alkyl-carbonyl group, a carbamoyl group, a mono- or di-$C_{1-4}$ alkyl-carbamoyl group and a $C_{1-6}$ alkylsulfonyl group, (4) a $C_{6-14}$ aryl group which may be substituted with 1 to 5 substituents selected from the group consisting of a $C_{1-4}$ alkyl group, a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the soup consisting of nitrogen, oxygen and sulfur atoms, a $C_{1-4}$ alkyl-carbonylamino group, an aminocarbonyloxy group, a mono- or di-$C_{1-4}$ alkylamino-carbonyloxy group, a $C_{1-4}$ alkylsulfonylamino group, a $C_{1-4}$ alkoxy-carbonyl group, a carboxyl group, a $C_{1-6}$ alkyl-carbonyl group, a $C_{3-7}$cycloalkyl-carbonyl group, a carbamoyl group, a mono- or di-$C_{1-4}$ alkyl-carbamoyl group, a $C_{1-6}$ alkylsulfonyl group, a $C_{3-7}$ cycloalkylsulfonyl group, and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino group which may be substituted with 1 to 4 substituents selected from the group consisting of a $C_{1-4}$ alkyl group, a $C_{1-4}$ alkoxy group, a halogen atom, a hydroxyl group, a benzyloxy group, an amino group, a mono- or di-$C_{1-4}$ alkylamino group, a nitro group, a $C_{1-6}$ alkyl-carbonyl group and a benzoyl group, (5) a $C_{7-18}$ aralkyl, $C_{6-14}$ aryl-$C_{3-12}$ alkenyl, $C_{6-14}$ aryl-$C_{2-12}$ alkynyl or $C_{3-7}$ cycloalkyl-$C_{1-6}$ alkyl group which may be substituted with 1 to 5 substituents selected from the group consisting of a $C_{1-4}$ alkyl group, a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$ alkyl-carbonylamino group, an aminocarbonyloxy group, a mono- or di-$C_{1-4}$ alkylamino-carbonyloxy group, a $C_{1-4}$ alkylsulfonylamino group, a $C_{1-4}$ alkoxy-carbonyl group, a carboxyl group, a $C_{1-6}$ alkyl-carbonyl group, a $C_{3-7}$ cycloalkyl-carbonyl group, a carbamoyl group, a mono- or di-$C_{1-4}$ alkyl-carbamoyl group, a $C_{1-6}$ alkylsulfonyl group, a $C_{3-7}$ cycloalkylsulfonyl group, and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino group, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino group which may be substituted with 1 to 4 substituents selected from the group consisting of a $C_{1-4}$ alkyl group, a $C_{1-4}$ alkoxy group, a halogen atom, a hydroxyl group, a benzyloxy group, an amino group, a mono- or di-$C_{1-4}$ alkylamino group, a nitro group, a $C_{1-6}$ alkyl-carbonyl group and benzoyl group, and (6) an acyl group which may be substituted with 1 to 3 substituents selected from the group consisting of a halogen atom, a nitro group, a hydroxyl group, an amino group, a mono- or di-$C_{1-6}$ alkylamino group and a $C_{1-4}$ alkoxy group, or (b) a 5- to 9-membered N-containing saturated heterocyclic group which may have, other than carbon atoms and one nitrogen atom, 1 to 3 hetero atoms selected from the group consisting of nitrogen, oxygen and sulfur atoms which may be substituted with 1 to 5 substituents selected from the group consisting of (1) a straight-chain or branched $C_{1-11}$ alkyl, $C_{2-6}$ alkenyl or $C_{2-6}$ alkynyl group which may be substituted with 1 to 5 substituents selected from the group consisting of a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$ alkyl-carbonylamino group, a $C_{1-4}$ alkylsulfonylamino group, a $C_{1-4}$ alkoxy-carbonyl group, a carboxyl group, a $C_{1-6}$ alkyl-carbonyl group, a carbamoyl group, a mono- or di-$C_{1-4}$ alkyl-carbamoyl group and a $C_{1-6}$ alkylsulfonyl group, (2) a $C_{3-7}$ monocyclic cycloalkyl group which may be substituted with 1 to 5 substituents selected from the group consisting of a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$ alkyl-carbonylamino group, a $C_{1-4}$ alkylsulfonylamino group, a $C_{1-4}$ alkoxy-carbonyl group, a carboxyl group, a $C_{1-6}$ alkyl-carbonyl group, a carbamoyl group, a mono- or di-$C_{1-4}$ alkyl-carbamoyl group and a $C_{1-6}$ alkylsulfonyl group, (3) a $C_{8-14}$ bridge ring saturated hydrocarbon group which may be substituted with 1 to 5 substituents selected from the group consisting of a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$ alkyl-carbonylamino group, a $C_{1-4}$ alkylsulfonylamino group, a $C_{1-4}$ alkoxy-carbonyl group, a carboxyl group, a $C_{1-6}$ alkyl-carbonyl group, a carbamoyl group, a mono- or di-$C_{1-4}$ alkyl-carbamoyl group and a $C_{1-6}$ alkylsulfonyl group, (4) a $C_{6-14}$ aryl group which may be substituted with 1 to 5 substituents selected from the group consisting of a $C_{1-4}$ alkyl group, a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$ alkyl-carbonylamino group, an aminocarbonyloxy group, a mono- or di-$C_{1-4}$ alkylamino-carbonyloxy group, a $C_{1-4}$ alkylsulfonylamino group, a $C_{1-4}$ alkoxy-carbonyl group, a carboxyl group, a $C_{1-6}$ alkyl-carbonyl group, a $C_{3-7}$ cycloalkyl-carbonyl group, a carbamoyl group, a mono- or di-$C_{1-4}$ alkyl-carbamoyl group, a $C_{1-6}$ alkylsulfonyl group, a $C_{3-7}$ cycloalkylsulfonyl group, and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkysulfinyl, phenyl-$C_{1-4}$ alkylsulfonylamino or phenylsulfonylamino group which may be substituted with 1 to 4 substituents selected from the group consisting of a $C_{1-4}$ alkyl group, a $C_{1-4}$ alkoxy group, a halogen atom, a hydroxyl group, a benzyloxy group, an amino group, a mono- or di-$C_{1-4}$ alkylamino group, a nitro group, a $C_{1-6}$ alkyl-carbonyl group and benzoyl group, (5) a $C_{7-18}$ aralkyl, $C_{6-14}$ aryl-$C_{2-12}$ alkenyl, $C_{6-14}$ aryl-$C_{2-12}$ alkynyl or $C_{3-7}$ cycloalkyl-$C_{1-6}$ alkyl group which may be substituted with 1 to 5 substituents selected from the group consisting of a $C_{1-4}$ alkyl group, a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$ alkyl-carbonylamino group, an aminocarbonyloxy group, a mono- or di-$C_{1-4}$ alkylamino-carbonyloxy group, a $C_{1-4}$ alkylsulfonylamino group, a $C_{1-4}$ alkoxy-carbonyl group, a carboxyl group, a $C_{1-6}$ alkylcarbonyl group, a $C_{3-7}$ cycloalkyl-carbonyl group, a carbamoyl group, a mono- or di-$C_{1-4}$ alkyl-carbamoyl group, a $C_{1-6}$ alkylsulfonyl group, a $C_{3-7}$ cycloalkylsulfonyl group, and a phenyl, naphthyl, mono- or di-phenyl-$C_{1-3}$ alkyl, phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkyl-sulfonyl, phenylsulfonyl, phenyl-$C_{1-4}$ alkylsulfinyl, phenyl-$C_{1-4}$ alkylsulfonylamino or phenylsulfonylamino group which may be substituted with 1 to 4 substituents selected from the group consisting of a $C_{1-4}$ alkyl group, a $C_{1-4}$ alkoxy group, a halogen atom, a hydroxyl group, a benzyloxy group, an amino group, a mono- or di-$C_{1-4}$ alkylamino group, a nitro group, a $C_{1-6}$ alkyl-carbonyl group and benzoyl group, (6) an acyl group which may be substituted with 1 to 3 substituents selected from the group consisting of a halogen atom, a nitro group, a hydroxyl group, an amino group, a mono- or di-$C_{1-6}$ alkylamino group and a $C_{1-4}$ alkoxy group, (7) a halogen atom, (8) a nitro group, (9) a cyano group, (10) an oxo group, (11) a hydroxyl group, (12) a $C_{1-4}$ alkoxy group, (13) a $C_{1-4}$ alkylthio group, (14) an amino group, (15) a mono- or di-$C_{1-4}$ alkylamino group, (16) a 5- to 7-membered cyclic amino group which may have, other than carbon atoms and one nitrogen atom, 1 to 3 hetero atoms selected from the group consisting of nitrogen, oxygen and sulfur atoms, (17) a $C_{1-4}$ alkyl-carbonylamino group, (18)

a $C_{1-4}$ alkylsulfonylamino group, (19) a $C_{1-4}$ alkoxy-carbonyl group, (20) a phenyl-$C_{1-4}$ alkoxy-carbonyl group, (21) a carboxyl group, (22) a $C_{1-6}$ alkyl-carbonyl group, (23) a benzoyl group which may be substituted with 1 to 3 substituents selected from the group consisting of a $C_{1-4}$ alkyl group, a halogen atom, a $C_{1-4}$ alkoxy group, a mono- or di-$C_{1-4}$ alkylamino group, a 5- to 7-membered cyclic amino group, a nitro group and a hydroxyl group, (24) a carbamoyl group, (25) a mono- or di-$C_{1-4}$ alkyl-carbamoyl group and (26) a $C_{1-6}$ alkylsulfonyl group;

ring A is a benzene ring which may be substituted with 1 to 3 substituents selected from the group consisting of a $C_{1-4}$ alkyl group, a halogen atom, a nitro group, a cyano group, a hydroxyl group, a $C_{1-4}$ alkoxy group, a $C_{1-4}$ alkylthio group, an amino group, a mono- or di-$C_{1-4}$ alkylamino group, a 5- to 7-membered cyclic amino group which may have, other than carbon atoms and one nitrogen atom, 1 to 3 of hetero atoms selected from the group consisting of nitrogen, oxygen and sulfur atoms, a $C_{1-4}$ alkyl-carbonylamino group, an aminocarbonyloxy group, a mono- or di-$C_{1-4}$ alkylamino-carbonyloxy group, a $C_{1-4}$ alkyl-sulfonylamino group, a $C_{1-4}$ alkoxy-carbonyl group, a carboxyl group, a $C_{1-6}$ alkyl-carbonyl group, a $C_{3-7}$ cycloalkyl-carbonyl group, a carbamoyl group, a mono- or di-$C_{1-4}$ alkyl-carbamoyl group, a $C_{1-6}$ alkyl-sulfonyl group, a $C_{3-7}$ cycloalkylsulfonyl group, and a phenyl, naphthyl, mono- or di-phenyl-$C_{1-3}$ alkyl, phenoxy, benzoyl, phenoxy-carbonyl, benzylcarbonyl, phenyl-$C_{1-4}$ alkyl-carbamoyl, phenyl-carbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkyl-sulfonylamino or phenylsulfonylamino group which may be substituted with 1 to 4 substituents selected from the group consisting of a $C_{1-4}$ alkyl group, a $C_{1-4}$ alkoxy group, a halogen atom, a hydroxyl group, a benzyloxy group, an amino group, a mono- or di-$C_{1-4}$ alkylamino group, a nitro group, a $C_{1-6}$ alkyl-carbonyl group and a benzoyl group.

4. A compound as claimed in claim 1, wherein ring A is an unsubstituted benzene ring.

5. A compound as claimed in claim 1, wherein $R^1$ is H.

6. A compound as claimed in claim 1, wherein Y is (1) a group shown by the formula:

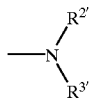

(VII)

wherein one of $R^{2'}$ and $R^{3'}$ is a straight-chain or branched $C_{1-7}$ alkyl group and the other is a $C_{7-10}$ aralkyl group, or (2) an unsubstituted 5- to 9-membered N-containing saturated heterocyclic group which may have, other than carbon atoms and one nitrogen atom, 1 to 2 of hetero atoms selected from the group consisting of nitrogen, oxygen and sulfur atoms, or a substituted 5- to 9-membered N-containing saturated heterocyclic group which may have, other than carbon atoms and one nitrogen atom, 1 to 2 of hetero atoms selected from the group consisting of nitrogen, oxygen and sulfur atoms, wherein said substituted 5- to 9-membered N-containing saturated heterocyclic group is substituted with 1 to 5 substituents selected from the group consisting of said hydrocarbon group of $R^1$, an unsubstituted acyl group, said substituted acyl group for said substituted amino group of Y, a halogen atom, a nitro group, a cyano group, an oxo group, a hydroxyl group, a $C_{1-4}$alkoxy group, a $C_{1-4}$alklthio group, an amino group, a mono- or di-$C_{1-4}$alkylamino group, a 5- to 7-membered cyclic amino group which may have, other than carbon atoms and one nitrogen atom, 1 to 3 of hetero atoms selected from the group consisting of nitrogen, oxygen and sulfur atoms, a $C_{1-4}$alkyl-carbonylamino group, a $C_{1-4}$alkylsulfonylamino group, a $C_{1-4}$alkoxy-carbonyl group, a phenyl-$C_{1-4}$alkyl-oxycarbonyl group, a carboxyl group, a $C_{1-6}$alkyl-carbonyl group, benzoyl group, a substituted benzoyl group, a carbamoyl group, a mono- or di-$C_{1-4}$alkyl-carbamoyl group and a $C_{1-6}$alkylsulfonyl group wherein said substituted benzoyl group is substituted with 1 to 3 substituents selected from the group consisting of a $C_{1-4}$alkyl group, a halogen atom, a $C_{1-4}$alkoxy group, a mono- or di-$C_{1-4}$alkylamine, a 5- to 7-membered cyclic amino group, a nitro group and a hydroxyl group.

7. A compound as claimed in claim 6, wherein said 5- to 9-membered N-containing saturated heterocyclic group is a group shown by the formula:

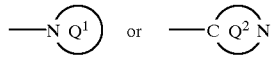

wherein ring $Q^1$ and ring $Q^2$ are respectively a 5- to 9-membered N-containing heterocyclic group which may have, other than carbon atoms and one nitrogen atom, 1 to 2 of hetero atoms selected from nitrogen, oxygen and sulfur atoms.

8. A compound as claimed in claim 7, wherein said N-containing heterocyclic group is a 5- to 7-membered heterocyclic group.

9. A compound as claimed in claim 7, wherein said heterocyclic group has one nitrogen atom constituting the ring except at the bonding position.

10. A compound as claimed in claim 9, wherein said heterocyclic group is an unsubstituted one or substituted on said ring-constituting nitrogen atom with a hydrogen atom, an unsubstituted acyl group, said substituted acyl group for said substituted amino group of Y, an unsubstituted aralkyl group or a substituted aralkyl group, wherein said substituted aralkyl group is substituted with 1 to 5 substituents selected from the group consisting of a $C_{1-4}$alkyl group, a halogen atom, a nitro group, a cyano group, a hydroxyl group, a $C_{1-4}$alkoxy group, a $C_{1-4}$alkylthio group, an amino group, a mono- or di-$C_{1-4}$alkylamino group a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, an aminocarbonyloxy group, a mono- or di-$C_{1-4}$alkylamino-carbonyloxy group, a $C_{1-4}$alkylsulfonylamino group, a $C_{1-4}$alkoxy-carbonyl group, a carboxyl group, a $C_{1-6}$alkyl-carbonyl group, a $C_{3-7}$cycloalkyl-carbonyl group, a carbamoyl group, a mono- or di-$C_{1-4}$alkyl-carbamoyl group, a $C_{1-6}$alkylsulfonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$ alkylsulfonyl group, a phenylsulfonyl group, a phenyl-$C_{1-4}$alkylsulfinyl group, a phenyl-$C_{1-4}$alkylsulfonylamino group and a phenylsulfonylamino group, wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group.

11. A compound as claimed in claim 9, wherein said heterocyclic group is an unsubstituted one or substituted on said ring-constituting nitrogen atom with a hydrogen atom, formyl, a $C_{1-6}$ alkyl-carbonyl group or a $C_{7-10}$ aralkyl group which may be substituted with a $C_{1-4}$ alkyl group, a halogen atom, a nitro group, a $C_{1-4}$ alkoxy group or a hydroxyl group.

12. A compound as claimed in claim 1, wherein $R^1$ is H; the ring A is an unsubstituted benzene ring; the ring B' is a non-aromatic heterocyclic ring represented by the following formulae:

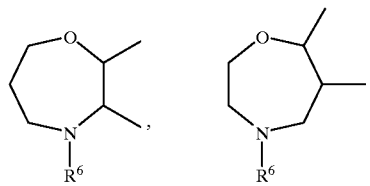

wherein $R^6$ is (1) a hydrogen atom, (2) a $C_{1-7}$ alkyl or a $C_{7-10}$ aralkyl group which may be substituted with a $C_{1-4}$ alkyl group, a halogen atom, a nitro group, a $C_{1-4}$ alkoxy group or a hydroxyl group, (3) a formyl group or (4) a $C_{2-8}$ alkylcarbonyl group; and Y is an unsubstituted 5- to 9-membered N-containing saturated heterocyclic group which may have, other than carbon atoms and one nitrogen atom, 1 to 2 hetero atoms selected from the group consisting of nitrogen, oxygen and sulfur atoms, or a substituted 5- to 9-membered N-containing saturated heterocyclic group which may have, other than carbon atoms and one nitrogen atom, 1 to 2 hetero atoms selected from the group consisting of nitrogen, oxygen and sulfur atoms wherein said substituted 5- to 9-membered N-containing saturated heterocyclic group is substituted with an unsubstituted acyl group, said substituted acyl group for said substituted amino group of Y, an unsubstituted aralkyl group or a substituted aralkyl group, wherein said substituted aralkyl group is substituted with 1 to 5 substituent selected from the group consisting of a $C_{1-4}$alkyl group, a halogen atom, a nitro group, a cyano group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, an aminocarbonyloxy group, a mono- or di-$C_{1-4}$alkylamino-carbonyloxy group, a $C_{1-4}$alkylsulfonylamino group, a $C_{1-4}$alkoxy-carbonyl group, a carboxyl group, a $C_{1-6}$alkyl-carbonyl group, a $C_{3-7}$cycloalkyl-carbonyl group, a carbamoyl group, a mono- or di-$C_{1-4}$alkyl-carbamoyl group, a $C_{1-6}$alkylsulfonyl group, a $C_{3-7}$cycloalkylsulfonyl group, phenyl group, naphthyl group a mono- or di-phenyl-$C_{1-3}$alkyl group, a phenoxy group, a benzoyl group, a phenoxycarbonyl group, a benzylcarbonyl group, a phenyl- $C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl groups, a phenylsulfonyl group, a phenyl-$C_4$alkylsulfonyl group, a phenyl-$C_{1-4}$alkylsulfonylamino group and a phenylsulfonylamino group, wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an amino groups a mono- or di-$C_{1-4}$alkylamino group, a nitro group, a $C_{1-6}$alkyl-carbonyl group and a benzoyl group.

13. A compound as claimed in claim 12, wherein $R^6$ in the ring B' is a $C_{7-10}$ aralkyl group which may be substituted with a $C_{1-4}$ alkyl group, a halogen atom, a nitro group, a hydroxyl group or a $C_{1-4}$ alkoxy group; said 5- to 9-membered N-containing saturated heterocyclic group in Y may have, other than carbon atoms and one nitrogen atom, one hetero atom selected from the group consisting of nitrogen, oxygen and sulfur atom, and said substituent in Y may be substituted with a $C_{1-4}$ alkyl group, a halogen atom, a nitro group, a hydroxyl group or a $C_{1-4}$ alkoxy group.

14. A compound as claimed in claim 1, which is selected from the group consisting of (1) 3-[1-(phenylmethyl)piperidin-4-yl]-1-(2,3,4,5-tetrahydro-1,4-benzoxazepin-7-yl)-1-propanone or a salt thereof, (2) 1-[4-(phenylmethyl)-2,3,4,5-tetrahydro-1,4-benzoxazepin-7-yl]-3-[1-(phenylmethyl)piperidin-4-yl]-1-propanone or a salt thereof, (3) 1-(4-acetyl-2,3,4,5-tetrahydro-1,4-benzoxazepin-7-yl)-3-[1-(phenylmethyl)piperidin-4-yl]-1-propanone or a salt thereof, (4) 1-[4-(4-methoxyphenylmethyl)-2,3,4,5-tetrahydro-1,4-benzoxazepin-7-yl]-3-[1-(phenylmethyl)piperidin-4-yl]-1-propanone or a salt thereof, (5) 1-(4-formyl-2,3,4,5-tetrahydro-1,4-benzoxazepin-7-yl)-3-[4-(phenylmethyl)piperazin-1-yl]-1-propanone or a salt thereof, and (6) 1-[4-(4-nitrophenylmethyl)-2,3,4,5-tetrahydro-1,4-benzoxazepin-7-yl]-3-[1-(phenylmethyl)piperidin-4-yl]-1-propanone or a salt thereof.

15. A compound of the formula:

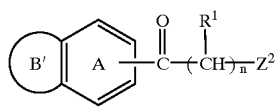

[IV]

wherein ring A is an unsubstituted benzene ring or a substituted benzene ring
wherein said substituted benzene ring is substituted with 1 to 3 substituents selected from the group consisting of a $C_{1-4}$alkyl group, a halogen atom, a nitro group, a cyano group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, an aminocarbonyloxy group, a mono- or di-$C_{1-4}$alkylamino-carbonyloxy group, a $C_{1-4}$alkylsulfonylamino group, a $C_{1-4}$alkoxy-carbonyl group, a carboxyl group, a $C_{1-6}$alkyl-carbonyl group, a $C_{3-7}$cycloalkyl-carbonyl group, a carbamoyl group, a mono- or di-$C_{1-4}$alkyl-carbamoyl group, a $C_{1-6}$alkylsulfonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenylsulfonyl group, a phenyl-$C_{1-4}$alkylsulfinyl group, a phenyl-$C_{1-4}$alkylsulfonylamino group and a phenylsulfonylamino group,
wherein each phenyl group or naphthyl group in the substituents may be substituted with 1 to 4 substituents selected from the group consisting of $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group;
ring B' is a non-aromatic heterocyclic ring represented by the following formulae:

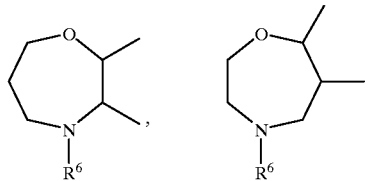

wherein $R^6$ is (1) a hydrogen atom, (2) a $C_{1-7}$ alkyl or a $C_{7-10}$ aralkyl group which may be substituted with a $C_{1-4}$ alkyl group, a halogen atom, a nitro group, a $C_{1-4}$ alkoxy group or a hydroxyl group, (3) a formyl group or (4) a $C_{2-8}$ alkylcarbonyl group;
$R^1$ is a hydrogen atom or, an unsubstituted hydrocarbon group or a substituted hydrocarbon group, which may be different from one another in the repetition of n, wherein said substituted hydrocarbon group is substituted with 1 to 5 substituents selected from the group consisting of a halogen atom, a nitro group, a cyano group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, a $C_{1-4}$alkylsulfonylamino group, a $C_{1-4}$alkoxy-carbonyl group, a carboxyl group, a $C_{1-6}$alkyl-carbonyl group, a carbamoyl group, a mono- or di-$C_{1-4}$alkyl-carbamoyl group, a $C_{1-6}$alkylsulfonyl group, a $C_{1-4}$alkyl group, an aminocarbonyloxy group, a mono- or di-$C_{1-4}$alkylamino-carbonyloxy group, a $C_{3-7}$cycloalkyl-carbonyl group, a $C_{3-7}$cycloalkylsulfonyl group, phenyl group, naphthyl group, a mono- or di-phenyl-$C_{3-3}$alkyl group, a phenoxy group a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenylsulfonyl group, a phenyl-$C_{1-4}$akylsulfinyl group, a phenyl-$C_{1-4}$alkylsulfonylamino group and a phenylsulfonylamino group
wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an ammo group, a mono- or di-$C_{1-4}$alkylamino group, a nitro group, a $C_{1-6}$alkyl-carbonyl group and a benzoyl group;
n denotes an integer of 2; and
$Z^2$ is a leaving group, or a salt thereof.

16. A method of producing a compound of the formula:

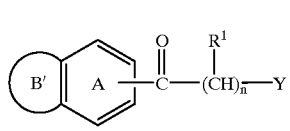

[I']

wherein ring A is an unsubstituted benzene ring or a substituted benzene ring,
wherein said substituted benzene ring is substituted with 1 to 3 substituents selected from the group consisting of a $C_{1-4}$alkyl group, a halogen atom, a nitro group, a cyano group, a hydroxyl group, a $C_{1-4}$alkoxy group, a $C_{1-4}$alkylthio group, an amino group, a mono- or di-$C_{1-4}$alklamino group, a 5- to 7-membered cyclic amino group which may have, other than carbon atoms and one nitrogen atom, 1 to 3 hetero atoms selected from the group consisting of nitrogen, oxygen and slfur atoms, a $C_{1-4}$alkyl-carbonylamino group, an aminocarbonyloxy group, a mono- or di-$C_{1-4}$alklamino-carbonyloxy group, a $C_{1-4}$alkylsulfonylamino group, a $C_{1-4}$alkoxy-carbonyl group, a carboxyl group, a $C_{1-6}$alkyl-carbonyl group, a $C_{3-7}$cycloalkyl-carbonyl group, a carbamoyl group, a mono- or di-$C_{1-4}$alkyl-carbamoyl group, a $C_{1-6}$alkylsulfonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkylcarbamoyl group, a phenylcarbamoyl group, a phenyl-$C_{1-4}$ alkyl-carbonylamino, benzoylamino group, a phenyl-$C_{1-4}$alkylsulfonyl group, a phenylsulfonyl group, a phenyl-$C_{1-4}$alkylsulfinyl group, a phenyl-$C_{1-4}$alkylsulfonylamino group and a phenylsulfonylamino group,
  wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group;
ring B' is a non-aromatic heterocyclic ring represented by the following formulae:

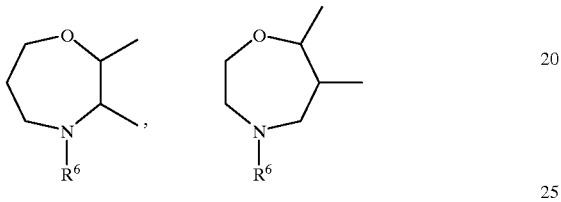

wherein $R^6$ is (1) a hydrogen atom, (2) a $C_{1-7}$ alkyl or a $C_{7-10}$ aralkyl group which may be substituted with a $C_{1-4}$ alkyl group, a halogen atom, a nitro group, a $C_{1-4}$ alkoxy group or a hydroxyl group, (3) a formyl group or (4) a $C_{2-8}$ alkylcarbonyl group;

$R^1$ is a hydrogen atom, an unsubstituted hydrocarbon group or a substituted hydrocarbon group, which may be different from one another in the repetition of n,
  wherein said substituted hydrocarbon group is substituted with 1 to 5 substituents selected from the group consisting of a halogen atom, a nitro group, a cyano group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, a $C_{1-4}$alkylsulfonylamino group, a $C_{1-4}$alkoxy-carbonyl group, a carboxyl group, a $C_{1-6}$alkyl-carbonyl group, a carbamoyl group, a mono- or di-$C_{1-4}$alkyl-carbamoyl group, a $C_{1-4}$alkylsulfonyl group, a $C_{1-4}$alkyl group, an aminocarbonyloxy group, a mono- or di-$C_{1-4}$alkylamino-carbonyloxy group, a $C_{3-7}$cycloalkyl-carbonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenylsulfonyl group, a phenyl-$C_{1-4}$alkylsulfinyl group a phenyl-$C_{1-4}$alkylsulfonylamino group and a phenylsulfonylamino group
    wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group;

Y is an unsubstituted amino group, a substituted amino group, an unsubstituted N-containing saturated heterocyclic group, or a substituted N-containing saturated heterocyclic group,
  wherein said substituted amino group is substituted with 1 to 2 substituents selected from the group consisting of a hydrogen atom, an unsubstituted hydrocarbon group, said substituted hydrocarbon group of $R^1$, an unsubstituted acyl group and a substituted acyl group,
    wherein said substituted acyl group is substituted with 1 to 3 substituents selected from the group consisting of a halogen atom, a nitro group, a hydroxy group, an amino group, a mono- or di-$C_{1-6}$alkylamino group and a $C_{1-4}$alkoxy group, and
  said substituted N-containing saturated heterocyclic group is substituted with 1 to 5 substituents selected from the group consisting of an unsubstituted hydrocarbon group, said substituted hydrocarbon group of $R^1$, an unsubstituted acyl group, said substituted acyl group for said substituted amino group of Y, a halogen atom, a nitro group, a cyano group, an oxo group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 of hetero atoms selected from the group consisting of nitrogen, oxygen and sulfur atoms, a $C_{1-4}$alkyl-carbonylamino group, a $C_{1-4}$alkylsulfonylamino group, a $C_{1-4}$alkoxy-carbonyl group, a phenyl-$C_{1-4}$alkyloxycarbonyl group, a carboxyl group, a $C_{1-6}$alkylcarbonyl group, benzoyl group, a substituted benzoyl group, a carbamoyl group, a mono- or di-$C_{1-4}$alkylcarbamoyl group and a $C_{1-6}$alkylsulfonyl group
    wherein said substituted benzoyl group is substituted with 1 to 3 substituents selected from the group consisting of a $C_{1-4}$alkyl group, a halogen atom, a $C_{1-4}$alkoxy group, a mono- or di-$C_{1-4}$alkylamine, a 5- to 7-membered cyclic amino group, a nitro group and a hydroxyl group;

n denotes an integer of 2, or a salt thereof, which comprises reacting a compound of the formula:

[II]

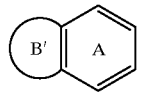

wherein the ring A and the ring B' have the same meanings as defined above, or a salt thereof, with a compound of the formula:

[III]

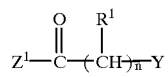

wherein $Z^1$ is a leaving group; and $R^1$, Y and n have the same meanings as defined above, or a salt thereof.

17. A method of producing a compound of the formula:

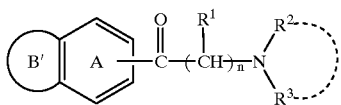

[VI]

wherein ring A is an unsubstituted benzene ring or a substituted benzene ring,
  wherein said substituted benzene ring is substituted with 1 to 3 substituents selected from the group consisting of a $C_{1-4}$alkyl group, a halogen atom, a nitro group, a cyano group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, an aminocarbonyloxy group, a mono- or di-$C_{1-4}$alkylamino-carbonyloxy group, a $C_{1-4}$alkylsulfonylamino group, a $C_{1-4}$alkoxy-carbonyl group, a carboxyl group, a $C_{1-6}$alkyl-carbonyl group, a $C_{3-7}$cycloalkyl-carbonyl group, a carbamoyl group, a mono- or di-$C_{1-4}$alkyl-carbamoyl group, a $C_{1-6}$alkylsulfonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenylsulfonyl group, a phenyl-$C_{1-4}$alkylsulfinyl group, a phenyl-$C_{1-4}$alkylsulfonylamino group and a phenylsulfonylamino group,
    wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group;
  ring B' is a non-aromatic heterocyclic ring represented by the following formulae:

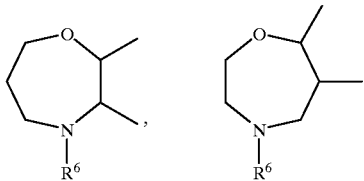

wherein $R^6$ is (1) a hydrogen atom, (2) a $C_{1-7}$ alkyl or a $C_{7-10}$ aralkyl group which may be substituted with a $C_{1-4}$ alkyl group, a halogen atom, a nitro group, a $C_{1-4}$ alkoxy group or a hydroxyl group, (3) a formyl group or (4) a $C_{2-8}$ alkylcarbonyl group;
  $R^1$ is a hydrogen atom, an unsubstituted hydrocarbon group or a substituted hydrocarbon group, which may be different from one another in the repetition of n,
    wherein said substituted hydrocarbon group is substituted with 1 to 5 substituents selected from the group consisting of a halogen atom, a nitro group, a cyano group, a hydroxyl group, a $C_{1-4}$alkoxy group, a $C_{1-4}$alkylthio group, an amino groups a mono- or di-$C_{1-4}$alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, a $C_{1-4}$alkylsulfonylamino group, a $C_{1-4}$alkoxy-carbonyl group, a carboxyl group a $C_{1-4}$alkyl-carbonyl group, a carbamoyl group, a mono- or di-$C_{1-4}$alkyl-carbamoyl group, a $C_{1-6}$alkylsulfonyl group, a $C_{1-4}$alkyl group, an aminocarbonyloxy group, a mono- or di-$C_{1-4}$alkylamino-carbonyloxy group, a $C_{3-7}$cycloalkyl-carbonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenylsulfonyl group, a phenyl-$C_{1-4}$alkylsulfinyl group, a phenyl-$C_{1-4}$alkylsulfonylamino group and a phenylsulfonylamino group,
    wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group;
  n denotes an integer of 2; and
  $R^2$ and $R^3$ are respectively H, an unsubstituted hydrocarbon group, a hydrocarbon group substituted with 1 to 5 substituents selected from the group consisting of said substituent for said hydrocabon of $R^1$, an unsubstituted acyl group or a substituted acyl group,
    wherein said substituted acyl group is substituted with 1 to 3 substituents selected from the group consisting of a halogen atom, a nitro group, a hydroxy group, an amino group, a mono- or di-$C_{1-6}$alklamino group and a $C_{1-4}$alkoxy group, and
  $R^2$ and $R^3$ may form an unsubstituted N-containing saturated heterocyclic group or a substituted N-containing saturated heterocyclic group,
    wherein said substituted N-containing saturated heterocyclic group is substituted with 1 to 5 substituents selected from the group consisting of said substituted hydrocarbon group of $R^1$, an unsubstituted acyl group, said substituted acyl group for $R^2$ and $R^3$, a halogen atom, a nitro group, a cyano group, an oxo group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 of hetero atoms selected from the group consisting of nitrogen, oxygen and sulfur atoms, a $C_{1-4}$alkyl-carbonylamino group, a $C_{1-4}$alkylsulfonylamino group, a $C_{1-4}$alkoxy-carbonyl group, a phenyl-$C_{1-4}$alkyloxycarbonyl group, a carboxyl group, a $C_{1-6}$alkyl-carbonyl group, benzoyl group, a substituted benzoyl group, a carbamoyl group, a mono or di-$C_{1-4}$alkyl-carbamoyl group and a $C_{1-6}$alkylsulfonyl group,
    wherein said substituted benzoyl group is substituted with 1 to 3 substituents selected from the group consisting of a $C_{1-4}$alkyl group, a halogen atom, a $C_{1-4}$alkoxy group, a mono- or di-$C_{1-4}$alkylamine, a 5- to 7-membered cyclic amino group, a nitro group and a hydroxyl group, or a salt thereof, which comprises reacting a compound of the formula:

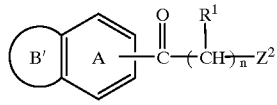

[IV]

wherein the ring A, the ring B', $R^1$ and n are as defined above; and $Z^2$ represents a leaving group, or a salt thereof, with a compound of the formula:

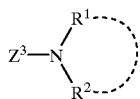

[V]

wherein $Z^3$ is a leaving group which can be left with $Z^2$; $R^2$ and $R^3$ are as defined above, or a salt thereof.

18. A method as claimed in claim 17, wherein provided that when the N-containing saturated heterocyclic group shown by Y of the compound of the formula [I'] has an unsubstituted amino group or a mono-substituted amino group, an unsubstituted hydrocarbon group, a hydrocarbon group substituted with 1 to 5 substituents selected from the group consisting of said substituent for said hydrocarbon of $R^2$, $R^3$ and $R^6$ is introduced into the N-containing saturated heterocyclic group by allowing the compound of the formula [I'] or a salt thereof to react with a compound of the formula:

$$R^7—Z^3$$ [XIII]

wherein $R^7$ is an unsubstituted hydrocarbon group, or a hydrocarbon group substituted with 1 to 5 substituent selected from the group consisting of said substituent for said hydrocarbon of $R^2$, $R^3$ and $R^6$; and $Z^3$ is a leaving group.

19. A pharmaceutical composition, which contains a compound of the formula:

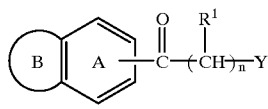

[I]

wherein ring A is an unsubstituted benzene ring or a substituted benzene ring wherein said substituted benzene ring is substituted with 1 to 3 substituents selected from the group consisting of a $C_{1-4}$alkyl group, a halogen atom, a nitro group, a cyano group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from nitrogen, oxygen and sulfur atoms, a $C_{1-4}$alkyl-carbonylamino group, an aminocarbonyloxy group, a mono- or di-$C_{1-4}$alkyl-carbonyloxy group, a $C_{1-4}$alkylsulfonylamino group, a $C_{1-4}$alkoxycarbonyl group, a carboxyl group, a $C_{1-4}$alkyl-carbonyl group, a $C_{3-7}$cycloalkyl carbonyl group, a carbamoyl group, a mono- or di-$C_{1-4}$alkyl-carbamoyl group, a $C_{1-6}$alkylsulfonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenylsulfonyl group, a phenyl-$C_{1-4}$alkylsulfinyl group, a phenyl-$C_{1-4}$alkylsulfonylamino group and a phenylsulfonylamino group, wherein each phenyl group or naphthyl group in the substituents may be substituted with 1 to 4 substituents selected from a $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group, and a benzoyl group;

ring B is a non-aromatic heterocyclic ring represented by the following formulae:

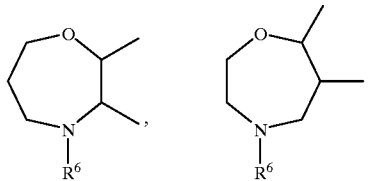

wherein $R^6$ is (1) a hydrogen atom, (2) a $C_{1-7}$ alkyl or a $C_{7-10}$ aralkyl group which may be substituted with a $C_{1-4}$ alkyl group, a halogen atom, a nitro group, a $C_{1-4}$ alkoxy group or a hydroxyl group, (3) a formyl group or (4) a $C_{2-8}$ alkylcarbonyl group;

$R^1$ is a hydrogen atom, an unsubstituted hydrocarbon group or a substituted hydrocarbon group, which may be different from one another in the repetition of n, wherein said substituted hydrocarbon group is substituted with 1 to 5 substituents selected from the group consisting of a halogen atom, a nitro group, a cyano group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from nitrogen, oxygen and sulfur atoms, a $C_{1-4}$alkyl-carbonylamino group, a $C_{1-4}$alkylsulfonylamino group, a $C_{1-4}$alkoxycarbonyl group, a carboxyl group, a $C_{1-6}$alkyl-carbonyl group, a carbamoyl group, a mono- or di-$C_{1-4}$alkyl-carbamoyl group, a $C_{1-6}$alkylsulfonyl group, a $C_{1-4}$alkyl group, an aminocarbonyloxy group, a mono- or di-$C_{1-4}$alkylamino-carbonyloxy group, a $C_{3-7}$cycloalkyl-carbonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenylsulfonyl group, a phenyl-$C_{1-4}$alkylsulfonyl group, a phenyl-$C_{1-4}$alkylsulfonylamino group and a phenyl-sulfonylamino group,
   wherein each phenyl group or naphthyl group in the substituents may be substituted with 1 to 4 substituents selected from a $C_{1-4}$alkyl group, $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group;
Y is an unsubstituted amino group, a substituted amino group, an unsubstituted N-containing saturated heterocyclic group, or a substituted N-containing saturated heterocyclic group,
   wherein said substituted amino group is substituted with 1 to 2 substituents selected from a hydrogen atom, an unsubstituted hydrocarbon group, said substituted hydrocarbon group of $R^1$, an unsubstituted acyl group and a substituted acyl group,
      wherein said substituted acyl group is substituted with 1 to 3 substituents selected from a halogen atom, a nitro group, a hydroxy group, an amino group, a mono- or di-$C_{1-6}$alkylamino group, and a $C_{1-4}$alkoxy group, and
   said substituted N-containing saturated heterocyclic group is substituted with 1 to 5 substituents selected from an unsubstituted hydrocarbon group, said substituted hydrocarbon group of $R^1$, an unsubstituted acyl group, said substituted acyl group for said substituted amino group of Y, a halogen atom, a nitro group, a cyano group, an oxo group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 of hetero atoms selected from nitrogen, oxygen and sulfur atoms, a $C_{1-4}$alkyl-carbonylamino group, a $C_{1-4}$alkylsulfonylamino group, a $C_{1-4}$alkoxy-carbonyl group, a phenyl-$C_{1-4}$alkyl-oxycarbonyl group, a carboxyl group, a $C_{1-6}$-carbonyl group, benzoyl group, a substituted benzoyl group, a carbamoyl group, a mono- or di-$C_{1-4}$alkyl-carbamoyl group, and a $C_{1-6}$alkylsulfonyl group
      wherein said substituted benzoyl group is substituted with 1 to 3 substituents selected from a $C_{1-4}$alkyl group, a halogen atom, a $C_{1-4}$alkoxy group, a mono- or di-$C_{1-4}$alkylamine, a 5- to 7-membered cyclic amino group, a nitro group, and a hydroxyl group; and
n denotes an integer of 2, or a pharmaceutically acceptable salt thereof.

20. A method for inhibiting acetylcholinesterase activity comprising administering to a mammal in need thereof a therapeutically effective amount of a compound of the formula:

[I]

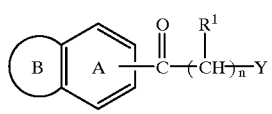

wherein ring A is an unsubstituted benzene ring or a substituted benzene ring,
   wherein said substituted benzene ring is substituted with 1 to 3 substituents selected from the group consisting of a $C_{1-4}$alkyl group, a halogen atom, a nitro group, a cyano group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, an aminocarbonyloxy group, a mono- or di-$C_{1-4}$alkylamino-carbonyloxy group, a $C_{1-4}$alkylsulfonylamino group, a $C_{1-4}$alkoxy-carbonyl group, a carboxyl group, a $C_{1-6}$alkyl-carbonyl group, a $C_{3-7}$cycloalkyl-carbonyl group, a carbamoyl group, a mono- or di-$C_{1-4}$alkyl-carbamoyl group, a $C_{1-6}$alkylsulfonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenyl-sulfonyl group, a phenyl-$C_{1-4}$alkylsulfinyl group, a phenyl-$C_{1-4}$alkylsulfonylamino group and a phenyl-sulfonylamino group,
   wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group;
ring B is a non-aromatic heterocyclic ring represented by the following formulae:

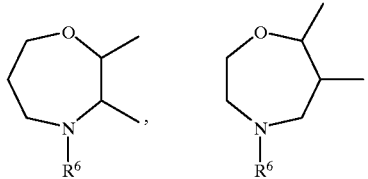

wherein $R^6$ is (1) a hydrogen atom, (2) a $C_{1-7}$ alkyl or a $C_{7-10}$ aralkyl group which may be substituted with a $C_{1-4}$ alkyl group, a halogen atom, a nitro group, a $C_{1-4}$ alkoxy group or a hydroxyl group, (3) a formyl group or (4) a $C_{2-8}$ alkylcarbonyl group;
$R^1$ is a hydrogen atom, an unsubstituted hydrocarbon group or a substituted hydrocarbon group, which may be different from one another in the repetition of n,
   wherein said substituted hydrocarbon group is substituted with 1 to 5 substituents selected from the group consisting of a halogen atom, a nitro group, a cyano group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 hetero atoms selected from the group consisting of nitrogen, oxygen and sulfur atoms, a $C_{1-4}$alkyl-carbonylamino group, a $C_{1-4}$alkylsulfonylamino group, a $C_{1-4}$alkoxy-carbonyl group, a carboxyl group, a $C_{1-6}$alkyl-carbonyl group, a carbamoyl group, a mono- or di-$C_{1-4}$alkyl-carbamoyl group, a $C_{1-6}$alkylsulfonyl group, a $C_{1-4}$alkyl group, an aminocarbonyloxy group, a mono- or di-$C_{1-4}$alkylamino-carboxyhexyl group, a $C_{3-7}$cycloalkylcarbonyl group, a $C_{3-7}$cycloalkylsulfonyl group, phenyl group, naphthyl group, a mono- or di-phenyl-$C_{1-3}$alkyl group, a phenoxy group, a benzoyl group, a phenoxycarbonyl group, a benzylcarbonyl group, a phenyl-$C_{1-4}$alkyl-carbamoyl group, a phenylcarbamoyl group, a phenyl-$C_{1-4}$alkyl-carbonylamino, benzoylamino group, a phenyl-$C_{1-4}$alkylsulfonyl group, a phenylsulfonyl group, a phenyl-$C_{1-4}$alkylsulfinyl group, a phenyl-$C_{1-4}$alkylsulfonylamino group, and a phenylsulfonylamino group, wherein each phenyl group or naphthyl group in the substituents may be substituted with 1 to 4 substituents selected from the group consisting of a $C_{1-4}$alkyl group, a $C_{1-4}$alkoxy group, a halogen atom, a hydroxyl group, a benzyloxy group, an amino group, a mono- or di-$C_{1-4}$alkylamino group, a nitro group, a $C_{1-6}$alkyl-carbonyl group and a benzoyl group;

Y is an unsubstituted amino group, a substituted amino group, an unsubstituted N-containing saturated heterocyclic group, or a substituted Ncontaining saturated heterocyclic group, wherein said substituted amino group is substituted with 1 to 2 substituents selected from the group consisting of a hydrogen atom, an unsubstituted hydrocarbon group, said substituted hydrocarbon group of $R^1$, an unsubstituted acyl group, and a substituted acyl group, wherein said substituted acyl group is substituted with 1 to 3 substituents selected from the group consisting of a halogen atom, a nitro group, a hydroxy group, an amino group, a mono- or di-$C_{1-6}$alkylamino group, and a $C_{1-4}$alkoxy group, and said substituted N-containing saturated heterocyclic group is substituted with 1 to 5 substituents selected from the group consisting of an unsubstituted hydrocarbon group, said substituted hydrocarbon group of $R^1$, an unsubstituted acyl group, said substituted acyl group for said substituted amino group of Y, a halogen atom, a nitro group, a cyano group, an oxo group, a hydroxyl group, a $C_{1-4}$alkoxy group, a $C_{1-4}$alkylthio group, an amino group, a mono- or di-$C_{1-4}$alkylamino group, a 5- to 7-membered cyclic amino group which may have, other than carbon atoms and one nitrogen atom, 1 to 3 of hetero atoms selected from the group consisting of nitrogen, oxygen and sulfur atoms, a $C_{1-4}$alkyl-carbonylaminmo group, a $C_{1-4}$alkylsulfonylamino group, a $C_{1-4}$alkoxy-carbonyl group, a phenyl-$C_{1-4}$alkyl-oxycarbonyl group, a carboxyl group, a $C_{1-6}$alkyl-carbonyl group, benzoyl group, a substituted benzoyl group, a carbamoyl group, a mono- or di-$C_{1-4}$alkyl-carbamoyl group and a $C_{1-6}$alkylsulfonyl group wherein said substituted benzoyl group is substituted with 1 to 3 substituents selected from the group consisting of a $C_{1-4}$alkyl group, a halogen atom, a $C_{1-4}$alkoxy group, a mono- or di-$C_{1-4}$alklamine, a 5- to 7-membered cyclic amino group, a nitro group, and a hydroxyl group; and n denotes an integer of 2, or a pharmaceutically acceptable salt thereof, together with a pharmaceutically acceptable carrier to a mammal.

21. A method of treating Alzheimer's disease and/or senile demetia which comprises administering a therapeutically effective amount of a compound of claim 1 or a pharmaceutically acceptable salt thereof to a mammal in need thereof.

\* \* \* \* \*